US010612011B2

(12) United States Patent
Liu et al.

(10) Patent No.: US 10,612,011 B2
(45) Date of Patent: Apr. 7, 2020

(54) EVOLUTION OF TALENS

(71) Applicant: President and Fellows of Harvard College, Cambridge, MA (US)

(72) Inventors: David R. Liu, Lexington, MA (US); Basil Hubbard, Edmonton (CA); Ahmed Hussein Badran, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 14 days.

(21) Appl. No.: 15/748,053

(22) PCT Filed: Jul. 28, 2016

(86) PCT No.: PCT/US2016/044546
§ 371 (c)(1),
(2) Date: Jan. 26, 2018

(87) PCT Pub. No.: WO2017/019895
PCT Pub. Date: Feb. 2, 2017

(65) Prior Publication Data
US 2018/0237758 A1 Aug. 23, 2018

Related U.S. Application Data

(60) Provisional application No. 62/198,906, filed on Jul. 30, 2015.

(51) Int. Cl.
| C12N 9/96 | (2006.01) |
| C12N 9/22 | (2006.01) |
| C12N 15/62 | (2006.01) |
| C12N 15/85 | (2006.01) |
| C12N 15/90 | (2006.01) |
| A61K 48/00 | (2006.01) |

(52) U.S. Cl.
CPC .............. *C12N 9/22* (2013.01); *C12N 15/62* (2013.01); *C12N 15/8509* (2013.01); *C12N 15/90* (2013.01); *A61K 48/0066* (2013.01); *A61K 48/0091* (2013.01)

(58) Field of Classification Search
CPC .................................. C12N 15/62; C12N 9/22
USPC ......................................................... 435/188
See application file for complete search history.

(56) References Cited

U.S. PATENT DOCUMENTS

| 5,057,432 A | 10/1991 | Wangersky et al. |
| 5,223,409 A | 6/1993 | Ladner et al. |
| 5,658,727 A | 8/1997 | Barbas et al. |
| 5,712,089 A | 1/1998 | Borrebaeck et al. |
| 5,821,047 A | 10/1998 | Garrard et al. |
| 5,880,275 A | 3/1999 | Fischhoff et al. |
| 5,965,124 A | 10/1999 | Feinberg et al. |
| 6,033,874 A | 3/2000 | Baum et al. |
| 6,156,509 A | 12/2000 | Schellenberger |
| 6,429,298 B1 | 8/2002 | Ellington et al. |
| 6,713,063 B1 | 3/2004 | Malvar et al. |
| 6,962,705 B2 | 11/2005 | Malvar et al. |
| 6,969,731 B1 | 11/2005 | Tang et al. |
| 7,064,249 B2 | 6/2006 | Corbin et al. |
| 7,070,982 B2 | 7/2006 | Malvar et al. |
| 9,023,594 B2 | 5/2015 | Liu et al. |
| 9,267,127 B2 | 2/2016 | Liu et al. |
| 9,359,599 B2 | 6/2016 | Liu et al. |
| 9,394,537 B2 | 7/2016 | Liu et al. |
| 9,567,589 B2 | 2/2017 | Jin et al. |
| 9,766,216 B2 | 9/2017 | Wada et al. |

(Continued)

FOREIGN PATENT DOCUMENTS

| EP | 0289479 A2 | 11/1988 |
| EP | 3 115 457 A1 | 1/2017 |
| JP | H0937764 A | 2/1997 |
| JP | 2011-081011 | 4/2011 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 94/18316 A2 | 8/1994 |

(Continued)

OTHER PUBLICATIONS

Extended European Search Report for EP 09812363, dated Mar. 30, 2012.

(Continued)

*Primary Examiner* — Tekchand Saidha
(74) *Attorney, Agent, or Firm* — Wolf, Greenfield & Sacks, P.C.

(57) ABSTRACT

Engineered transcriptional activator-like effectors (TALEs) are versatile tools for genome manipulation with applications in research and clinical contexts. One current drawback of TALEs is that the 5' nucleotide of the target is specific for thymine (T). TALE domains with alternative 5' nucleotide specificities could expand the scope of DNA target sequences that can be bound by TALEs. This disclosure provides methods and strategies for the continuous evolution of proteins comprising DNA-binding domains, e.g., TALE domains. In some aspects, this disclosure provides methods and strategies for evolving such proteins under positive selection for a desired DNA-binding activity and/or under negative selection against one or more undesired (e.g., off-target) DNA-binding activities. Some aspects of this disclosure provide engineered TALE domains and TALEs comprising such engineered domains, e.g., TALE nucleases (TALENs), TALE transcriptional activators, TALE transcriptional repressors, and TALE epigenetic modification enzymes, with altered 5' nucleotide specificities of target sequences. Engineered TALEs that target ATM with greater specificity are also provided.

7 Claims, 45 Drawing Sheets

Specification includes a Sequence Listing.

(56) References Cited

U.S. PATENT DOCUMENTS

| | | | |
|---|---|---|---|
| 9,771,574 B2 | 9/2017 | Liu et al. | |
| 10,179,911 B2 | 1/2019 | Liu et al. | |
| 10,227,581 B2 | 3/2019 | Liu et al. | |
| 10,336,997 B2 | 7/2019 | Liu et al. | |
| 10,392,674 B2 | 8/2019 | Liu et al. | |
| 2002/0132327 A1 | 9/2002 | Hay et al. | |
| 2003/0119764 A1 | 6/2003 | Loeb et al. | |
| 2003/0203480 A1 | 10/2003 | Kovesdi et al. | |
| 2005/0019753 A1 | 1/2005 | Kukolj et al. | |
| 2006/0112447 A1 | 5/2006 | Bogdanova et al. | |
| 2008/0220502 A1 | 9/2008 | Schellenberger et al. | |
| 2009/0215110 A1 | 8/2009 | Gibson et al. | |
| 2009/0227463 A1 | 9/2009 | Reif et al. | |
| 2009/0300777 A1 | 12/2009 | Nakayama | |
| 2011/0177495 A1 | 7/2011 | Liu et al. | |
| 2012/0231498 A1 | 9/2012 | Shaw et al. | |
| 2013/0059931 A1 | 3/2013 | Petersen-Mahrt et al. | |
| 2013/0117869 A1 | 5/2013 | Duchateau et al. | |
| 2013/0345065 A1 | 12/2013 | Liu et al. | |
| 2014/0057317 A1 | 2/2014 | Liu et al. | |
| 2014/0201858 A1 | 7/2014 | Ostertag et al. | |
| 2015/0056177 A1* | 2/2015 | Liu | C12N 9/22 424/94.3 |
| 2015/0275202 A1 | 10/2015 | Liu et al. | |
| 2016/0002301 A1 | 1/2016 | Je et al. | |
| 2016/0201040 A1 | 2/2016 | Liu et al. | |
| 2016/0348096 A1 | 12/2016 | Liu et al. | |
| 2017/0009224 A1 | 1/2017 | Liu et al. | |
| 2017/0029473 A1 | 2/2017 | Liu et al. | |
| 2017/0044520 A1 | 2/2017 | Liu et al. | |
| 2017/0233708 A1 | 8/2017 | Liu et al. | |
| 2018/0057545 A9 | 3/2018 | Liu et al. | |
| 2018/0087046 A1 | 3/2018 | Liu et al. | |
| 2019/0276816 A1 | 9/2019 | Liu et al. | |

FOREIGN PATENT DOCUMENTS

| | | |
|---|---|---|
| WO | WO 96/04403 A1 | 2/1996 |
| WO | WO 98/32845 A1 | 7/1998 |
| WO | WO 2000/71694 A1 | 11/2000 |
| WO | WO 2001/05950 A2 | 1/2001 |
| WO | WO 2001/61049 A1 | 8/2001 |
| WO | WO 2005/081632 A2 | 9/2005 |
| WO | WO 2007/066923 A1 | 6/2007 |
| WO | WO 2008/005529 A2 | 1/2008 |
| WO | WO 2009/082488 A2 | 7/2009 |
| WO | WO 2009/108180 A2 | 9/2009 |
| WO | WO 2010/028347 A2 | 3/2010 |
| WO | WO 2011/147590 A2 | 12/2011 |
| WO | WO 2011/066747 A1 | 6/2012 |
| WO | WO 2012/088381 A2 | 6/2012 |
| WO | WO 2012/138927 A2 | 10/2012 |
| WO | WO 2013/047844 | 4/2013 |
| WO | WO 2014/039585 A2 | 3/2014 |
| WO | WO 2014/157820 A1 | 10/2014 |
| WO | WO 2014/158593 A1 | 10/2014 |
| WO | WO 2017/070632 A2 | 4/2017 |
| WO | WO 2018/039438 A1 | 3/2018 |

OTHER PUBLICATIONS

Extended European Search Report for EP 16 20 3684, dated May 26, 2017.
International Search Report and Written Opinion for PCT/US2009/056194, dated Jun. 21, 2010.
International Preliminary Report on Patentability for PCT/US2009/056194, dated Mar. 17, 2011.
Extended European Search Report for EP 17 16 0955, dated May 16, 2017.
Invitation to Pay Additional Fees for PCT/US2011/066747, dated Aug. 30, 2012.
International Search Report and Written Opinion for PCT/US2011/066747, dated Oct. 30, 2012.
International Preliminary Report on Patentability for PCT/US2011/066747, dated Jul. 4, 2013.
International Search Report and Written Opinion for PCT/US2015/012022, dated Sep. 25, 2015.
International Preliminary Report on Patentability for PCT/US2015/012022, dated Aug. 4, 2016.
Invitation to Pay Additional Fees for PCT/US/2016/043559, dated Jan. 12, 2017.
International Search Report and Written Opinion for PCT/US/2016/043559, dated Mar. 10, 2017.
International Preliminary Report on Patentability for PCT/US/2016/043559, dated Feb. 1, 2018.
International Search Report and Written Opinion for PCT/US2015/057012, dated Jun. 10, 2016.
International Preliminary Report on Patentability for PCT/US2015/057012, dated May 4, 2017.
International Search Report and Written Opinion for PCT/US2016/027795, dated Aug. 11, 2016.
International Preliminary Report on Patentability for PCT/US2016/027795, dated Oct. 26, 2017.
Invitation to Pay Additional Fees for PCT/US2016/044546, dated Oct. 12, 2016.
International Search Report and Written Opinion for PCT/US2016/044546, dated Dec. 28, 2016.
International Preliminary Report on Patentability for PCT/US2016/044546, dated Feb. 8, 2018.
International Search Report and Written Opinion for PCT/US2016/043513, dated Nov. 30, 2016.
International Preliminary Report on Patentability for PCT/US2016/043513, dated Feb. 1, 2018.
Invitation to Pay Additional Fees for PCT/US2018/14867, dated Apr. 5, 2018.
Ahluwalia et al., Hypermutability and error catastrophe due to defects in ribonucleotide reductase. Proc Natl Acad Sci USA. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 22, 2003;100(15):8688-91. Epub Jul. 1, 2003.
Armstrong et al., Chapter 3. Vectors for Phage Display. In: Phage Display of Peptides and Proteins. Kay et al., eds. Academic Press. San Diego, CA. 1996:35-53.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. 2014;1-10.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Boch et al., Breaking the code of DNA binding specificity of TAL-type III effectors. Science. Dec. 11, 2009;326(5959):1509-12. doi: 10.1126/science.1178811.
Boeke et al., Effects of bacteriophage f1 gene III protein on the host cell membrane. Mol Gen Genet. 1982;186(2):185-92.
Boersma et al., Selection strategies for improved biocatalysts. FEBS J. May 2007;274(9):2181-95.

(56) References Cited

OTHER PUBLICATIONS

Bolusani et al., Evolution of variants of yeast site-specific recombinase Flp that utilize native genomic sequences as recombination target sites. Nucleic Acids Res. 2006;34(18):5259-69. Epub Sep. 26, 2006.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Caldwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Clackson et al., Making antibody fragments using phage display libraries. Nature. Aug. 15, 1991;352(6336):624-8.
Click et al., Filamentous phage infection: required interactions with the TolA protein. J Bacteriol. Oct. 1997;179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in *Escherichia coli* K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dickinson et al., Experimental interrogation of the path dependence and stochasticity of protein evolution using phage-assisted continuous evolution. Proc Natl Acad Sci USA. May 2013;110(22):9007-12.
Dickinson et al., A system for the continuous directed evolution of proteases rapidly reveals drug-resistance mutations. Nat Commun. Oct. 30, 2014;5:5352. doi: 10.1038/ncomms6352.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci U S A. Aug. 15, 1991;88(16):7160-4.
Durai et al., A bacterial one-hybrid selection system for interrogating zinc finger—DNA interactions. Comb Chem High Throughput Screen. May 2006;9(4):301-11.
Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.
Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fuchs et al., Targeting Recombinant Antibodies to the Surface of *Escherichia coli*: Fusion to a Peptidoglycan Associated Lipoprotein. Bio/Technology. 1991;9:1370-72.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993;12(2):725-34.
Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and *Escherichia coli* expression of a human IgM Fab. Hum Antibodies Hybridomas. Apr. 1992;3(2):81-5.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hu et al., *Escherichia coli* one- and two-hybrid systems for the analysis and identification of protein-protein interactions. Methods. Jan. 2000;20(1):80-94.

(56) References Cited

OTHER PUBLICATIONS

Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.
Huse et al., Generation of a large combinatorial library of the immunoglobulin repertoire in phage lambda. Science. Dec. 8, 1989;246(4935):1275-81.
Husimi et al., Cellstat—a continuous culture system of a bacteriophage for the study of the mutation rate and the selection process of the DNA level. Rev Sci Instrum. Apr. 1982;53(4):517-22.
Husimi, Selection and evolution of bacteriophages in cellstat. Adv Biophys. 1989;25:1-43.
Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.
Imburgio et al., Studies of promoter recognition and start site selection by T7 RNA polymerase using a comprehensive collection of promoter variants. Biochemistry. Aug. 29, 2000;39(34):10419-30.
Irion et al., Identification and targeting of the ROSA26 locus in human embryonic stem cells. Nat Biotechnol. Dec. 2007;25(12):1477-82. Epub Nov. 25, 2007.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joung et al., A bacterial two-hybrid selection system for studying protein—DNA and protein-protein interactions. Proc Natl Acad Sci U S A. Jun. 20, 2000;97(13):7382-7.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Khlebnikov et al., Modulation of gene expression from the arabinose-inducible araBAD promoter. J Ind Microbiol Biotechnol. Jul. 2002;29(1):34-7.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Kozak et al., Structural features in eukaryotic mRNAs that modulate the initiation of translation. J Biol Chem. Oct. 25, 1991;266(30):19867-70.
Kuzmine et al., Binding of the priming nucleotide in the initiation of transcription by T7 RNA polymerase. J Biol Chem. Jan. 31, 2003;278(5):2819-23. Epub Nov. 9, 2002.
Latimer et al., Specificity of monoclonal antibodies produced against phosphorothioate and ribo modified DNAs. Mol Immunol. Oct. 1995;32(14-15):1057-64.
Leconte et al., A population-based experimental model for protein evolution: effects of mutation rate and selection stringency on evolutionary outcomes. Biochemistry. Feb. 26, 2013;52(8): 1490-1499.
Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.
Lincoln et al., Self-sustained replication of an RNA enzyme. Science. Feb. 27, 2009;323(5918):1229-32. Epub Jan. 8, 2009.
Lindemann et al., Evolution of bacteriophage in continuous culture: a model system to test antiviral gene therapies for the emergence of phage escape mutants. J Virol. Jun. 2002;76(11):5784-92.
Lutz et al., Creating multiple-crossover DNA libraries independent of sequence identity. Proc Natl Acad Sci U S A. Sep. 25, 2001;98(20):11248-53. Epub Sep. 18, 2001.
Maeder et al., Robust, synergistic regulation of human gene expression using TALE activators. Nat Methods. Mar. 2013;10(3):243-5. doi: 10.1038/nmeth.2366. Epub Feb. 10, 2013.
Makeyev et al., Evolutionary potential of an RNA virus. J Virol. Feb. 2004;78(4):2114-20.
Malmborg et al., Selective phage infection mediated by epitope expression on F pilus. J Mol Biol. Oct. 31, 1997;273(3):544-51.
Martin et al., Kinetic analysis of T7 RNA polymerase-promoter interactions with small synthetic promoters. Biochemistry. May 19, 1987;26(10):2690-6.
McCafferty et al., Phage antibodies: filamentous phage displaying antibody variable domains. Nature. Dec. 6, 1990;348(6301):552-4.
McConnell et al., Constrained peptide libraries as a tool for finding mimotopes. Gene. Dec. 30, 1994;151(1-2):115-8.
Milligan et al., Oligoribonucleotide synthesis using T7 RNA polymerase and synthetic DNA templates. Nucleic Acids Res. Nov. 11, 1987;15(21):8783-98.
Mills et al., An extracellular Darwinian experiment with a self-duplicating nucleic acid molecule. Proc Natl Acad Sci U S A. Jul. 1967;58(1):217-24.
Nelson et al., Filamentous phage DNA cloning vectors: a noninfective mutant with a nonpolar deletion in gene III. Virology. Jan. 30, 1981;108(2):338-50.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
O'Maille et al., Structure-based combinatorial protein engineering (SCOPE). J Mol Biol. Aug. 23, 2002;321(4):677-91.
Opperman et al., A model for a umuDC-dependent prokaryotic DNA damage checkpoint. Proc Natl Acad Sci U S A. Aug. 3, 1999;96(16):9218-23.
Ostendorf et al., Characterization of a dam mutant of Serratia marcescens and nucleotide sequence of the dam region. J Bacteriol. Jul. 1999;181(13):3880-5.
Ostermeier e al., A combinatorial approach to hybrid enzymes independent of DNA homology. Nat Biotechnol. Dec. 1999;17(12):1205-9.
Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pu et al., Evolution of a split RNA polymerase as a versatile biosensor platform. Nat Chem Biol. Apr. 2017;13(4):432-438. doi: 10.1038/nchembio.2299. Epub Feb. 13, 2017.
Rakonjac et al., Filamentous phage are released from the bacterial membrane by a two-step mechanism involving a short C-terminal fragment of pIII. J Mol Biol. Jun. 25, 1999;289(5):1253-65.
Rakonjac et al., Filamentous phage infection-mediated gene expression: construction and propagation of the gIII deletion mutant helper phage R408d3. Gene. Oct. 1, 1997;198(1-2):99-103.
Rakonjac et al., Roles of pIII in filamentous phage assembly. J Mol Biol. Sep. 11, 1998;282(1):25-41.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 RNA polymerase mutants with altered promoter specificities. Proc Natl Acad Sci U S A. Apr. 15, 1993;90(8):3147-51.
Rebar et al., Phage display methods for selecting zinc finger proteins with novel DNA-binding specificities. Methods Enzymol. 1996;267:129-49.
Reidhaar-Olson et al., Random mutagenesis of protein sequences using oligonucleotide cassettes. Methods Enzymol. 1991;208:564-86.

(56) References Cited

OTHER PUBLICATIONS

Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.
Riechmann et al., The C-terminal domain of TolA is the coreceptor for filamentous phage infection of *E. coli*. Cell. Jul. 25, 1997;90(2):351-60.
Ringquist et al., Translation initiation in *Escherichia coli*: sequences within the ribosome-binding site. Mol Microbiol. May 1992;6(9):1219-29.
Rosenberg et al., T7 Select® Phage Display System: A Powerful new protein display system based on bacteriophage T7. Innovations. 1996;6:1-6.
Santini et al., Efficient display of an HCV cDNA expression library as C-terminal fusion to the capsid protein D of bacteriophage lambda. J Mol Biol. Sep. 11, 1998;282(1):125-35.
Santoro et al., Directed evolution of the site specificity of Cre recombinase. Proc Natl Acad Sci U S A. Apr. 2, 2002;99(7):4185-90. Epub Mar. 19, 2002.
Schultz et al., Oligo-2'-fluoro-2'-deoxynucleotide N3'-->P5' phosphoramidates: synthesis and properties. Nucleic Acids Res. Aug. 1, 1996;24(15):2966-73.
Scott et al., Searching for peptide ligands with an epitope library. Science. Jul. 27, 1990;249(4967):386-90.
Sices et al., A genetic screen for the isolation and characterization of site-specific proteases. Proc Natl Acad Sci U S A. Mar. 17, 1998;95(6):2828-33.
Sices et al., Rapid genetic selection of inhibitor-resistant protease mutants: clinically relevant and novel mutants of the HIV protease. AIDS Res Hum Retroviruses. Sep. 1, 2001;17(13):1249-55.
Sieber et al., Libraries of hybrid proteins from distantly related sequences. Nat Biotechnol. May 2001;19(5):456-60.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Smith, Filamentous fusion phage: novel expression vectors that display cloned antigens on the virion surface. Science. Jun. 14, 1985;228(4705):1315-7.
Stemmer, Rapid evolution of a protein in vitro by DNA shuffling. Nature. Aug. 4, 1994;370(6488):389-91.
Sutter et al., Non-replicating vaccinia vector efficiently expresses bacteriophage T7 RNA polymerase. FEBS Lett. Aug. 28, 1995;371(1):9-12.
Torres et al., Non-integrative lentivirus drives high-frequency cre-mediated cassette exchange in human cells. PLoS One. 2011;6(5):e19794. doi: 10.1371/journal.pone.0019794. Epub May. 23, 2011.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tsuji et al., Random multi-recombinant PCR for the construction of combinatorial protein libraries. Nucleic Acids Res. Oct. 15, 2001;29(20):E97.
Tzagoloff et al., The Initial Steps in Infection With Coliphage M13. Virology. Nov. 1964;24:372-80.
Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.

Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wright et al., Continuous in vitro evolution of catalytic function. Science. Apr. 25, 1997;276(5312):614-7.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
International Search Report and Written Opinion for PCT/US2014/052231, dated Jan. 30, 2015.
Preliminary Report on Patentability for PCT/US2014/052231, dated Mar. 3, 2016.
International Search Report and Written Opinion for PCT/US2018/14867, dated May 23, 2018.
International Search Report and Written Opinion for PCT/US2018/051557, dated Feb. 25, 2019.
International Search Report and Written Opinion for PCT/US2018/044242, dated Nov. 21, 2018.
Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Komor et al., Programmable editing of a target base in genomic DNA without double-stranded DNA cleavage. Nature. May. 19, 2016;533(7603):420-4. doi: 10.1038/nature17946. Epub Apr. 20, 2016.
McNaughton et al., Mammalian cell penetration, siRNA transfection, and DNA transfection by supercharged proteins. Proc Natl Acad Sci USA. Apr. 14, 2009;106(15):6111-6. doi: 10.1073/pnas.0807883106. Epub Mar. 23, 2009.
Miller et al., A TALE nuclease architecture for efficient genome editing. Nat Biotechnol. Feb. 2011;29(2):143-8. doi:10.1038/nbt.1755. Epub Dec. 22, 2010.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Yamamoto et al., Virological and immunological bases for HIV-1 vaccine design. Uirusu 2007;57(2):133-139. https://doi.org/10.2222/jsv.57.133.
International Preliminary Report on Patentability for PCT/US2018/14867 dated Aug. 1, 2019.
International Search Report and Written Opinion for Application No. PCT/US2019/037216 dated Sep. 4, 2019.
[No Author Listed] NCBI Accession No. XP_015843220.1. C ->U editing enzyme APOBEC-1 [Peromyscus maniculatus bairdii], XP002793540.
[No Author Listed] NCBI Accession No. XP_021505673.1. C ->U editing enzyme APOBEC-1 [Meriones unguiculatus], XP002793541.
Kim et al., Increasing the genome-targeting scope and precision of base editing with engineered Cas9-cytidine deaminase fusions. Nature Biotechnology; Feb. 13, 2007; 35(4): 371-376.
Wang et al., Continuous directed evolutions of proteins with improved soluble expression. Nature Chemical Biology. Nat Publishing Group. Aug. 20, 2018; 14(10):972-980.

\* cited by examiner

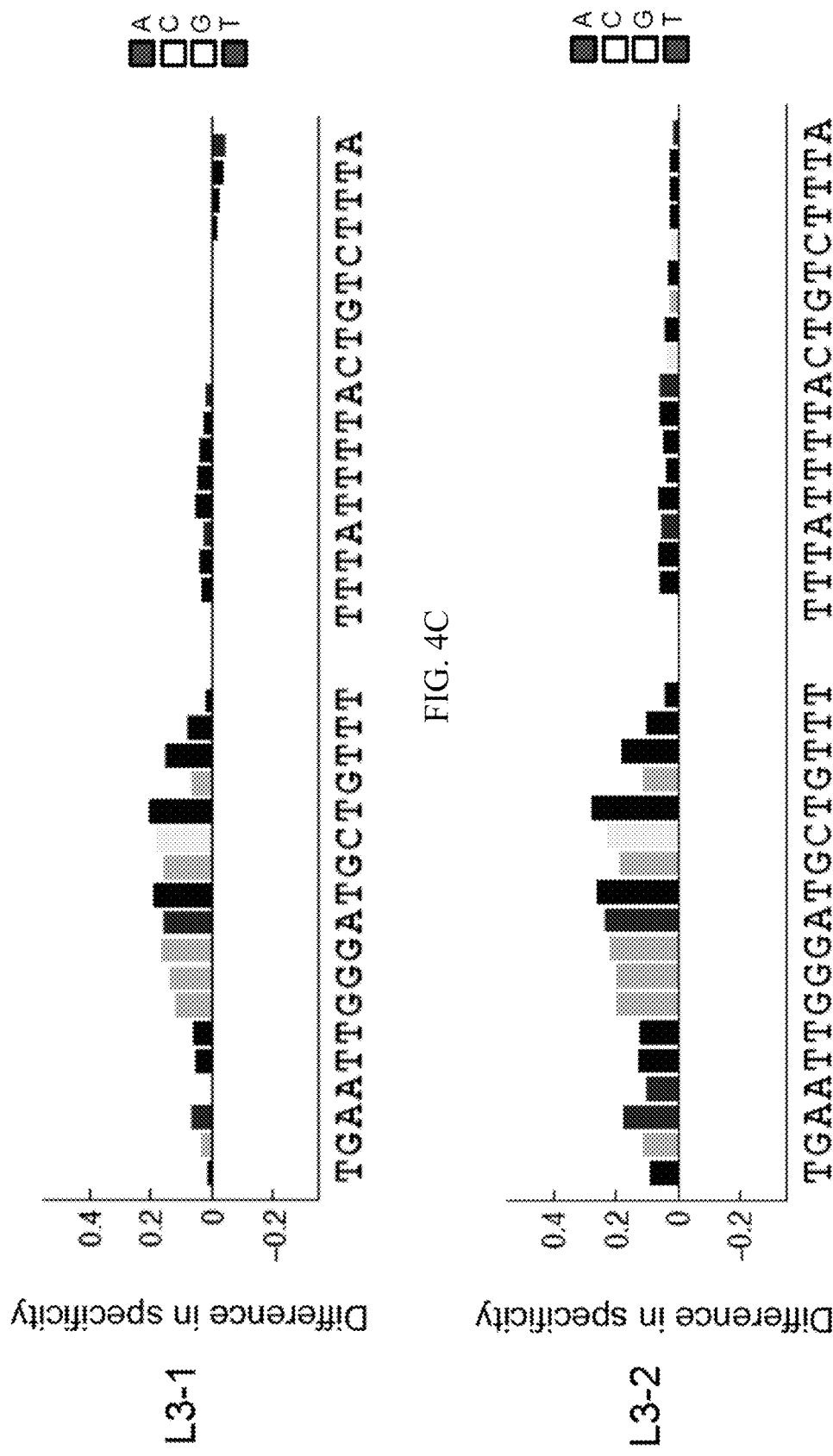

| SP: | Pos. control (1059) | Neg. control (1030) | Activity assay (1030 +AP) |
|---|---|---|---|
| Wild-type Zif268 | + | − | + |
| R24V Zif268 | + | − | − |
| Phage following PACE | + | − | + |

FIG. 9C

```
              20   21   22   23   24   25   26   27   28
Wild-type: ...GAT  GAG  CTT  ACC  CGC  CAT  ATC  CGC  ATC...
              D    E    L    T    R    H    I    R    I
   Initial: ...GAT  GAG  CTT  ACC  GTA  CAT  ATC  CGC  ATC...
              D    E    L    T    V    H    I    R    I
       C1: ...GAT  GAG  CTT  ACC  AGA  CAT  ATC  CGC  ATC...
       C2: ...GAT  GAG  CTT  ACC  AGA  CAT  ATC  CGC  ATC...
PACE   C3: ...GAT  GAG  CTT  ACC  AGA  CAT  ATC  CGC  ATC...
       C4: ...GAT  GAG  CTT  ACC  AGA  CAT  ATC  CGC  ATC...
       C5: ...GAT  GAG  CTT  ACC  AGA  CAT  ATC  CGC  ATC...
              D    E    L    T    R    H    I    R    I
```

FIG. 9D

|    | pII/pX        | pV | pIX pVIII | pVIII | Kan | TALE  | Ω              | pIII | pIV | pI    | pIV   |
|----|---------------|----|-----------|-------|-----|-------|----------------|------|-----|-------|-------|
| C1 | F66L<br>I78M  |    |           |       | R6W |       | A8V<br>(A737V) |      |     | R303G |       |
| C2 | E65G<br>F66L  |    |           |       | R6W |       | A8V<br>(A737V) |      |     | R303G |       |
| C3 | F66L<br>I91M  |    |           |       | R6W | R302L | A8V<br>(A737V) |      |     | R303G |       |
| C4 | F66L          |    |           |       | R6W |       | A8V<br>(A737V) |      |     | R303G | P106T |
| C5 | F66L          |    |           |       | R6W |       | A8V<br>(A737V) |      |     | R303G |       |

FIG. 10C

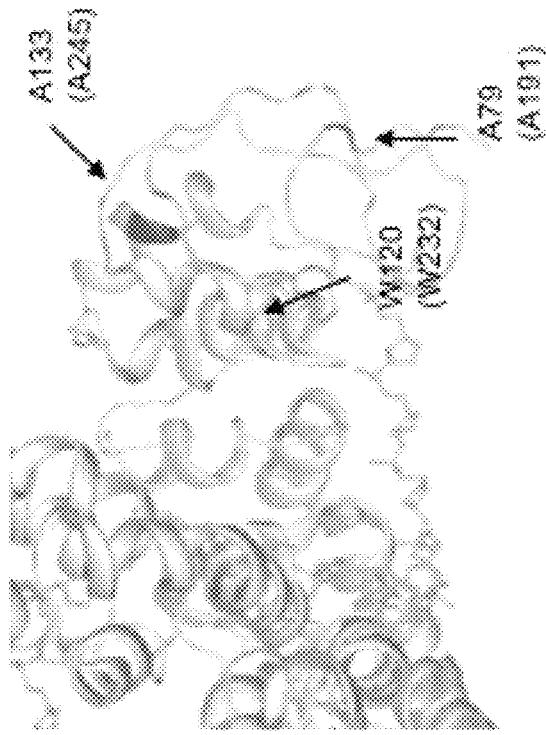
FIG. 13A
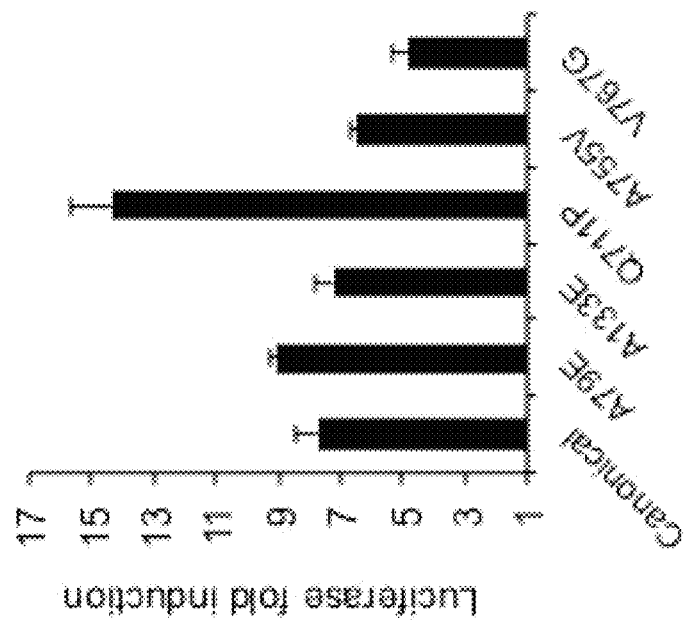
FIG. 13B
FIG. 13C

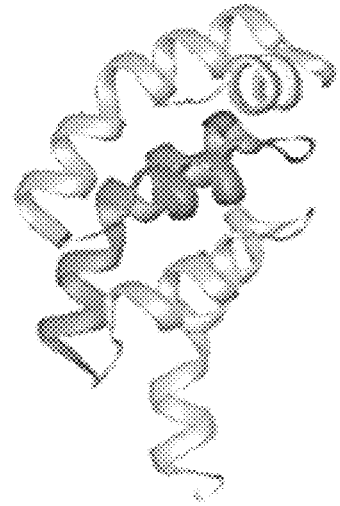
L508F: Repeat 10 (pos. 26)
FIG. 13F
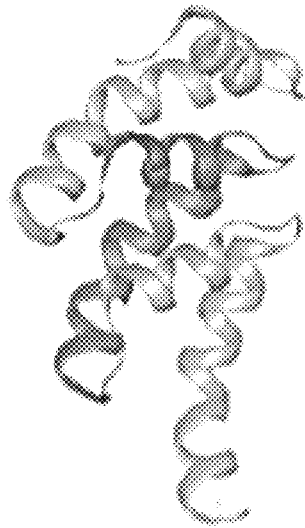
E622K: Repeat 14 (pos. 4)
FIG. 13G
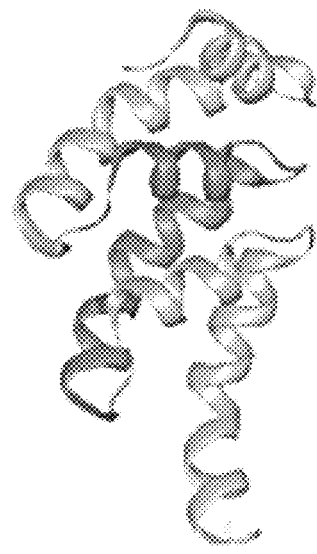
K634R: Multiple repeats (pos. 16)
FIG. 13H
| SP. | Positive control (1059) | Negative control (S1030) | Activity dependent (5'A) | Activity dependent (5'C) | Activity dependent (5'G) | Activity dependent (5'T) |
|---|---|---|---|---|---|---|
| Initial phage | +++ | – | + | – | – | +++ |
| Evolved 5'A phage | +++ | – | +++ | +++ | +++ | +++ |
| Evolved 5'C phage | +++ | – | +++ | +++ | +++ | +++ |
| Evolved 5'G phage | +++ | – | +++ | +++ | +++ | +++ |
FIG. 14A

| mM Theophylline | 0 | 0.01 | 0.1 | 1 |
|---|---|---|---|---|
| Ap5'A/ApNeg5'T | +++ | +++ | + | — |
| Ap5'A/ApNeg5'C | +++ | +++ | ++ | — |
| Ap5'A/ApNeg5'G | +++ | +++ | ++ | — |
| Ap5'A/ApNegScr. | +++ | +++ | +++ | — |
| S1030 (Neg. control) | — | — | — | — |

FIG. 14B

| mM Theophylline | 0 | 0.1 | 0.2 | 0.4 | 0.8 |
|---|---|---|---|---|---|
| Ap5'A/ApNeg5'T | +++ | + | — | — | — |
| Ap5'A/ApNeg5'C | +++ | ++ | + | — | — |
| Ap5'A/ApNeg5'G | +++ | ++ | + | — | — |
| Ap5'A/ApNegScr. | +++ | +++ | +++ | +++ | + |
| S1030 (Neg. control) | — | — | — | — | — |

FIG. 14C

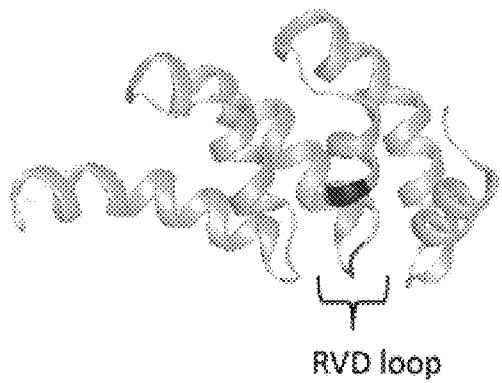
FIG. 19C
FIG. 19D
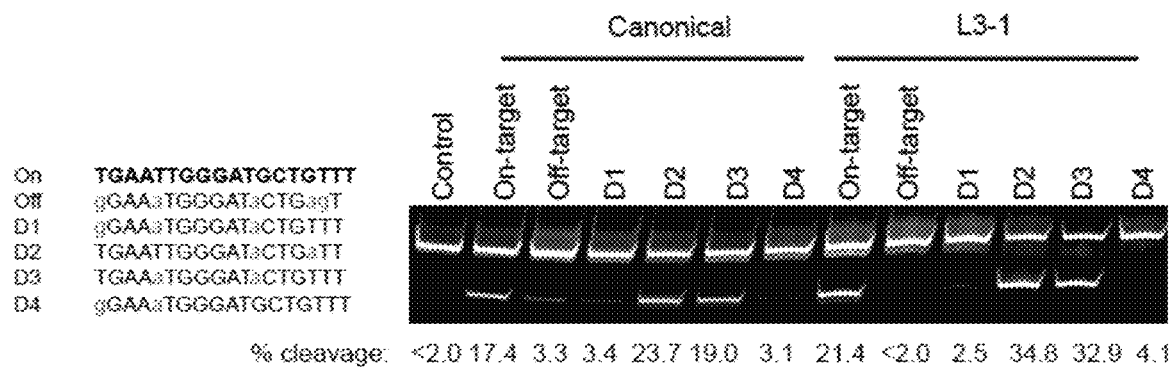
FIG. 19E
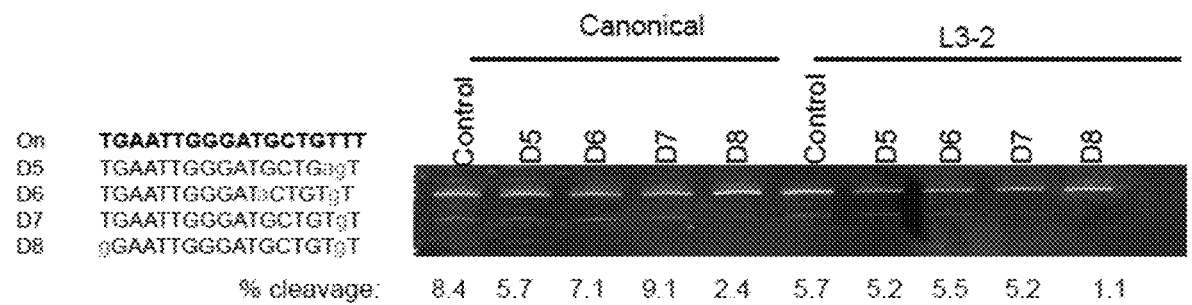
FIG. 19F

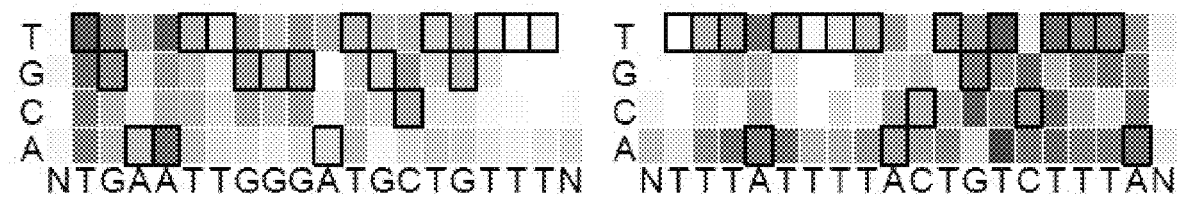
FIG. 21A
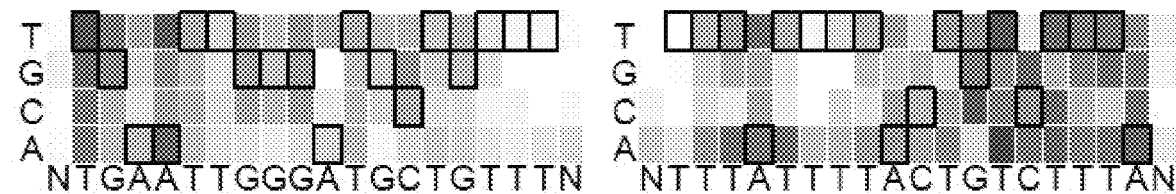
FIG. 21B
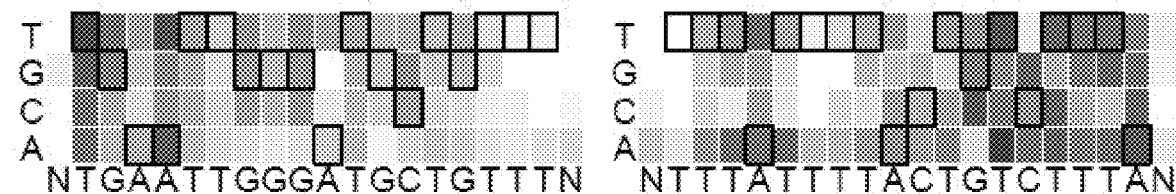
FIG. 21C
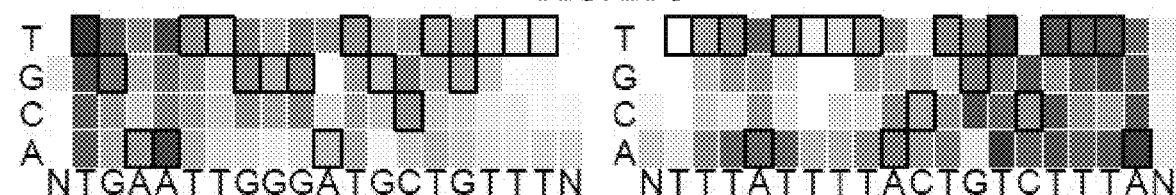
FIG. 21D
Specificity score
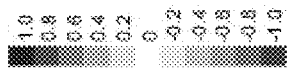

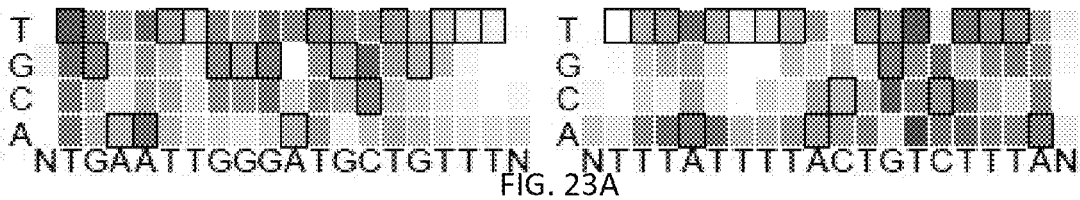
FIG. 23A
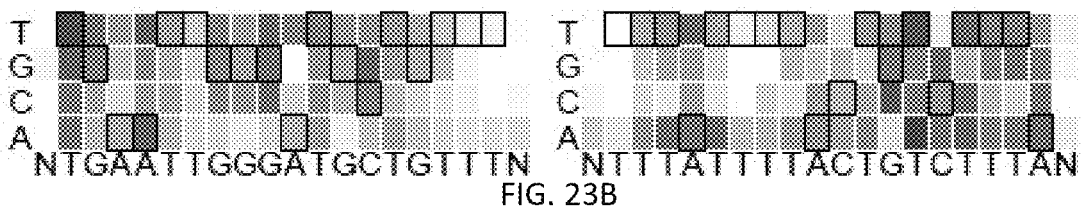
FIG. 23B
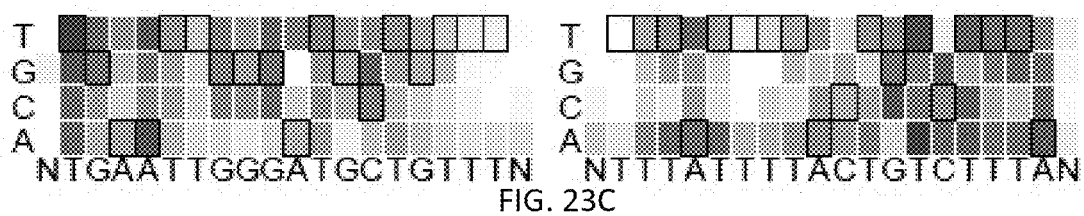
FIG. 23C
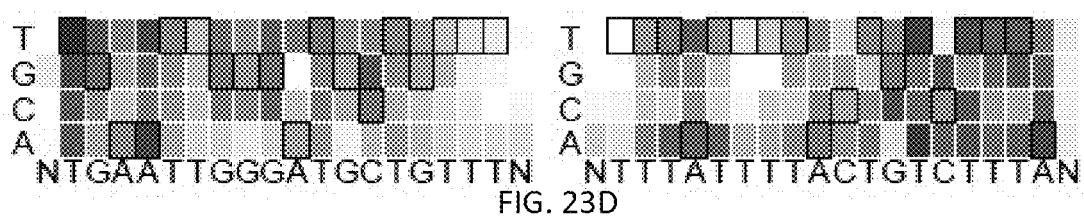
FIG. 23D
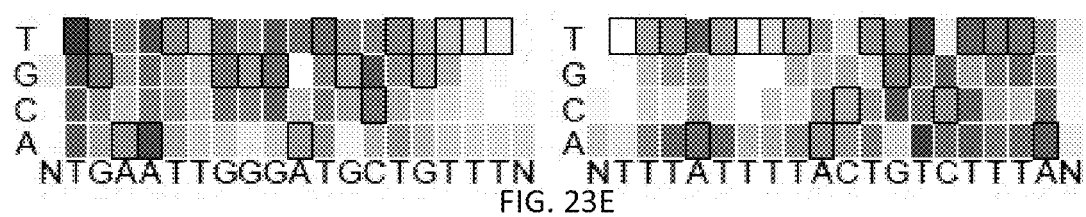
FIG. 23E
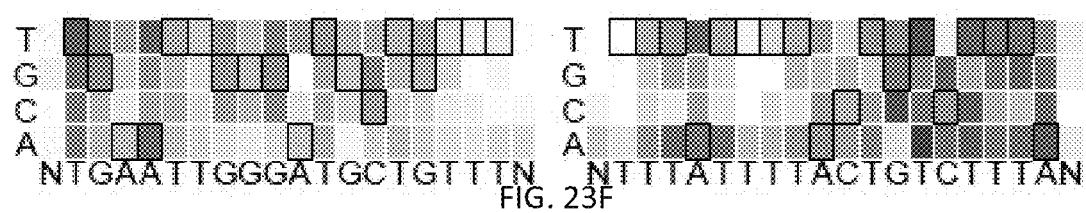
FIG. 23F
Specificity score

SEQUENCE LISTING

```
<160> NUMBER OF SEQ ID NOS: 74

<210> SEQ ID NO 1
<211> LENGTH: 136
<212> TYPE: PRT
<213> ORGANISM: Artificial Sequence
<220> FEATURE:
<223> OTHER INFORMATION: Synthetic Polypeptide

<400> SEQUENCE: 1

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn
    130                 135

<210> SEQ ID NO 2
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
```

```
<222> LOCATION: (16)..(17)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 2

Leu Thr Pro Xaa Gln Val Val Ala Ile Ala Xaa Xaa Xaa Gly Gly Xaa
1               5                   10                  15

Xaa Ala Leu Glu Thr Val Gln Arg Leu Leu Pro Val Leu Cys Gln Xaa
            20                  25                  30

His Gly

<210> SEQ ID NO 3
<211> LENGTH: 63
<212> TYPE: PRT
<213> ORGANISM: Artificial Sequence
<220> FEATURE:
<223> OTHER INFORMATION: Synthetic Polypeptide

<400> SEQUENCE: 3

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Arg Pro Ala
            20                  25                  30

Leu Asp Ala Val Lys Lys Gly Leu Pro His Ala Pro Ala Leu Ile Lys
        35                  40                  45

Arg Thr Asn Arg Arg Ile Pro Glu Arg Thr Ser His Arg Val Ala
    50                  55                  60

<210> SEQ ID NO 4
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 4

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly
            20                  25

<210> SEQ ID NO 5
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 5

Ser Ile Val Ala Gln Leu Ser Arg Pro Asp Pro Ala Leu Ala Ala Leu
1               5                   10                  15

Thr Asn

<210> SEQ ID NO 6
<211> LENGTH: 530
<212> TYPE: PRT
<213> ORGANISM: Artificial Sequence
<220> FEATURE:
<223> OTHER INFORMATION: Synthetic Polypeptide

<400> SEQUENCE: 6
```

```
Leu Thr Pro Asp Gln Val Val Ala Ile Ala Ser Asn Gly Gly Lys
  1               5                  10                 15

Gln Ala Leu Glu Thr Val Gln Arg Leu Leu Pro Val Leu Cys Gln Asp
                 20                 25                  30

His Gly Leu Thr Pro Glu Gln Val Val Ala Ile Ala Ser His Asp Gly
             35                 40                  45

Gly Lys Gln Ala Leu Glu Thr Val Gln Arg Leu Leu Pro Val Leu Cys
 50                  55                  60

Gln Ala His Gly Leu Thr Pro Asp Gln Val Val Ala Ile Ala Ser Asn
 65                  70                  75                  80

Ile Gly Gly Lys Gln Ala Leu Glu Thr Val Gln Arg Leu Leu Pro Val
                 85                  90                  95

Leu Cys Gln Ala His Gly Leu Thr Pro Ala Gln Val Val Ala Ile Ala
                100                 105                 110

Asn Asn Asn Gly Gly Lys Gln Ala Leu Glu Thr Val Gln Arg Leu Leu
            115                 120                 125

Pro Val Leu Cys Gln Asp His Gly Leu Thr Pro Asp Gln Val Val Ala
130                 135                 140

Ile Ala Asn Asn Asn Gly Gly Lys Gln Ala Leu Glu Thr Val Gln Arg
145                 150                 155                 160

Leu Leu Pro Val Leu Cys Gln Asp His Gly Leu Thr Pro Glu Gln Val
                165                 170                 175

Val Ala Ile Ala Ser Asn Ile Gly Gly Lys Gln Ala Leu Glu Thr Val
                180                 185                 190

Gln Arg Leu Leu Pro Val Leu Cys Gln Ala His Gly Leu Thr Pro Asp
            195                 200                 205

Gln Val Val Ala Ile Ala Asn Asn Asn Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Ala Gln Val Val Ala Ile Ala Asn Asn Asn Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Asn Asn Asn Gly Gly Lys
            275                 280                 285

Gln Ala Leu Glu Thr Val Gln Arg Leu Leu Pro Val Leu Cys Gln Asp
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Asp Gln Val Val Ala Ile Ala Ser Asn
                340                 345                 350

Gly Gly Gly Lys Gln Ala Leu Glu Thr Val Gln Arg Leu Leu Pro Val
            355                 360                 365

Leu Cys Gln Ala His Gly Leu Thr Pro Ala Gln Val Val Ala Ile Ala
        370                 375                 380

Ser Asn Gly Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415
```

```
Ile Ala Ser His Asp Gly Gly Lys Gln Ala Leu Glu Thr Val Gln Arg
            420                 425                 430

Leu Leu Pro Val Leu Cys Gln Asp His Gly Leu Thr Pro Glu Gln Val
        435                 440                 445

Val Ala Ile Ala Asn Asn Asn Gly Gly Lys Gln Ala Leu Glu Thr Val
450                 455                 460

Gln Arg Leu Leu Pro Val Leu Cys Gln Ala His Gly Leu Thr Pro Asp
465                 470                 475                 480

Gln Val Val Ala Ile Ala Asn Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Glu Gln Val Val Ala Ile Ala Ser His Asp Gly Gly Arg Pro Ala
        515                 520                 525

Leu Glu
    530

<210> SEQ ID NO 7
<211> LENGTH: 684
<212> TYPE: PRT
<213> ORGANISM: Artificial Sequence
<220> FEATURE:
<223> OTHER INFORMATION: Synthetic Polypeptide

<400> SEQUENCE: 7

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn Leu Thr Pro Asp Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Asp His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Asp
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Ala His Gly Leu Thr
225                 230                 235                 240
```

-continued

Pro Ala Gln Val Val Ala Ile Ala Asn Asn Asn Gly Gly Lys Gln Ala
                245                 250                 255

Leu Glu Thr Val Gln Arg Leu Leu Pro Val Leu Cys Gln Asp His Gly
        260                 265                 270

Leu Thr Pro Asp Gln Val Val Ala Ile Ala Asn Asn Asn Gly Gly Lys
    275                 280                 285

Gln Ala Leu Glu Thr Val Gln Arg Leu Leu Pro Val Leu Cys Gln Asp
290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Asp Gln Val Val Ala Ile Ala Asn Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Ala Gln Val Val Ala Ile Ala
    370                 375                 380

Asn Asn Asn Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
                405                 410                 415

Ile Ala Asn Asn Asn Gly Gly Lys Gln Ala Leu Glu Thr Val Gln Arg
            420                 425                 430

Leu Leu Pro Val Leu Cys Gln Asp His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Asp
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Ala Gln Val Val Ala Ile Ala Ser Asn Gly Gly Gly Lys Gln Ala
        515                 520                 525

Leu Glu Thr Val Gln Arg Leu Leu Pro Val Leu Cys Gln Asp His Gly
    530                 535                 540

Leu Thr Pro Asp Gln Val Val Ala Ile Ala Ser His Asp Gly Gly Lys
545                 550                 555                 560

Gln Ala Leu Glu Thr Val Gln Arg Leu Leu Pro Val Leu Cys Gln Asp
                565                 570                 575

His Gly Leu Thr Pro Glu Gln Val Val Ala Ile Ala Asn Asn Asn Gly
            580                 585                 590

Gly Lys Gln Ala Leu Glu Thr Val Gln Arg Leu Leu Pro Val Leu Cys
        595                 600                 605

Gln Ala His Gly Leu Thr Pro Asp Gln Val Val Ala Ile Ala Asn Asn
    610                 615                 620

Asn Gly Gly Lys Gln Ala Leu Glu Thr Val Gln Arg Leu Leu Pro Val
625                 630                 635                 640

Leu Cys Gln Ala His Gly Leu Thr Pro Glu Gln Val Val Ala Ile Ala
                645                 650                 655

Ser His Asp Gly Gly Arg Pro Ala Leu Glu Ser Ile Val Ala Gln Leu

```
                660              665             670
Ser Arg Pro Asp Pro Ala Leu Ala Ala Leu Thr Asn
            675                 680
```

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 8

```
Gly Gly Gly Gly Ser
1               5
```

<210> SEQ ID NO 9
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 9

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Arg Gly Val Pro
        35
```

<210> SEQ ID NO 10
<211> LENGTH: 90
<212> TYPE: PRT
<213> ORGANISM: Artificial Sequence
<220> FEATURE:
<223> OTHER INFORMATION: Synthetic Polypeptide

<400> SEQUENCE: 10

```
Ala Arg Val Thr Val Gln Asp Ala Val Glu Lys Ile Gly Asn Arg Phe
1               5                   10                  15

Asp Leu Val Leu Val Ala Ala Arg Ala Arg Gln Met Gln Val Gly
            20                  25                  30

Gly Lys Asp Pro Leu Val Pro Glu Glu Asn Asp Lys Thr Thr Val Ile
        35                  40                  45

Ala Leu Arg Glu Ile Glu Glu Gly Leu Ile Asn Asn Gln Ile Leu Asp
    50                  55                  60

Val Arg Glu Arg Gln Glu Gln Glu Gln Glu Ala Ala Glu Leu Gln
65                  70                  75                  80

Ala Val Thr Ala Ile Ala Glu Gly Arg Arg
                85                  90
```

<210> SEQ ID NO 11
<211> LENGTH: 819
<212> TYPE: PRT
<213> ORGANISM: Artificial Sequence
<220> FEATURE:
<223> OTHER INFORMATION: Synthetic Polypeptide

<400> SEQUENCE: 11

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
```

-continued

```
                20                  25                  30
Gly Ile His Arg Gly Val Pro Met Val Asp Leu Arg Thr Leu Gly Tyr
                35                  40                  45
Ser Gln Gln Gln Glu Lys Ile Lys Pro Lys Val Arg Ser Thr Val
    50                  55                  60
Ala Gln His His Glu Ala Leu Val Gly His Gly Phe Thr His Ala His
65                  70                  75                  80
Ile Val Ala Leu Ser Gln His Pro Ala Ala Leu Gly Thr Val Ala Val
                85                  90                  95
Lys Tyr Gln Asp Met Ile Ala Ala Leu Pro Glu Ala Thr His Glu Ala
                100                 105                 110
Ile Val Gly Val Gly Lys Gln Trp Ser Gly Ala Arg Ala Leu Glu Ala
                115                 120                 125
Leu Leu Thr Val Ala Gly Glu Leu Arg Gly Pro Pro Leu Gln Leu Asp
                130                 135                 140
Thr Gly Gln Leu Leu Lys Ile Ala Lys Arg Gly Gly Val Thr Ala Val
145                 150                 155                 160
Glu Ala Val His Ala Trp Arg Asn Ala Leu Thr Gly Ala Pro Leu Asn
                165                 170                 175
Leu Thr Pro Asp Gln Val Val Ala Ile Ala Ser Asn Gly Gly Lys
                180                 185                 190
Gln Ala Leu Glu Thr Val Gln Arg Leu Leu Pro Val Leu Cys Gln Asp
                195                 200                 205
His Gly Leu Thr Pro Glu Gln Val Val Ala Ile Ala Ser His Asp Gly
                210                 215                 220
Gly Lys Gln Ala Leu Glu Thr Val Gln Arg Leu Leu Pro Val Leu Cys
225                 230                 235                 240
Gln Ala His Gly Leu Thr Pro Asp Gln Val Val Ala Ile Ala Ser Asn
                245                 250                 255
Ile Gly Gly Lys Gln Ala Leu Glu Thr Val Gln Arg Leu Leu Pro Val
                260                 265                 270
Leu Cys Gln Ala His Gly Leu Thr Pro Ala Gln Val Val Ala Ile Ala
                275                 280                 285
Asn Asn Asn Gly Gly Lys Gln Ala Leu Glu Thr Val Gln Arg Leu Leu
                290                 295                 300
Pro Val Leu Cys Gln Asp His Gly Leu Thr Pro Asp Gln Val Val Ala
305                 310                 315                 320
Ile Ala Asn Asn Asn Gly Gly Lys Gln Ala Leu Glu Thr Val Gln Arg
                325                 330                 335
Leu Leu Pro Val Leu Cys Gln Asp His Gly Leu Thr Pro Glu Gln Val
                340                 345                 350
Val Ala Ile Ala Ser Asn Ile Gly Gly Lys Gln Ala Leu Glu Thr Val
                355                 360                 365
Gln Arg Leu Leu Pro Val Leu Cys Gln Ala His Gly Leu Thr Pro Asp
                370                 375                 380
Gln Val Val Ala Ile Ala Asn Asn Asn Gly Gly Lys Gln Ala Leu Glu
385                 390                 395                 400
Thr Val Gln Arg Leu Leu Pro Val Leu Cys Gln Ala His Gly Leu Thr
                405                 410                 415
Pro Ala Gln Val Val Ala Ile Ala Asn Asn Asn Gly Gly Lys Gln Ala
                420                 425                 430
Leu Glu Thr Val Gln Arg Leu Leu Pro Val Leu Cys Gln Asp His Gly
                435                 440                 445
```

Leu Thr Pro Asp Gln Val Val Ala Ile Ala Asn Asn Asn Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser Asn
        515                 520                 525

Gly Gly Gly Lys Gln Ala Leu Glu Thr Val Gln Arg Leu Leu Pro Val
    530                 535                 540

Leu Cys Gln Ala His Gly Leu Thr Pro Ala Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Asp His Gly Leu Thr Pro Asp Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Asp His Gly Leu Thr Pro Glu Gln Val
    610                 615                 620

Val Ala Ile Ala Asn Asn Asn Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Asn Asn Asn Gly Gly Lys Gln Ala Leu Glu
            660                 665                 670

Thr Val Gln Arg Leu Leu Pro Val Leu Cys Gln Ala His Gly Leu Thr
        675                 680                 685

Pro Glu Gln Val Val Ala Ile Ala Ser His Asp Gly Gly Arg Pro Ala
    690                 695                 700

Leu Glu Ser Ile Val Ala Gln Leu Ser Arg Pro Asp Pro Ala Leu Ala
705                 710                 715                 720

Ala Leu Thr Asn Gly Gly Gly Ser Ala Arg Val Thr Val Gln Asp
                725                 730                 735

Ala Val Glu Lys Ile Gly Asn Arg Phe Asp Leu Val Leu Val Ala Ala
            740                 745                 750

Arg Arg Ala Arg Gln Met Gln Val Gly Gly Lys Asp Pro Leu Val Pro
        755                 760                 765

Glu Glu Asn Asp Lys Thr Thr Val Ile Ala Leu Arg Glu Ile Glu Glu
    770                 775                 780

Gly Leu Ile Asn Asn Gln Ile Leu Asp Val Arg Glu Arg Gln Glu Gln
785                 790                 795                 800

Gln Glu Gln Glu Ala Ala Glu Leu Gln Ala Val Thr Ala Ile Ala Glu
                805                 810                 815

Gly Arg Arg

<210> SEQ ID NO 12
<211> LENGTH: 564
<212> TYPE: PRT
<213> ORGANISM: Artificial Sequence
<220> FEATURE:
<223> OTHER INFORMATION: Synthetic Polypeptide

```
<400> SEQUENCE: 12

Leu Thr Pro Asp Gln Val Val Ala Ile Ala Asn Asn Asn Gly Gly Lys
1               5                   10                  15

Gln Ala Leu Glu Thr Val Gln Arg Leu Leu Pro Val Leu Cys Gln Asp
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Arg Leu Leu Pro Val Leu Cys
    50                  55                  60

Gln Ala His Gly Leu Thr Pro Asp Gln Val Val Ala Ile Ala Ser Asn
65                  70                  75                  80

Ile Gly Gly Lys Gln Ala Leu Glu Thr Val Gln Arg Leu Leu Pro Val
                85                  90                  95

Leu Cys Gln Ala His Gly Leu Thr Pro Ala Gln Val Val Ala Ile Ala
            100                 105                 110

Ser Asn Gly Gly Lys Gln Ala Leu Glu Thr Val Gln Arg Leu Leu
        115                 120                 125

Pro Val Leu Cys Gln Asp His Gly Leu Thr Pro Asp Gln Val Val Ala
        130                 135                 140

Ile Ala Ser Asn Gly Gly Lys Gln Ala Leu Glu Thr Val Gln Arg
145                 150                 155                 160

Leu Leu Pro Val Leu Cys Gln Asp His Gly Leu Thr Pro Glu Gln Val
                165                 170                 175

Val Ala Ile Ala Asn Asn Asn Gly Gly Lys Gln Ala Leu Glu Thr Val
            180                 185                 190

Gln Arg Leu Leu Pro Val Leu Cys Gln Ala His Gly Leu Thr Pro Asp
        195                 200                 205

Gln Val Val Ala Ile Ala Asn Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Ala Gln Val Val Ala Ile Ala Asn Asn Asn Gly Gly Lys Gln Ala
                245                 250                 255

Leu Glu Thr Val Gln Arg Leu Leu Pro Val Leu Cys Gln Asp His Gly
            260                 265                 270

Leu Thr Pro Asp Gln Val Val Ala Ile Ala Ser Asn Ile Gly Gly Lys
        275                 280                 285

Gln Ala Leu Glu Thr Val Gln Arg Leu Leu Pro Val Leu Cys Gln Asp
    290                 295                 300

His Gly Leu Thr Pro Glu Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Asp Gln Val Val Ala Ile Ala Asn Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Ala Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Asp His Gly Leu Thr Pro Asp Gln Val Val Ala
```

```
                        405                 410                 415
Ile Ala Ser Asn Gly Gly Gly Lys Gln Ala Leu Glu Thr Val Gln Arg
                420                 425                 430

Leu Leu Pro Val Leu Cys Gln Asp His Gly Leu Thr Pro Glu Gln Val
            435                 440                 445

Val Ala Ile Ala Asn Asn Gly Gly Lys Gln Ala Leu Glu Thr Val
        450                 455                 460

Gln Arg Leu Leu Pro Val Leu Cys Gln Ala His Gly Leu Thr Pro Asp
465                 470                 475                 480

Gln Val Val Ala Ile Ala Ser Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Ala Gln Val Val Ala Ile Ala Ser Asn Gly Gly Lys Gln Ala
        515                 520                 525

Leu Glu Thr Val Gln Arg Leu Leu Pro Val Leu Cys Gln Asp His Gly
    530                 535                 540

Leu Thr Pro Glu Gln Val Val Ala Ile Ala Ser Asn Gly Gly Gly Arg
545                 550                 555                 560

Pro Ala Leu Glu

<210> SEQ ID NO 13
<211> LENGTH: 853
<212> TYPE: PRT
<213> ORGANISM: Artificial Sequence
<220> FEATURE:
<223> OTHER INFORMATION: Synthetic Polypeptide

<400> SEQUENCE: 13

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Asn Asn Asn Gly Gly Lys
            180                 185                 190

Gln Ala Leu Glu Thr Val Gln Arg Leu Leu Pro Val Leu Cys Gln Asp
        195                 200                 205
```

His Gly Leu Thr Pro Glu Gln Val Val Ala Ile Ala Ser Asn Ile Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
            245                 250                 255

Ile Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
        275                 280                 285

Ser Asn Gly Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser Asn Gly Gly Gly Lys Gln Ala Leu Glu Thr Val Gln Arg
            325                 330                 335

Leu Leu Pro Val Leu Cys Gln Asp His Gly Leu Thr Pro Glu Gln Val
            340                 345                 350

Val Ala Ile Ala Asn Asn Asn Gly Gly Lys Gln Ala Leu Glu Thr Val
        355                 360                 365

Gln Arg Leu Leu Pro Val Leu Cys Gln Ala His Gly Leu Thr Pro Asp
    370                 375                 380

Gln Val Val Ala Ile Ala Asn Asn Asn Gly Gly Lys Gln Ala Leu Glu
385                 390                 395                 400

Thr Val Gln Arg Leu Leu Pro Val Leu Cys Gln Ala His Gly Leu Thr
            405                 410                 415

Pro Ala Gln Val Val Ala Ile Ala Asn Asn Asn Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser Asn Ile Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser Asn Gly Gly
            485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Asn Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Ala Gln Val Val Ala Ile Ala
545                 550                 555                 560

Ser His Asp Gly Gly Lys Gln Ala Leu Glu Thr Val Gln Arg Leu Leu
            565                 570                 575

Pro Val Leu Cys Gln Asp His Gly Leu Thr Pro Asp Gln Val Val Ala
            580                 585                 590

Ile Ala Ser Asn Gly Gly Gly Lys Gln Ala Leu Glu Thr Val Gln Arg
        595                 600                 605

Leu Leu Pro Val Leu Cys Gln Asp His Gly Leu Thr Pro Glu Gln Val
    610                 615                 620

```
Val Ala Ile Ala Asn Asn Gly Gly Lys Gln Ala Leu Glu Thr Val
625                 630                 635                 640

Gln Arg Leu Leu Pro Val Leu Cys Gln Ala His Gly Leu Thr Pro Asp
        645                 650                 655

Gln Val Val Ala Ile Ala Ser Asn Gly Gly Lys Gln Ala Leu Glu
            660                 665                 670

Thr Val Gln Arg Leu Leu Pro Val Leu Cys Gln Ala His Gly Leu Thr
        675                 680                 685

Pro Ala Gln Val Val Ala Ile Ala Ser Asn Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Glu Gln Val Val Ala Ile Ala Ser Asn Gly Gly Gly Arg
                725                 730                 735

Pro Ala Leu Glu Ser Ile Val Ala Gln Leu Ser Arg Pro Asp Pro Ala
                740                 745                 750

Leu Ala Ala Leu Thr Asn Gly Gly Gly Ser Ala Arg Val Thr Val
    755                 760                 765

Gln Asp Val Val Glu Lys Ile Gly Asn Arg Phe Asp Leu Val Leu Val
770                 775                 780

Ala Ala Arg Arg Ala Arg Gln Met Gln Val Gly Gly Lys Asp Pro Leu
785                 790                 795                 800

Val Pro Glu Glu Asn Asp Lys Thr Thr Val Ile Ala Leu Arg Glu Ile
                805                 810                 815

Glu Glu Gly Leu Ile Asn Asn Gln Ile Leu Asp Val Arg Glu Arg Gln
                820                 825                 830

Glu Gln Gln Glu Gln Glu Ala Ala Glu Leu Gln Ala Val Thr Ala Ile
                835                 840                 845

Ala Glu Gly Arg Arg
        850

<210> SEQ ID NO 14
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 14

Gly Ser Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
                20                  25                  30

Ile Ala Arg Asn Ser Thr Gln Asp Arg Ile Leu Glu Met Lys Val Met
            35                  40                  45

Glu Phe Phe Met Lys Val Tyr Gly Tyr Arg Gly Lys His Leu Gly Gly
50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Gln Arg Tyr Val Glu Glu Asn Gln
                100                 105                 110

Thr Arg Asn Lys His Ile Asn Pro Asn Glu Trp Trp Lys Val Tyr Pro
            115                 120                 125
```

Ser Ser Val Thr Glu Phe Lys Phe Leu Phe Val Ser Gly His Phe Lys
    130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
        195

<210> SEQ ID NO 15
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 15
tgaattggga tgctgttt                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 16
tttattttac tgtcttta                                                 18

<210> SEQ ID NO 17
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 17
tgaataggaa atatattt                                                 18

<210> SEQ ID NO 18
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 18
tttattttac tgttttta                                                 18

<210> SEQ ID NO 19
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 19
tgaattgaga gaagcatt                                                 18

<210> SEQ ID NO 20
<211> LENGTH: 18
<212> TYPE: DNA

```
<213> ORGANISM: Artificial Sequence
<220> FEATURE:
<223> OTHER INFORMATION: Synthetic Polynucleotide

<400> SEQUENCE: 20
tttattttat tatttta                                                    18

<210> SEQ ID NO 21
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 21
ggaaatggga tactgagt                                                   18

<210> SEQ ID NO 22
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 22
tttatgttac tatttcta                                                   18

<210> SEQ ID NO 23
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 23
tagattgaaa tgctgttt                                                   18

<210> SEQ ID NO 24
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 24
tttttattat tattttta                                                   18

<210> SEQ ID NO 25
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 25
ttaggtattc tattcaaa                                                   18

<210> SEQ ID NO 26
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 26
ggagttcaga cgtgtgctct tccgatctag cgcctgattc gagatcct                  48
```

<210> SEQ ID NO 27
<211> LENGTH: 58
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t

<400> SEQUENCE: 27
cactctttcc ctacacgacg ctcttccgat ctnnnnatgc caaattcata tgcaaggc          58

<210> SEQ ID NO 28
<211> LENGTH: 49
<212> TYPE: DNA
<213> ORGANISM: Artificial Sequence
<220> FEATURE:
<223> OTHER INFORMATION: Synthetic Polypeptide

<400> SEQUENCE: 28
ggagttcaga cgtgtgctct tccgatctcc tgccattgaa ttccagcct                    49

<210> SEQ ID NO 29
<211> LENGTH: 56
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t

<400> SEQUENCE: 29
cactctttcc ctacacgacg ctcttccgat ctnnnntgtc tgcctttcct gtcccc            56

<210> SEQ ID NO 30
<211> LENGTH: 56
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t

<400> SEQUENCE: 30
cactctttcc ctacacgacg ctcttccgat ctnnnntcag aatacctccc cgccag            56

<210> SEQ ID NO 31
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 31
ggagttcaga cgtgtgctct tccgatctgg tggaacaatc cacctgtatt agc               53

<210> SEQ ID NO 32
<211> LENGTH: 56
<212> TYPE: DNA
<213> ORGANISM: Artificial Sequence
<220> FEATURE:

<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t

<400> SEQUENCE: 32
cactctttcc ctacacgacg ctcttccgat ctnnnngaat gtgacaccac caccgc        56

<210> SEQ ID NO 33
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 33
ggagttcaga cgtgtgctct tccgatcttg tttagtaatt aagaccctgg ctttc         55

<210> SEQ ID NO 34
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t

<400> SEQUENCE: 34
cactctttcc ctacacgacg ctcttccgat ctnnnngcga caggtacaaa gcagtccat     59

<210> SEQ ID NO 35
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 35
tgaattggga tgctgttttt aggtattcta ttcaaattta ttttactgtc ttta          54

<210> SEQ ID NO 36
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 36
ttcaggaggg cttcggc                                                   17

<210> SEQ ID NO 37
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 37
atcaggaggg cttcggc                                                   17

<210> SEQ ID NO 38
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 38
ctcaggaggg cttcggc                                                        17

<210> SEQ ID NO 39
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 39
gtcaggaggg cttcggc                                                        17

<210> SEQ ID NO 40
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 40
ttcataaggg attaggc                                                        17

<210> SEQ ID NO 41
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 41
atcataaggg attaggc                                                        17

<210> SEQ ID NO 42
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 42
ctcataaggg attaggc                                                        17

<210> SEQ ID NO 43
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 43
gtcataaggg attaggc                                                        17

<210> SEQ ID NO 44
<211> LENGTH: 573
<212> TYPE: DNA
<213> ORGANISM: Artificial Sequence
<220> FEATURE:
<223> OTHER INFORMATION: Synthetic Polynucleotide

<400> SEQUENCE: 44
atggcacgcg taactgttca ggacgctgta gagaaaattg gtaaccgttt tgacctggta         60

```
ctggtcgccg cgcgtcgcgc tcgtcagatg caggtaggcg aaaggatcc gctggtaccg      120 gaagaaaacg ataaaaccac tgtaatcgcg ctgcgcgaaa tcgaagaagg tctgatcaac      180
aaccagatcc tcgacgttcg cgaacgccag gaacagcaag agcaggaagc cgctgaatta      240
caagccgtta ccgctattgc tgaaggtcgt cgtgcggcgg cggcggcgg cagcaccgcg       300 gcggctgaac gcccatatgc ttgccctgtc gagtcctgcg atcgccgctt ttctcgctcg      360
gatgagctta cccgccatat ccgcatccac acaggccaga agcccttcca gtgtcgaatc      420
tgcatgcgta acttcagtcg tagtgaccac cttaccaccc acatccgcac ccacacaggc      480
gagaagcctt ttgcctgtga catttgtggg aggaagtttg ccaggagtga tgaacgcaag      540
aggcatacca aaatccattt aagacagaag taa                                   573
```

<210> SEQ ID NO 45
<211> LENGTH: 190
<212> TYPE: PRT
<213> ORGANISM: Artificial Sequence
<220> FEATURE:
<223> OTHER INFORMATION: Synthetic Polypeptide

<400> SEQUENCE: 45

```
Met Ala Arg Val Thr Val Gln Asp Ala Val Glu Lys Ile Gly Asn Arg
1               5                   10                  15

Phe Asp Leu Val Leu Val Ala Ala Arg Arg Ala Arg Gln Met Gln Val
            20                  25                  30

Gly Gly Lys Asp Pro Leu Val Pro Glu Glu Asn Asp Lys Thr Thr Val
        35                  40                  45

Ile Ala Leu Arg Glu Ile Glu Glu Gly Leu Ile Asn Asn Gln Ile Leu
    50                  55                  60

Asp Val Arg Glu Arg Gln Glu Gln Gln Glu Gln Glu Ala Ala Glu Leu
65                  70                  75                  80

Gln Ala Val Thr Ala Ile Ala Glu Gly Arg Arg Ala Ala Gly Gly Gly
                85                  90                  95

Gly Ser Thr Ala Ala Ala Glu Arg Pro Tyr Ala Cys Pro Val Glu Ser
            100                 105                 110

Cys Asp Arg Arg Phe Ser Arg Ser Asp Glu Leu Thr Arg His Ile Arg
        115                 120                 125

Ile His Thr Gly Gln Lys Pro Phe Gln Cys Arg Ile Cys Met Arg Asn
    130                 135                 140

Phe Ser Arg Ser Asp His Leu Thr Thr His Ile Arg Thr His Thr Gly
145                 150                 155                 160

Glu Lys Pro Phe Ala Cys Asp Ile Cys Gly Arg Lys Phe Ala Arg Ser
                165                 170                 175

Asp Glu Arg Lys Arg His Thr Lys Ile His Leu Arg Gln Lys
            180                 185                 190
```

<210> SEQ ID NO 46
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 46

```
gaaaatattg ttgatgcgct ggcagtgttc                                        30
```

<210> SEQ ID NO 47
<211> LENGTH: 31

```
<212> TYPE: DNA
<213> ORGANISM: Artificial Sequence
<220> FEATURE:
<223> OTHER INFORMATION: Synthetic Polynucleotide

<400> SEQUENCE: 47
tagcagcctt tacagagaga ataacataaa a                                    31

<210> SEQ ID NO 48
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 48 gcgtgggcg                                                              9

<210> SEQ ID NO 49
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 49 gcgttagcg                                                              9

<210> SEQ ID NO 50
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 50
ntgaattggg atgctgtttn                                                 20

<210> SEQ ID NO 51
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 51
ntttatttta ctgtctttan                                                 20

<210> SEQ ID NO 52
<211> LENGTH: 11
<212> TYPE: DNA
<213> ORGANISM: Artificial Sequence
<220> FEATURE:
```

<223> OTHER INFORMATION: Synthetic Polynucleotide

<400> SEQUENCE: 52
aaatsgggga a                                                             11

<210> SEQ ID NO 53
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 53
aaggggsggg gsggggstaa a                                                  21

<210> SEQ ID NO 54
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 54
gatgagctta cccgccatat ccgcatc                                            27

<210> SEQ ID NO 55
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 55
gatgagctta ccgtacatat ccgcatc                                            27

<210> SEQ ID NO 56
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 56
gatgagctta ccagacatat ccgcatc                                            27

<210> SEQ ID NO 57
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 57

Asp Glu Leu Thr Arg His Ile Arg Ile
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 58

Asp Glu Leu Thr Val His Ile Arg Ile
1               5

```
<210> SEQ ID NO 59
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 59
tcttccagaa ttgatact                                                 18

<210> SEQ ID NO 60
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 60
tctcccagag ttgctcct                                                 18

<210> SEQ ID NO 61
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 61
tattccagga tagatacc                                                 18

<210> SEQ ID NO 62
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 62
tcttccagaa aggatatc                                                 18

<210> SEQ ID NO 63
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 63

Asp Tyr Lys Asp Asp Asp Asp Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 64

Pro Lys Lys Lys Arg Lys Val
1               5

<210> SEQ ID NO 65
<211> LENGTH: 154
<212> TYPE: DNA
```

<213> ORGANISM: E. coli

<400> SEQUENCE: 65

```
cacttgttag tgtaattcgc taactcatcc tggcatgttg ctgttgattc ttcaatcaga    60
tctttataaa tcaaaaagat aaaaaattgg cacgcaaatt gtattaacag ttcagcagga   120
caatcctgaa cgcagaaatc aagaggacaa catt                               154
```

<210> SEQ ID NO 66
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa is Thr or Ala
<220> FEATURE:
<221> NAME/KEY: misc_feature
<222> LOCATION: (3)..(3)
<223> OTHER INFORMATION: Xaa is Pro or Leu
<220> FEATURE:
<221> NAME/KEY: misc_feature
<222> LOCATION: (4)..(4)
<223> OTHER INFORMATION: Xaa is Asp, Glu, Ala, Lys, or Asn
<220> FEATURE:
<221> NAME/KEY: misc_feature
<222> LOCATION: (8)..(8)
<223> OTHER INFORMATION: Xaa is Ala or Gly
<220> FEATURE:
<221> NAME/KEY: misc_feature
<222> LOCATION: (11)..(11)
<223> OTHER INFORMATION: Xaa is Ser, Asn, or Lys
<220> FEATURE:
<221> NAME/KEY: misc_feature
<222> LOCATION: (12)..(12)
<223> OTHER INFORMATION: Xaa is Asn or His
<220> FEATURE:
<221> NAME/KEY: misc_feature
<222> LOCATION: (13)..(13)
<223> OTHER INFORMATION: Xaa is Asn, Gly, His, or Lys
<220> FEATURE:
<221> NAME/KEY: misc_feature
<222> LOCATION: (15)..(15)
<223> OTHER INFORMATION: Xaa is Gly or Ser
<220> FEATURE:
<221> NAME/KEY: misc_feature
<222> LOCATION: (16)..(16)
<223> OTHER INFORMATION: Xaa is Lys or Arg
<220> FEATURE:
<221> NAME/KEY: misc_feature
<222> LOCATION: (17)..(17)
<223> OTHER INFORMATION: Xaa is Gln or Pro
<220> FEATURE:
<221> NAME/KEY: misc_feature
<222> LOCATION: (18)..(18)
<223> OTHER INFORMATION: Xaa is Ala or Gly
<220> FEATURE:
<221> NAME/KEY: misc_feature
<222> LOCATION: (20)..(20)
<223> OTHER INFORMATION: Xaa is Glu or Gly
<220> FEATURE:
<221> NAME/KEY: misc_feature
<222> LOCATION: (21)..(21)
<223> OTHER INFORMATION: Xaa is Thr or Ala
<220> FEATURE:
<221> NAME/KEY: misc_feature
<222> LOCATION: (23)..(23)
<223> OTHER INFORMATION: Xaa is Gln or Lys
<220> FEATURE:
<221> NAME/KEY: misc_feature
<222> LOCATION: (26)..(26)
<223> OTHER INFORMATION: Xaa is Leu, Phe, or Ala
<220> FEATURE:
<221> NAME/KEY: misc_feature
<222> LOCATION: (32)..(32)
<223> OTHER INFORMATION: Xaa is Asp, Ala, or Ser
<220> FEATURE:
<221> NAME/KEY: misc_feature
<222> LOCATION: (33)..(33)
<223> OTHER INFORMATION: Xaa is His, Pro, or Tyr
<220> FEATURE:
<221> NAME/KEY: misc_feature
<222> LOCATION: (34)..(34)
<223> OTHER INFORMATION: Xaa is Gly or Ser

<400> SEQUENCE: 66

Leu Xaa Xaa Xaa Gln Val Val Xaa Ile Ala Xaa Xaa Xaa Gly Xaa Xaa
1               5                   10                  15

Xaa Xaa Leu Xaa Xaa Val Xaa Thr Leu Xaa Pro Val Leu Cys Glx Xaa
            20                  25                  30

Xaa Xaa

<210> SEQ ID NO 67
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 67
ggaaatggga tactgttt                                              18

<210> SEQ ID NO 68
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 68
tgaattggga tactgatt                                              18

<210> SEQ ID NO 69
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 69
tgaaatggga tactgttt                                              18

<210> SEQ ID NO 70
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 70
ggaaatggga tgctgttt                                              18

<210> SEQ ID NO 71
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 71

```
tgaattggga tgctgagt                                                      18

<210> SEQ ID NO 72
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 72
tgaattggga tactgtgt                                                      18

<210> SEQ ID NO 73
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 73
tgaattggga tgctgtgt                                                      18

<210> SEQ ID NO 74
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 74
ggaattggga tgctgtgt                                                      18
```

EVOLUTION OF TALENS

RELATED APPLICATIONS

This application is a national stage filing under 35 U.S.C. § 371 of international PCT application, PCT/US2016/044546, filed Jul. 28, 2016, which claims priority under 35 U.S.C. § 119(e) to U.S. Provisional Application, U.S. Ser. No. 62/198,906, filed on Jul. 30, 2015, each of which is incorporated herein by reference.

GOVERNMENT SUPPORT

This invention was made with government support under HR0011-11-2-0003 awarded by the Department of Defense. The government has certain rights in the invention.

BACKGROUND

Genome-editing tools have the potential to revolutionize our understanding of how genotype influences phenotype, facilitate the development of organisms of industrial and biomedical relevance, and serve as treatments for genetic diseases[1,2]. These tools include meganucleases[3,4], site-specific recombinases, RNA-guided nucleases such as Cas9[6], and fusions of programmable DNA-binding domains (DBDs) such as zinc fingers to effector domains including nucleases, recombinases, and transposases[4,7]. Zinc fingers (ZFs) are naturally occurring DBDs of approximately 30 amino acids that typically bind three bases of DNA along the major groove[7-9]. Several methods have been developed to generate zinc-finger arrays with tailor-made DNA specificities[10-12].

Transcription activator-like effectors (TALEs), have emerged as attractive alternatives to zinc fingers for sequence-specific DNA targeting[7]. TALEs consist of an N-terminal domain followed by a series of tandem repeats each of 33 to 35 amino acids, a nuclear localization sequence, a transcription activation domain, and a C-terminal domain[13,14]. Two repeat variable diresidues (RVDs), typically at positions 12 and 13 within each repeat, recognize and bind to a specific DNA base[15,16]. Altering the RVDs allows TALE repeats to be programmed using a simple code[13,17]. Unlike ZFs, TALE arrays are thought to bind DNA in a fairly context-independent manner facilitating the design and assembly of arrays to target long sequences[7,18,19]. TALEs have been fused to various effector domains to generate site-specific DNA-cleaving enzymes (TALENs)[7,20,21], epigenome-modification enzymes, and transcriptional activators and repressors[14,17,24,25].

SUMMARY OF THE INVENTION

One limitation of TALEs is that the 5' nucleotide of the target sequence is specified to be T[15,26,27]. TALE domains with alternative 5' nucleotide specificities could expand the scope of DNA target sequences that can be bound by TALEs. Although promiscuous TALEs with no specificity at the 5' position have been described[28,29], no TALE variants that preferentially recognize 5' A or 5' C have been reported. In addition, the DNA sequence specificity of DBDs is a crucial determinant of their safety and usefulness as research tools and human therapeutics. While TALEN architectures were previously engineered with improved general DNA-cleaving specificity by reducing excess non-specific DNA-binding[30], enhancing the specificity of a particular TALE array in a targeted manner by decreasing its ability to bind to specific off-target DNA sequences found in a genome has not been accomplished.

Some aspects of the instant disclosure are based, at least in part, on the surprising discovery that TALE mutants that preferentially bind a non-canonical 5' nucleotide (A, C, or G) over the native 5' T can be evolved using phage-assisted continuous evolution (PACE), thereby expanding the scope of DNA target sequences that can be bound by TALEs. Modified TALE proteins that bind a target site with a non-canonical 5' adenine (A), cytosine (C) or guanine (G) and methods of using such modified TALE proteins are described herein.

Some aspects of the instant disclosure are based, at least in part, on the surprising discovery that PACE can be used to increase the specificity of an ATM-targeting TALE to its target site relative to known off-target sites. Accordingly, described herein are modified ATM-targeting TALE proteins that preferentially bind to an ATM target site relative to an off-target site and methods of using such ATM-targeting TALE proteins.

Some aspects of this disclosure provide modified TALE domains.

For example, some aspects of this disclosure provide proteins comprising an amino acid sequence that is at least 80% identical to the amino acid sequence provided in SEQ ID NO: 1, wherein the amino acid sequence comprises an alanine to glutamic acid amino acid substitution at amino acid residue 39 (A39E) of SEQ ID NO: 1 or a homologous residue in a canonical N-terminal TALE domain, and/or a lysine to glutamic acid substitution at amino acid residue 19 (K19E) of SEQ ID NO:1 or a homologous residue in a canonical N-terminal TALE domain.

Some aspects of this disclosure provide proteins comprising an amino acid sequence that is at least 80% identical to the amino acid sequence LTPX$_1$QVVAIAX$_2$X$_3$X$_4$GGX$_5$X$_6$ALETVQRLLPVL-CQX$_7$HG (SEQ ID NO: 2), wherein X$_1$ is D, E or A, wherein X$_2$ is S or N, wherein X$_3$ is N or H, wherein X$_4$ is G, D, I, or N, wherein X$_5$ is K or R, wherein X$_6$ is Q or P, wherein X$_7$ is D or A, and wherein the amino acid sequence comprises one or more amino acid substitutions selected from the group consisting of T2A, P3L, P3S, X$_1$4G, X$_1$4K, X$_1$4N, X$_2$11K, X$_2$11Y, X$_3$12H, X$_4$13K, X$_4$13H, G15S, X$_5$16R, X$_6$17P, T21A, L26F, P27S, V28G, Q31K, X$_7$32S, D32E, and H33L.

Some aspects of this disclosure provide proteins comprising an amino acid sequence that is at least 80% identical to the amino acid sequence provided in SEQ ID NO: 3, 4, or 5, wherein the amino acid sequence comprises a glutamine to proline amino acid substitution at amino acid residue 5 (Q5P) as compared to either SEQ ID NO: 3, 4, or 5, or a homologous residue in a canonical C-terminal TALE domain.

Some aspects of this disclosure provide proteins comprising the structure [N-terminal domain]-[TALE repeat array]-[C-terminal domain]; wherein the N-terminal domain comprises an N-terminal domain provided herein, the TALE repeat array comprises a TALE repeat array provided herein, and/or the C-terminal domain comprises a C-terminal domain provided herein.

Some aspects of this disclosure provide proteins comprising an amino acid sequence that is at least 80% identical to the amino acid sequence provided in SEQ ID NO: 12, wherein the amino acid sequence comprises one or more amino acid substitutions selected from the group consisting of A76T, K84R, D134E, L162S, A222S, K288R, Q329K, R330K, A338T, A392V, A416V, P435Q, V464I, L468F, and K512R.

Some aspects of this disclosure provide proteins comprising an amino acid sequence that is at least 80% identical to the amino acid sequence provided in SEQ ID NO: 1, wherein the amino acid sequence comprises one or more amino acid substitutions selected from the group consisting of Q13R, A25E, W126C, and G132R, or a homologous residue in a canonical N-terminal TALE domain.

Some aspects of this disclosure provide proteins comprising an amino acid sequence that is at least 80% identical to the amino acid sequence provided in SEQ ID NO: 13, wherein the amino acid sequence comprises amino acid substitutions (a) Q53R and A252T; (b) W166C, K260R, A398S, A514T, A592V, and Q745P; (c) A252T, Q505K, and Q745P; or (d) A252T, L338S, Q505K, and Q745P.

Some aspects of this disclosure provide methods comprising contacting a nucleic acid molecule comprising a target sequence with (a) a protein comprising a modified TALE domain, a modified TALE repeat array, or a modified TALE protein as provided herein.

Some aspects of this disclosure provide methods of phage-assisted, continuous evolution of a DNA binding domain, wherein the methods comprise (a) contacting a flow of host cells through a lagoon with a selection phage comprising a nucleic acid sequence encoding a DNA-binding domain to be evolved, and (b) incubating the selection phage or phagemid in the flow of host cells under conditions suitable for the selection phage to replicate and propagate within the flow of host cells, and for the nucleic acid sequence encoding the DNA-binding domain to be evolved to mutate; wherein the host cells are introduced through the lagoon at a flow rate that is faster than the replication rate of the host cells and slower than the replication rate of the phage, thereby permitting replication and propagation of the selection phage in the lagoon; and wherein the flow of host cells comprises a plurality of host cells harboring a positive selection construct comprising a nucleic acid sequence encoding a gene product essential for the generation of infectious phage particles, wherein the gene product essential for the generation of infectious phage particles is expressed in response to a desired DNA-binding activity of the DNA-binding domain to be evolved or an evolution product thereof, wherein the selection phage does not comprise a nucleic acid sequence encoding the gene product essential for the generation of infectious phage particles; and wherein the flow of host cells comprises a plurality of host cells harboring a negative selection construct comprising a nucleic acid sequence encoding a dominant negative gene product that decreases or abolishes the production of infectious phage particles, wherein the dominant negative gene product is expressed in response to an undesired activity of the DNA-binding domain to be evolved or an evolution product thereof.

Some aspects of this disclosure provide methods of improving the specificity of a DNA-binding domain by phage-assisted, continuous evolution, wherein the methods comprise (a) contacting a flow of host cells through a lagoon with a selection phage comprising a nucleic acid sequence encoding a DNA-binding domain to be evolved, and (b) incubating the selection phage or phagemid in the flow of host cells under conditions suitable for the selection phage to replicate and propagate within the flow of host cells, and for the nucleic acid sequence encoding the DNA-binding domain to be evolved to mutate; wherein the host cells are introduced through the lagoon at a flow rate that is faster than the replication rate of the host cells and slower than the replication rate of the phage, thereby permitting replication and propagation of the selection phage in the lagoon; and wherein the flow of host cells comprises a plurality of host cells harboring a negative selection construct comprising a nucleic acid sequence encoding a dominant negative gene product that decreases or abolishes the production of infectious phage particles, wherein the dominant negative gene product is expressed in response to an undesired activity of the DNA-binding domain to be evolved or an evolution product thereof.

The details of one or more embodiments of the present disclosure are set forth in the accompanying Figures. Other features, objects, and advantages of the disclosure will be apparent from the Detailed Description, the Examples, and from the claims.

BRIEF DESCRIPTION OF THE DRAWINGS

FIG. 1A shows an overview of phage-assisted continuous evolution (PACE). FIG. 1B shows a reporter system used to couple DNA binding to induction of gene III-luciferase expression. FIG. 1C shows the luciferase activity resulting from ATc-induced Zif268 protein binding to either its on-target sequence (5'-GCGTGGGCG-'3; SEQ ID NO: 48) or an off-target sequence (5'-GCGTTAGCG-'3; SEQ ID NO: 49). FIG. 1D shows the luciferase activity resulting from ATc-induced TALE protein binding to either its on-target sequence (CBX8: 5'-TTCAGGAGGGCTTCGGC-3', SEQ ID NO: 36) or an off-target sequence (5'-TTCATAAGGGATT-AGGC-3', SEQ ID NO: 40). Bar graphs in FIGS. 1C and 1D represent mean+s.d. (n=3).

FIG. 2A shows the CBX8-targeting TALE-ω fusion and the relationship between individual repeats and target sequence nucleotides. The sequences correspond to SEQ ID NOs: 36-39. FIG. 2B shows the luciferase activity shown as fold induction from TALE induction (relative to controls lacking induction of TALE expression) for the canonical TALE and five evolved clones from either lagoon 1 (L1) or lagoon 2 (L2) using a CBX8 target sequence variant beginning with 5' A (left). The right panel of FIG. 2B also shows mutations in the evolved proteins shown in the left panel. Blue squares indicate mutations within the TALE domain, and green squares indicate mutations within the ω subunit. FIG. 2C shows the reporter system used to couple DNA binding to an off-target sequence to production of pIII-neg-YFP. The left panel of FIG. 2D shows YFP fluorescence represented as fold induction upon induction of TALE expression, for the canonical TALE and two evolved clones from either L1 or L2 using CBX8-target sequences beginning with 5' A, 5' C, 5' G, or 5' T. The right panel of FIG. 2D shows the mutations in the evolved proteins shown in the left panel. Bar graphs in FIGS. 2B and 2D represent mean+s.d. (n=3).

FIG. 3A shows a schematic of the ATM targeting TALE-ω fusion and the relationship between individual TALE repeats and the nucleotides they recognize for the on-target sequence (ATM: 5'-TGAATTGGGATGCT-GTTT-3' (SEQ ID NO: 15)), or the most highly cleaved human genomic off-target sequence (OffA17: 5'-GGAAATGGGATACTGAGT-3' (SEQ ID NO: 21)). The left panel of FIG. 3B shows the relative cleavage efficiencies of the canonical ATM TALEN pair or four ATM TALEN pairs containing the canonical ATM-right half site TALEN and an evolved ATM-left half site TALEN (L1-2, L2-1, L3-1, or L3-2) on a linear 6-kb DNA fragment containing either the ATM on-target sequence or the OffA17 off-target sequence. The top band is non-cleaved DNA, while the bottom band is a cleavage product. Cleavage percentages were determined using densitometry analysis (GelEval), and are included below each lane. The right panel of FIG. 3B shows mutations in the evolved ATM-left half site TALEs used in the left panel.

FIGS. 4A-4D show high-throughput specificity profiling of canonical and evolved TALENs. In FIGS. 4A and 4B, the top panels are heat maps showing specificity scores for either canonical (FIG. 4A) or L3-1 (FIG. 4B) evolved TALENs targeting the ATM locus at each position in the left and right half-sites plus a single flanking position (N). In FIGS. 4A and 4B, the bottom panels are bar graphs showing the quantitative specificity score for each nucleotide position. A score of zero indicates no specificity, while a score of 1.0 corresponds to perfect specificity. The sequences in FIG. 4A correspond to SEQ ID NO: 50 (left) and SEQ ID NO: 51 (right). The sequences in FIG. 4B correspond to SEQ ID NO: 50 (left) and SEQ ID NO: 51 (right). FIG. 4C is a bar graph indicating the quantitative difference in specificity score at each position between the canonical and L3-1 evolved TALENs ($score_{L3-1}$-$score_{canonical}$) at each position in the target half-sites plus a single flanking position (N). A score of zero indicates no change in specificity. The sequences in FIG. 4C correspond to SEQ ID NO: 15 (left) and SEQ ID NO: 16 (right). For all heat maps, the cognate base for each position in the target sequence is boxed. For the right half-site, data for the sense strand are displayed. FIG. 4D is identical to FIG. 4C, except for the L3-2 evolved TALEN versus the canonical TALEN. The sequences in FIG. 4D correspond to SEQ ID NO: 15 (left) and SEQ ID NO: 16 (right).

FIG. 6A shows a comparison of phage-shock promoter response between S1030 and S1632 cells. Upon phage infection, activation of a phage shock promoter (PSP) induces bacterial luciferase expression, and can be measured as an increase in luminescence. The phage shock response sensors pspBC were deleted from S1632 cells, resulting in no transcriptional activation in the absence or presence of infecting phage. FIG. 6B shows that the over-expression of pspBC from an arabinose-controlled promoter ($P_{BAD}$) results in activation of the PSP in a manner independent of phage infection, eliminating variability in transcriptional activation of the promoter. Data represent mean±s.d. (n=3).

FIG. 7A shows the luminescence signal in the presence or absence of 20 μM arabinose from wild-type and mutant PSP promoters. All readings were normalized to wild-type PSP, which was set to 1. Data represent mean±s.d. (n=3). FIGS. 7B-7C present a summary of activity, background levels, and genotypes of mutant promoters assayed in FIG. 7A. Background levels of all mutant promoters are listed relative to wild-type (SEQ ID NO: 65).

FIG. 8A shows the luminescence resulting from induction of a bacterial luciferase (luxAB) cassette driven by the $P_{lux}$ promoter in response to the indicated doses of N-(3-oxohexanoyl)-1-homoserine lactone (OHHL) (the LuxR transcriptional regulator is also controlled by the $P_{lux}$ promoter, only in the opposite direction). Data represent mean±s.d. (n=3). FIG. 8B shows the kinetic analysis of OHHL-mediated expression of GroESL (cassette: luxR-$P_{lux}$-groESL) on the folding of LuxAB (cassette: araC-$P_{BAD}$-LuxAB), a known substrate for GroESL. Increased in vivo concentrations of GroESL result in improved folding of LuxAB and rapid saturation of the luminescence response. FIG. 8C shows a comparison of the ability to visualize plaque formation using S1030, S2058, S2059, and S2060 cells. Chromosomally identical strains lacking (S1030) or carrying the lacZ and groESL cassettes (S2058, S2059, S2060) were infected with WT M13 bacteriophage. The modified strains carry the wild-type (WT) PSP, PSP-T1 or PSP-AR2, respectively. The reduced background and maintained transcriptional activation of the T1 and AR2 variants enables the visualization of phage plaques in top agar supplemented with Bluo-Gal, an X-Gal derivative.

FIGS. 9A-9D show the continuous propagation of Zif268 in PACE, and reversion of an inactive Zif268 mutant to wild-type. FIG. 9A shows plaque assays of Zif268-SP or a control SP encoding T7 RNAP instead of Zif268 on S2060 cells containing APs encoding either the on- or off-target sequence, or S2208 cells (positive control). FIG. 9B is a schematic of the relative location of genes in the Zif268-SP, and a summary of mutations arising following 24 h of PACE to optimize the phage backbone and one-hybrid system. FIG. 9C shows the plaque assay results for wild-type Zif268-SP, inactive mutant Zif268-R24V-SP, and evolved SPs derived from a 24 h drift/24 h PACE experiment in the presence of mutagenesis. '+' denotes the presence of plaques, while '−' denotes the absence of plaques. FIG. 9D shows the genotypes of five phage clones isolated following PACE, all displaying reversion of V24 to R. The nucleic acid sequences in FIG. 9D, from top to bottom, correspond to wild-type (SEQ ID NO: 54), initial (SEQ ID NO: 55) and PACE (SEQ ID NO: 56). The amino acid sequences in FIG. 9D, from top to bottom, correspond to SEQ ID NO: 57, SEQ ID NO: 58, and SEQ ID NO: 57.

FIGS. 10A-10D show the optimization of a TALE one-hybrid architecture for PACE. FIG. 10A shows a comparison of pIII-luciferase fold induction (ATc-induced TALE/noninduced luminescence) resulting from binding of a CBX8-targeting TALE-ω fusion construct to the cognate operator sequence (5'-TTCAGGAGGGCTTCGGC-'3 (SEQ ID NO: 36)) centered at −62. The length of the natural TALE C-terminus used as a linker to the ω subunit is indicated. G45 represents the addition of a GGGGS sequence to the end of the C-terminal fragment to increase the flexibility of the linker. Data represent mean+s.d. (n=3). FIG. 10B shows the plaque assays of TALE-SP or a control SP encoding T7 RNA polymerase instead of a TALE on S2060 cells containing APs with either the on- or off-target sequence, or on S2208 cells (positive control). FIG. 10C is a schematic of the location of genes contained in a CBX8-TALE-SP plasmid, and a summary of evolved mutations following 24 h of PACE. FIG. 10D depicts pIII-luciferase fold induction (ATc-induced TALE/non-induced luminescence) by binding of a CBX8-targeting TALE-ω to CBX8-binding sequences beginning with 5' A, C, G, or T. Data represent mean+s.d. (n=3).

FIGS. 13A-13H show characterizations of the mutations arising from the evolution towards 5' A, C, or G target sequence binding. FIG. 13A shows the location of mutations with >5% prevalence in the population identified in 5' A, C, or G evolutions within the core TALE unit (SEQ ID NO: 66). 'Multiple' refers to equivalent mutations identified in multiple different repeats either in the same experiment or in a separate experiment. FIG. 13B shows luciferase activity represented as fold induction (ATc-induced TALE luminescence/non-induced luminescence) for the canonical TALE and five mutant constructs using a 5' A CBX8-target sequence. FIG. 13C presents the crystal structure[48] showing the location of A133, A79, and W120. The corresponding number for each residue in the crystal structure[48] is shown in parenthesis. FIG. 13D shows luciferase activity represented as fold induction (ATc-induced TALE luminescence/non-induced luminescence) for the a CBX8-directed TALE with an A79E mutation on CBX8-directed target sequences beginning with 5' A, C, G, or T. FIG. 13E presents the crystal structure[49] indicating the position of the C-terminal residue Q711. Numbering corresponding to the original crystal structure[49] is shown in parenthesis. Crystal structure[49] of three TALE repeats showing the positions of the L508 (FIG. 13F), E622 (FIG. 13G), and K634 (FIG. 13H) residues within a core TALE repeat (repeat in light shading, residues in dark shading). Bar graphs in FIGS. 13B and 13D represent mean+s.d. (n=3).

FIGS. 14A-14C show the specificity of phage evolved to recognize 5' A, C, or G. and negative selection validation. FIG. 14A shows the results of plaque assays of phage pools evolved on CBX8-directed target sequences beginning with 5' A, C, or, G on S1059 cells (positive control), or S1030 cells carrying no APs (negative control), or S1030 cells carrying AP containing target sequences beginning with 5' A, C, G, or T. FIG. 14B presents plaque assays using phage evolved to bind a 5' A target sequence on S1030 cells carrying the indicated combinations of AP/APNeg plasmids in the presence of increasing doses of theophylline. FIG. 14C shows the results of a similar experiment to FIG. 14B using different doses of theophylline. '−' indicates no plaque formation, '+' indicates weak plaque formation, '++' indicates moderate plaque formation, and '+++' indicates strong phage plaque formation.

FIG. 15A shows the genotypes of five evolved phage clones from lagoon 1 or lagoon 2 following 144 h of PACE under positive selection for 5' A binding, and negative selection against CBX8-target sequences beginning with 5' C, G, or T. Light shaded squares indicate mutations within the TALE domain, and dark shaded squares indicate mutations within the ω subunit. FIG. 15B shows mutations arising in lagoon 1 (L1) or lagoon 2 (L2) following 144 h of dual positive and negative selection PACE. Only mutations arising at a frequency of >5% are shown.

FIG. 16A depicts the crystal structure[49] showing the location of K59 and W120. The corresponding number for each residue in the crystal structure is shown in parenthesis. FIG. 16B depicts the crystal structure[49] of three TALE repeats showing the relative position of the Q513 (repeat in light shading, residue in dark shading). FIG. 16C shows the luciferase activity represented as fold induction (ATc-induced TALE luminescence/non-induced luminescence) for the canonical CBX8-directed TALE or a K59E mutant protein on CBX8-directed target sequences beginning with 5' A, C, G, or T. FIG. 16D shows the luciferase activity represented as fold induction (ATc-induced TALE luminescence/non-induced luminescence for the indicated doses of ATc) for the canonical ATM-L-directed TALE or a K59E mutant protein on ATM-L directed target sequences beginning with 5' A, C, G, or T. Data represent mean+s.d. (n=3).

FIG. 17A depicts TALEN dose titration showing the relative cleavage efficiencies of the canonical ATM TALEN pair or the L3-2 TALEN on 50 ng (~0.75 nM) of a linear 6-kb DNA fragment containing the ATM on-target sequence (ATM: 5'-TGAATTGGGATGCTGTTT-3' (SEQ ID NO: 15)). The top band is non-cleaved DNA, while the bottom band is a cleavage product. Quantified cleavage percentages were determined using densitometry (GelEval), and are shown below each lane. FIG. 17B shows DNA cleavage saturation curves for the canonical ATM TALEN pair and the TALEN pair containing the evolved L3-2 TALE. An in vitro cleavage assay was performed to measure DNA cleavage of 0.5 ng of DNA containing the ATM on-target sequence (~7.5 pM) by either the canonical TALEN pair or the L3-2 TALEN pair at concentrations of 0.01, 0.04, 0.12, 0.37, 1.11, 3.33, or 10 nM. The amount of uncleaved DNA remaining after the reaction was quantified by qPCR. Fraction cleaved DNA was calculated as the amount of cleaved DNA present following completion of each cleavage reaction divided by the total amount of DNA input into each reaction.

FIG. 18A shows the luciferase activity represented as fold induction (ATc-induced TALE luminescence/non-induced luminescence) for the canonical ATM-L-directed TALE or L3-1 and L3-2, on the on-target sequence (ATM: 5'-TGAATTGGGATGCTGTTT-3' (SEQ ID NO: 15)), or on the off-target sequence OffA17 (OffA17: 5'-GGAAATGGGATACTGAGT-3' (SEQ ID NO: 21)). Data represent mean+s.d. (n=3). FIGS. 18B-18C show the genotypes of individual evolved phage clones following dual positive and negative selection PACE (against OffA17). Light shaded squares indicate mutations within the TALE domain, and dark shaded squares indicate mutations within the ω subunit. The left panel of FIG. 18D shows the relative cleavage efficiencies of the canonical ATM TALEN pair or two TALENs containing an evolved left half-site (L1-1, or L3-2) on a linear 6-kb DNA fragment containing either the ATM on-target sequence or the OffA17 off-target sequence. The top band is non-cleaved DNA, while the bottom band is a cleavage product. Quantified cleavage percentages were determined using densitometry (GelEval), and are shown below each lane. The right panel of FIG. 18D shows mutations in the evolved ATM-left half site TALEs used in the left panel.

FIGS. 19A-19F show the characterization of mutations identified in positive and negative selection ATM-L TALE PACE and evolved TALEN specificity. Relative cleavage efficiencies of the canonical ATM TALEN pair, or a TALEN (L1-2) containing an evolved left half-site TALE with the A252T mutation and the canonical right half-site TALE on a linear 6-kb DNA fragment containing either the ATM on-target sequence or the OffA17 off-target sequence (FIG. 19A). The top band is non-cleaved DNA, while the bottom band is a cleavage product. FIG. 19B is the same as in FIG. 19A, but assaying a TALEN containing a Q745P substitution. Crystal structure[49] of three TALE repeats showing the relative positions of the A252 (FIG. 19C), and L338 (FIG. 19D) residues within a core TALE repeat (repeat in light shading, residues in dark shading). FIG. 19E shows the relative cleavage efficiencies of the canonical ATM TALEN pair, or a TALEN (L3-1) containing an evolved left half-site on a linear 6-kb DNA fragment containing either the ATM on-target sequence, the OffA17 sequence, or a derivative of the OffA17 sequence containing a subset of its 5 mutations (D1-D4 listed in the figure). The sequences, from top to bottom, correspond to SEQ ID NOs: 15, 21, and 67-70. FIG. 19F is the same as in FIG. 19E, but with derivative sequences containing fewer mutations relative to the on-target sequence (1 or 2 bp). The sequences, from top to bottom, correspond to SEQ ID NOs: 15, 71-74. For all cleavage gels, the top band is non-cleaved DNA, while the bottom band is a cleavage product. Quantified cleavage percentages were determined using densitometry (GelEval), and are shown below each lane.

FIG. 20A shows sequences surviving selection (TALEN digestion) compared to the pre-selection library as a function of the number of mutations in both half-sites (left and right half-sites combined excluding the spacer) for each of the ten reaction conditions listed. FIG. 20B shows the enrichment value of on-target (no mutations) and off-target sequences containing one to nine mutations in both half sites (left and right half-sites combined excluding the spacer) for each of the ten reaction conditions listed.

FIGS. 21A-21D are specificity profile heat maps for the canonical ATM TALEN pair as a function of concentration. Heat maps showing specificity scores for the canonical TALEN targeting the ATM locus used in the cleavage assay at doses of 20 nM (FIG. 21A), 10 nM (FIG. 21B), 5 nM (FIG. 21C), and 2.5 nM (FIG. 21D). Each position in the left and right half-sites plus a single flanking position (N) are shown. Colors range from dark shading at a score of 1.0 (complete specificity), to white at a score of 0 (no specificity), to dark shading at a score of −1.0 (maximum negative score). The cognate base for each position in the target sequence is boxed. For the right half-site, data for the sense strand are displayed. The sequences, from left to right, correspond to SEQ ID NOs: 50 and 51.

FIGS. 23A-23F are the specificity profile heat maps of L2-1, L3-1, and L3-2 ATM TALEN pairs. Heat maps showing specificity scores for the L3-1 TALEN pair at doses of 20 nM (FIG. 23A), 10 nM (FIG. 23B), 5 nM (FIG. 23C), and 2.5 nM (FIG. 23D), or TALEN pairs incorporating L3-2 and L2-1 TALEs at a dose of 10 nM (FIGS. 23E and 23F, respectively). Each position in the left and right half-sites plus a single flanking position (N) are shown. Colors range from dark shading at a score of 1.0 (complete specificity), to white at a score of 0 (no specificity), to dark shading at a score of −1.0 (maximum negative score). The cognate base for each position in the target sequence is boxed. For the right half-site, data for the sense strand are displayed. The sequences, from left to right, correspond to SEQ ID NOs: 50 and 51.

DEFINITIONS

Figure 1A:
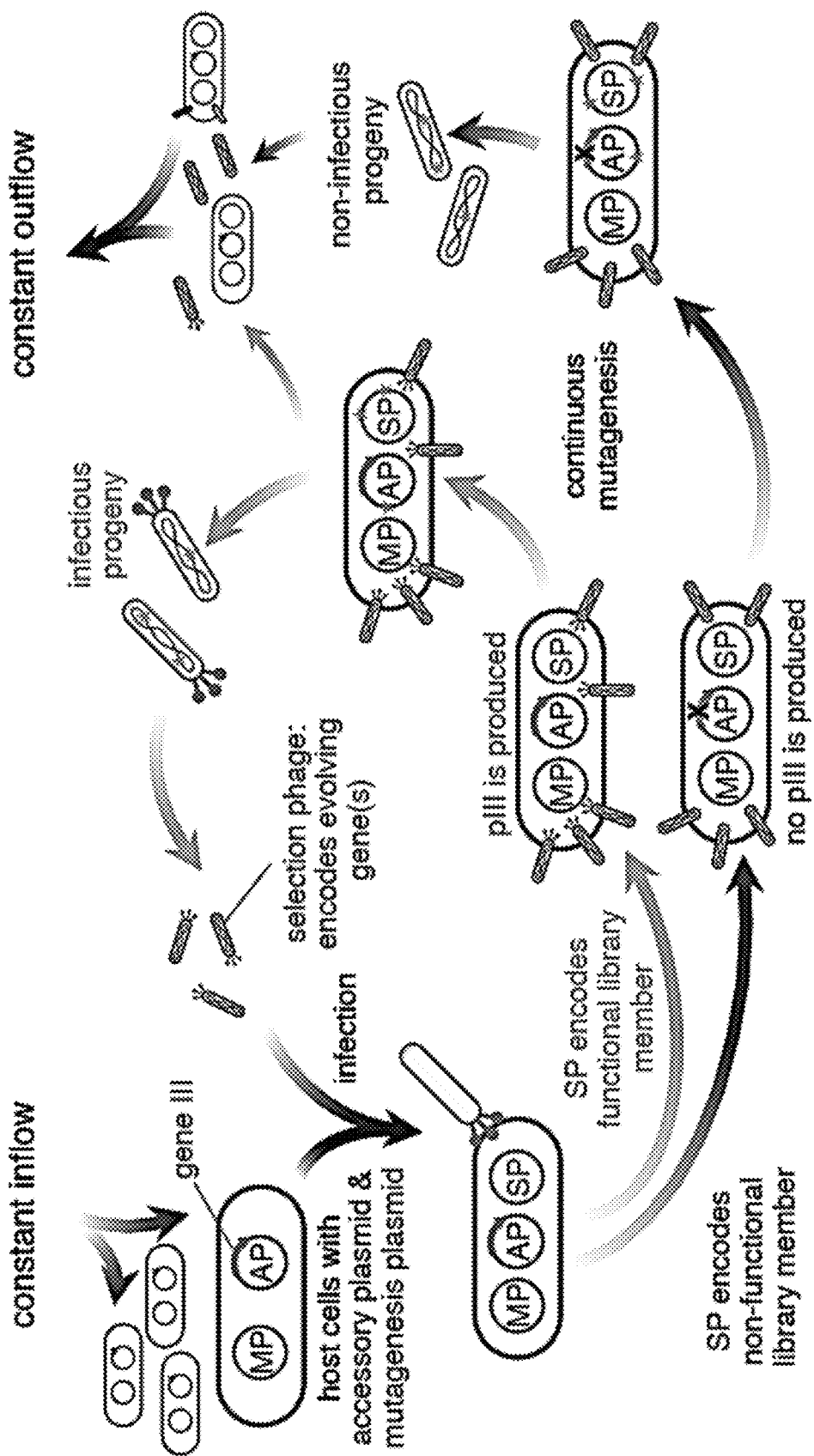
FIGS. 1A-1D show the development of a DNA-binding continuous evolution system.

The term "canonical sequence," as used herein, refers to a sequence of DNA, RNA, or amino acids that reflects a common choice of base or amino acid at each position amongst known molecules of that type. For example, the canonical amino acid sequence of a protein domain may reflect the most common choice of amino acid resides at each position amongst all known domains of that type, or amongst the majority of known domains of that type.

The terms "conjugating," "conjugated," and "conjugation" refer to an association of two entities, for example, of two molecules such as two proteins, two domains (e.g., a binding domain and a cleavage domain), or a protein and an agent (e.g., a protein binding domain and a small molecule). The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein.

The term "effective amount," as used herein, refers to an amount of a biologically active agent that is sufficient to elicit a desired biological response. For example, in some embodiments, an effective amount of a TALE nuclease may refer to the amount of the nuclease that is sufficient to induce cleavage of a target site specifically bound and cleaved by the nuclease, e.g., in a cell-free assay, or in a target cell, tissue, or organism. As will be appreciated by the skilled artisan, the effective amount of an agent, e.g., a nuclease, a hybrid protein, or a polynucleotide, may vary depending on various factors as, for example, on the desired biological response, the specific allele, genome, target site, cell, or tissue being targeted, and the agent being used.

The term "engineered," as used herein, refers to a molecule, complex, substance, or entity that has been designed, produced, prepared, synthesized, and/or manufactured by a human. Accordingly, an engineered product is a product that does not occur in nature. In some embodiments, an engineered molecule or complex, e.g., an engineered TALEN monomer, dimer, or multimer, is a TALEN that has been designed to meet particular requirements or to have particular desired features e.g., to specifically bind a target sequence of interest with minimal off-target binding, to have a specific minimal or maximal cleavage activity, and/or to have a specific stability.

The term "homology," as used herein, refers to the overall relatedness between nucleic acids (e.g. DNA molecules and/or RNA molecules) or polypeptides. In some embodiments, two amino acid sequences are considered to be homologous if the amino acid sequences are at least about 50% identical, at least about 55% identical, at least about 60% identical, at least about 65% identical, at least about 70% identical, at least about 75% identical, at least about 80% identical, at least about 85% identical, at least about 90% identical, at least about 95% identical, at least about 96% identical, at least about 98% identical, or at least about 99% identical for at least one stretch of at least about 20 contiguous amino acids. Those of skill in the art will be aware of suitable methods for aligning and determining homology between two nucleic acid or amino acid sequences. Exemplary suitable methods include, without limitation, those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data, Part I*, Griffin, A. M., and Griffin, H. G., eds., Humana Press, N.J., 1994; and *Sequence Analysis Primer*, Gribskov, M. and Devereux, J., eds., M Stockton Press, New York, 1991; the entire contents of each of which are incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can also be determined using the GAP program in the GCG software package using an NWSgapdna.CMP matrix. Additional exemplary suitable methods commonly employed to determine percent identity between sequences include, but are not limited to those disclosed in Carillo, H., and Lipman, D., *SIAM J Applied Math.*, 48:1073 (1988); incorporated herein by reference. Exemplary suitable computer software to determine homology between two sequences include, but are not limited to, GCG program package, Devereux, J., et al., *Nucleic Acids Research*, 12(1), 387 (1984)), BLASTP, BLASTN, and FASTA Atschul, S. F. et al., *J. Molec. Biol.*, 215, 403 (1990)).

The term "linker," as used herein, refers to a chemical group or a molecule linking two molecules or moieties, e.g., a binding domain and a cleavage domain of a TALE nuclease. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety.

The term "nuclease," as used herein, refers to an agent, for example, a protein or a nucleic acid molecule, capable of cleaving a phosphodiester bond connecting nucleotide residues in a nucleic acid molecule. In some embodiments, a nuclease is a protein, e.g., an enzyme or enzyme domain that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease site-specific nuclease, binding and/or cleaving a specific phosphodiester bond within a specific nucleotide sequence, which is also referred to herein as the "recognition sequence," the "nuclease target site," or the "target site." The nuclease, in some embodiments, comprises a nuclease domain from a naturally-occurring nuclease. In some embodiments, the nuclease comprises a nuclease domain from a non-naturally-occurring nuclease. In some embodiments, the nuclease comprises a nuclease domain from a meganuclease, a zinc finger nuclease, a TALE nuclease (TALEN), or a restriction endonuclease (e.g., FokI, EcoRI, HindIII, or BamHI). The nucleases and nuclease domains provided herein are exemplary and meant to illustrate some embodiments, but are not meant to be limiting. Those of ordinary skill in the art will be aware of additional suitable nucleases and nuclease domains.

A nuclease protein typically comprises a "binding domain" that mediates the interaction of the protein with the nucleic acid substrate, and a "cleavage domain" that catalyzes the cleavage of the phosphodiester bond within the nucleic acid backbone. In some embodiments, a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be combined to create nucleases that bind specific target sites, are well known to those of skill in the art. For example, transcriptional activator like elements can be used as binding domains to specifically bind a desired target site, and fused or conjugated to a cleavage domain, for example, the cleavage domain of FokI, to create an engineered nuclease cleaving the desired target site.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications' A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject in the context of treatment of a disease or disorder. In some embodiments, a pharmaceutical composition comprises an active ingredient, e.g. a nuclease or a nucleic acid encoding a nuclease, and a pharmaceutically acceptable excipient.

The terms "prevention" or "prevent" refer to the prophylactic treatment of a subject who is at risk of developing a disease, disorder, or condition (e.g., at an elevated risk as compared to a control subject, or a control group of subject, or at an elevated risk as compared to the average risk of an age-matched and/or gender-matched subject), resulting in a decrease in the probability that the subject will develop the disease, disorder, or condition (as compared to the probability without prevention), and/or to the inhibition of further advancement of an already established disorder.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasms are also referred to as cancers.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode.

The term "target site," used herein interchangeably with the term "nuclease target site," refers to a sequence within a nucleic acid molecule that a TALE binds to. A target site may be single-stranded or double-stranded. In the context of nucleases that dimerize, e.g., TALENs comprising a FokI DNA cleavage domain, a target site typically comprises a left half-site (bound by one monomer of the nuclease), a right half-site (bound by the second monomer of the nuclease), and a spacer sequence between the half sites in which the cut is made. This structure ([left half-site]-[spacer sequence]-[right half-site]) is referred to herein as an LSR structure. In some embodiments, the left half-site and/or the right half-site is between 10-18 nucleotides long. In some embodiments, either or both half-sites are shorter or longer. In some embodiments, the left and right half sites comprise different nucleic acid sequences.

The term "Transcriptional Activator-Like Effector," (TALE) as used herein, refers to DNA binding proteins comprising a TALE repeat array and an effector domain. Typically, the TALE repeat array comprises a plurality of highly conserved 33-34 amino acid sequence comprising a highly variable two-amino acid motif (Repeat Variable Diresidue, RVD). The RVD motif determines binding specificity to a nucleic acid sequence, and can be engineered according to methods well known to those of skill in the art to specifically bind a desired DNA sequence (see, e.g., Miller, Jeffrey; et. al. (February 2011). "A TALE nuclease architecture for efficient genome editing". Nature Biotechnology 29 (2): 143-8; Zhang, Feng; et. al. (February 2011). "Efficient construction of sequence-specific TAL effectors for modulating mammalian transcription". Nature Biotechnology 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". PLoS ONE 6 (5): e19509; Boch, Jens (February 2011). "TALEs of genome targeting". Nature Biotechnology 29 (2): 135-6; Boch, Jens; et. al. (December 2009). "Breaking the Code of DNA Binding Specificity of TAL-Type III Effectors". Science 326 (5959): 1509-12; and Moscou, Matthew J.; Adam J. Bogdanove (December 2009). "A Simple Cipher Governs DNA Recognition by TAL Effectors". Science 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs. As used herein in the context of TALE proteins, the term "effector" or "effector domain" refers to a molecule, moiety, or domain capable of modifying a nucleic acid and/or modulating transcription of one or more genes of a nucleic acid. In some embodiments, the effector domain comprises a nuclease, a recombinase, a transcriptional activator, a transcriptional repressor, or an epigenome modifying enzyme or domain (e.g., a methyltransferase, demethylase, acetyltransferase, acetylase, etc.). Exemplary effectors are provided herein and additional suitable effectors will be apparent to those of skill in the art. The disclosure is not limited in this respect.

The term "Transcriptional Activator-Like Element Nuclease," (TALEN) as used herein, refers to an artificial nuclease comprising a transcriptional activator like effector DNA binding domain to a DNA cleavage domain, for example, a FokI domain. A number of modular assembly schemes for generating engineered TALE constructs have been reported (Zhang, Feng; et. al. (February 2011). "Efficient construction of sequence-specific TAL effectors for modulating mammalian transcription". Nature Biotechnology 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". PLoS ONE 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". Nucleic Acids Research; Morbitzer, R.; Elsaesser, J.; Hausner, J.; Lahaye, T. (2011). "Assembly of custom TALE-type DNA binding domains by modular cloning". Nucleic Acids Research; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". Nucleic Acids Research.; Weber, E.; Gruetzner, R.; Werner, S.; Engler, C.; Marillonnet, S. (2011). Bendahmane, Mohammed ed. "Assembly of Designer TAL Effectors by Golden Gate Cloning". PLoS ONE 6 (5): e19722; the entire contents of each of which are incorporated herein by reference).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be

DETAILED DESCRIPTION

Modified TALE Domains and Proteins that Bind Non-Canonical 5' Nucleotides

Modified TALE N-Terminal Domains

Some aspects of this disclosure are based on the recognition that certain modifications (e.g., mutations or amino acid substitutions) within TALE proteins or TALE domains affect the target nucleic acid binding specificity with respect to the 5' nucleotide of a target nucleic acid. Accordingly, some aspects of this disclosure provide proteins with modified TALE N-terminal domains. In some embodiments, the disclosure provides proteins comprising an amino acid sequence that is at least 80% identical to the amino acid sequence of SEQ ID NO: 1 with an alanine to glutamic acid amino acid substitution at amino acid residue 39 (A39E) and/or a lysine to glutamic acid amino acid substitution at amino acid residue 19 (K19E) as compared to (SEQ ID NO: 1) or a homologous residue in a canonical N-terminal TALE domain. As used herein, a "a canonical N-terminal TALE domain," refers to any naturally occurring N-terminal TALE domain. In some embodiments, the N-terminal TALE domain is from a Xanthomonas bacteria. Exemplary Xanthomonas bacteria include, without limitation, X. campestris, X. euvesicatoria, X. citri, X. axonopodis, X. alfalfa, X. perforans, X. vesicatoria, X. smithii, and X. gardneri. N-terminal TALE domains are known in the art and would be recognized by the skilled artisan. In some embodiments a canonical N-terminal TALE domain comprises the amino acid sequence of SEQ ID NO: 1. In some embodiments a canonical N-terminal TALE domain consists of the amino acid sequence of SEQ ID NO: 1. In some embodiments, a canonical N-terminal TALE domain consists essentially of the amino acid sequence of SEQ ID NO: 1. For the purpose of clarity, lysine 19 (K19) and alanine 39 (A39) of SEQ ID NO: 1 are underlined and in bold as shown below.

Canonical N-Terminal TALE Domain (SEQ ID NO: 1)
VDLRTLGYSQQQQEKIKPKVRSTVAQHHEALVGHGFTHAHIVALSQHPAA

LGTVAVKYQDMIAALPEATHEAIVGVGKQWSGARALEALLTVAGELRGPP

LQLDTGQLLKIAKRGGVTAVEAVHAWRNALTGAPLN

In some embodiments, the disclosure provides proteins comprising an amino acid sequence that is at least 80% identical to the amino acid sequence of SEQ ID NO: 1 with an alanine to glutamic acid amino acid substitution at amino acid residue 39 (A39E) and/or a lysine to glutamic acid amino acid substitution at amino acid residue 19 (K19E) as compared to a homologous residue in a canonical N-terminal TALE domain. The concept of homology and a "homologous residue" is known in the art and would be recognized by a skilled artisan. Further, exemplary computer software used to determine homology between two sequences include, but are not limited to, GCG program package, Devereux, J., et al., Nucleic Acids Research, 12(1), 387 (1984)), BLASTP, BLASTN, and FASTA Atschul, S. F. et al., J. Molec. Biol., 215, 403 (1990)). It should be appreciated that when the amino acid residues of SEQ ID NO: 1 (e.g., amino acid residues K19 and A30 of SEQ ID NO: 1) are being compared to the amino acid residues of a canonical N-terminal TALE domain, the amino acid sequences may not be the same length and thus, the numbering scheme between SEQ ID NO: 1 and the canonical N-terminal TALE domain may not align with respect to homologous amino acid residues. Accordingly, the amino acid substitutions provided herein may be identified as compared to a homologous residue in a canonical N-terminal TALE domain rather than by an absolute amino acid position within an amino acid sequence.

In some embodiments, the proteins of the present disclosure comprise an amino acid sequence that is at least 80% identical to the amino acid sequence of SEQ ID NO: 1 with an alanine to glutamic acid amino acid substitution at amino acid residue 39 (A39E) as compared to (SEQ ID NO: 1) or a homologous residue in a canonical N-terminal TALE domain. In some embodiments, the proteins of the present disclosure comprise an amino acid sequence that is at least 80% identical to the amino acid sequence of SEQ ID NO: 1 with a lysine to glutamic acid amino acid substitution at amino acid residue 19 (K19E) as compared to (SEQ ID NO: 1) or a homologous residue in a canonical N-terminal TALE domain. In some embodiments, the proteins of the present disclosure comprise an amino acid sequence that is at least 80% identical to the amino acid sequence of SEQ ID NO: 1 with an alanine to glutamic acid amino acid substitution at amino acid residue 39 (A39E) and a lysine to glutamic acid amino acid substitution at amino acid residue 19 (K19E) as compared to (SEQ ID NO: 1) or a homologous residue in a canonical N-terminal TALE domain.

In some embodiments, the proteins of the present disclosure comprise an amino acid sequence that is at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to SEQ ID NO: 1. In some embodiments, the proteins of the present disclosure comprise an alanine to glutamic acid substitution at amino acid residue 93 (A93E) as compared to SEQ ID NO: 1 or a homologous residue in a canonical N-terminal TALE domain. In some embodiments, the proteins of the present disclosure comprise a glycine to arginine amino acid substitution at amino acid residue 98 (G98R) as compared to SEQ ID NO: 1 or a homologous residue in a canonical N-terminal TALE domain. In some embodiments, the proteins of the present disclosure comprise one or more of amino acid substitution S22N, G77D, A85T, T91A, A93G, P99S, P99T, A129E, and N136T as compared to SEQ ID NO: 1, or a homologous residue in a canonical N-terminal TALE domain. In some embodiments, the proteins of the present disclosure comprise an arginine to tryptophan amino acid substitution at amino acid residue 21 (R21W) as compared to SEQ ID NO: 1 or a homologous residue in a canonical N-terminal TALE domain. In some embodiments, the proteins of the present disclosure may comprise one or more of amino acid substitutions K19E, S22N, A39E, G77D, A85T, T91A, A93E, A93G, G98R, P99S, P99T, A129E, and N136T as compared to SEQ ID NO: 1, or a homologous residue in a canonical N-terminal TALE domain.

Modified TALE Repeat Arrays

Some aspects of this disclosure are based on the recognition that certain modifications (e.g., mutations or amino acid substitutions) within a TALE repeat array alter the target nucleic acid binding specificity with respect to the 5' nucleotide of a target nucleic acid. Aspects of the disclosure provide proteins comprising one or more TALE repeat sequences, which may be combined (e.g., in tandem) to form TALE repeat arrays. TALE repeat arrays are typically made up of multiple 34-amino acid TALE repeat sequences, each of which uses a repeat-variable di-residue (RVD), typically the amino acids at positions 12 and 13, to recognize a target site. TALE repeat sequences are known in the art and have been described previously, for example, in Tebas, P. et al. Gene editing of CCR5 in autologous CD4 T cells of persons infected with HIV. N Engl J Med 370, 901-10 (2014) and Genovese, P. et al. Targeted genome editing in human repopulating haematopoietic stem cells. Nature 510, 235-40 (2014), the contents of each of which are incorporated herein by reference. Examples of RVDs that enable recognition of each of the four DNA base pairs are known, enabling arrays of TALE repeats to be constructed that can bind virtually any DNA sequence. As used herein, a "TALE repeat sequence" refers to an amino acid sequence that is at least 80% identical to the amino acid sequence of SEQ ID NO: 2, including any of the amino acid substitutions disclosed herein.

Accordingly, aspects of the disclosure relate to proteins comprising an amino acid sequence that is at least 80% identical to the amino acid sequence of SEQ ID NO: 2. The letter "X" in SEQ ID NO: 2 specifies any amino acid residue and the subscript numbers immediately right of the "X" are used to identify each "X" in the amino acid sequence for the purpose of clarity. In some embodiments, amino acid positions 12 and 13 of SEQ ID NO: 2, specified by $X_3$ and $X_4$ respectively, the repeat-variable di-residue (RVD). For the purpose of clarity, residues 12 and 13, of SEQ ID NO: 2 are underlined and in bold as shown below.

General formula of a TALE repeat sequence:

(SEQ ID NO: 2)
LTPX$_1$QVVAIAX$_2$X$_3$X$_4$GGX$_5$X$_6$ALETVQRLLPVLCQX$_7$HG.

In some embodiments, $X_1$ is D, E or A, $X_2$ is S or N, $X_3$ is N or H, $X_4$ is G, D, I, or N, $X_5$ is K or R, $X_6$ is Q or P, and/or $X_7$ is D or A as shown in SEQ ID NO: 2. In some embodiments, the proteins of the present disclosure comprise one or more of the following amino acid substitutions: T2A, P3L, P3S, $X_1$4G, $X_1$4K, $X_1$4N, $X_2$11K, $X_2$11Y, $X_3$12H, $X_4$13K, $X_4$13H, G15S, $X_5$16R, $X_6$17P, T21A, L26F, P27S, V28G, Q31K, $X_7$32S, D32E, and H33L as compared to SEQ ID NO: 2. In some embodiments, the proteins of the present disclosure comprise an amino acid sequence is at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to SEQ ID NO: 2.

In some embodiments, the proteins of the present disclosure comprise one or more of the following amino acid substitutions: P3L, $X_1$4G, $X_1$4K, $X_2$11Y, $X_5$16R, $X_6$17P, T21A, and L26F as compared to SEQ ID NO: 2. In some embodiments, the proteins of the present disclosure comprise one or more of the following amino acid substitutions: P3S, $X_1$4K, $X_3$12H, $X_5$16R, and L26F as compared to SEQ ID NO: 2. In some embodiments, the proteins of the present disclosure comprise one or more of the following amino acid substitutions: $X_1$4N, $X_1$4K, $X_2$11K, G15S, $X_5$16R, L26F, P27S, A32S, D32E, and H33L as compared to SEQ ID NO: 2. In some embodiments, the proteins of the present disclosure comprise one or more of the following amino acid substitutions: T2A, P3L, $X_1$4K, $X_3$12H, V28G, and Q31K as compared to SEQ ID NO: 2. In some embodiments, the proteins of the present disclosure comprise one or more of the following amino acid substitutions: $X_1$4N, $X_1$4K, $X_2$11K, $X_5$16R, T21A, and L26F as compared to SEQ ID NO: 2. In some embodiments, the proteins of the present disclosure comprise one or more of the following amino acid substitutions: A8G, $X_4$13K, $X_4$13H, A18G, E20G, Q23K, L26A, H33P, H33Y, and G34S as compared to SEQ ID NO: 2.

In some embodiments, the proteins of the present disclosure comprise a plurality of TALE repeat sequences that are at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to SEQ ID NO: 2. In some embodiments, the proteins of the present disclosure comprise a plurality of TALE repeat sequences that are made up of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 60, at least 80, or at least 100 of the TALE repeat sequences disclosed herein.

The plurality of TALE repeat sequences of the present disclosure may be arranged in any order. In some embodiments, the proteins provided herein have one or more TALE repeat sequences that are directly adjoined (contiguous) to each other without a linker. For example the C-terminal amino acid residue of a first TALE repeat sequence may be directly adjoined to the N-terminal amino acid residue (e.g., by a peptide bond) to generate a protein having a plurality of TALE repeat sequences that are directly adjoined. In some embodiments, the TALE repeat sequences are not directly adjoined. For example, the TALE repeat sequences may be joined by one or more linkers. In some embodiments the one or more linkers comprises an amino acid linker. In some embodiments, the one or more amino acid linkers is at least 1 amino acid, at least 2 amino acids, at least 3 amino acids, at least 4 amino acids, at least 5 amino acids, at least 6 amino acids, at least 7 amino acids, at least 8 amino acids, at least 9 amino acids, at least 10 amino acids, at least 15 amino acid, at least 20 amino acids, at least 25 amino acids, at least 30 amino acids, at least 40 amino acids, at least 50 amino acids, at least 60 amino acids, at least 80 amino acids, or at least 100 amino acids in length. It should be appreciated that the proteins, described herein, may comprise both TALE repeat sequences that are directly adjoined as well as TALE repeat sequences that are joined by one or more linkers.

In some embodiments, the plurality of TALE repeat sequences form a TALE repeat array. As used herein, a "TALE repeat array" refers to at least 5 TALE repeat sequences that are directly adjoined. In some embodiments, the TALE repeat array comprises at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, or at least 100 TALE repeat sequences. In some embodiments, the TALE repeat array comprises at least 6, at least 7, at least 8, 9, 10, 11, 12, 13, 14, 15, 16, 17, 18, 19, 20, 21, 22, 23, 24, 25, 26, 27, 28, 29, or 30 TALE repeat sequences, either used alone or in combination with other TALE arrays. In some embodiments, the proteins of the present disclosure comprise an amino acid sequence is at least 80% identical to the amino acid sequence provided in SEQ ID NO: 6. In some embodiments, the proteins of the present disclosure comprise one or more of the following amino acid substitutions: K16R; K50R; L94F; T104A; P173L; L196F; K220R; L230F; A236S; N249Y; Q255P; T259A; D276G; L332F; Q337K; H373L; P377L; N386H; G389S; P401S; D406E; P411S; D412N; V436G; E446K; N453K; N455K; K458R; and P513L; as compared to SEQ ID NO:6. or their corresponding equivalent substitutions in similar TALEs)

In some embodiments, the proteins of the present disclosure comprise an amino acid sequence is at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to SEQ ID NO: 6. In some embodiments, the proteins of the present disclosure comprise a TALE repeat array comprising an amino acid substitution or a combination of amino acid substitutions selected from the following: K50R and L230F; L230F; L230F and N249Y; Q255P; T259A; P377L; and D276G, E446K, and P513L; as compared to SEQ ID NO: 6. In some embodiments, the proteins of the present disclosure comprise a TALE repeat array comprising one of the amino acid substitutions or combination of amino acid substitutions selected from: K50R and N453K; L332F and K458R; N386H; P411S and N453K; E446K; N453K; and K458R; as compared to SEQ ID NO: 6. In some embodiments, the proteins of the present disclosure comprise a TALE repeat array comprising one of the amino acid substitutions or combination of amino acid substitutions selected from: K16R, G389S, and E446K; K16R, G389S, and E446K; L94F; L196F, G389S, P401S, and E446K; K220R; A236S, G389S, and E446K; H373L and D412N; G389S, D406E, and E446K; D412N; and N455K; as compared to SEQ ID NO: 6. In some embodiments, the proteins of the present disclosure comprise a TALE repeat array comprising one of the amino acid substitutions or combination of amino acid substitutions selected from: T104A, Q337K, N386H, and E446K; P173L, Q337K, N386H, E446K, and V436G; and Q337K, N386H, E446K, and V436G; as compared to SEQ ID NO: 6.

Modified TALE C-Terminal Domains

Some aspects of this disclosure are based on the recognition that certain modifications (e.g., truncations, mutations or amino acid substitutions) of a TALE C-terminal domain affect the target nucleic acid binding specificity with respect to the 5' nucleotide of a target nucleic acid. In some embodiments, the disclosure provides proteins comprising an amino acid sequence that is at least 80% identical to the amino acid sequence of any one of SEQ ID NOs: 3, 4, or 5 with a glutamine to proline amino acid substitution at amino acid residue 5 (Q5P) as compared to either SEQ ID NO: 3, 4, or 5, or a homologous residue in a canonical C-terminal TALE domain. As used herein, a "a canonical C-terminal TALE domain," refers to any naturally occurring C-terminal TALE domain. In some embodiments, the C-terminal TALE domain is from a Xanthomonas bacteria. Exemplary Xanthomonas bacteria include, without limitation, X. campestris, X. euvesicatoria, X. citri, X. axonopodis, X. alfalfa, X. perforans, X. vesicatoria, X. smithii, and X. gardneri. C-terminal TALE domains are known in the art and would be recognized by the skilled artisan. In some embodiments a canonical C-terminal TALE domain comprises any one of the amino acid sequences of SEQ ID NOs: 3, 4, or 5. In some embodiments, a canonical C-terminal TALE domain consists of any one of the amino acid sequences of SEQ ID NOs: 3, 4, or 5. In some embodiments, a canonical C-terminal TALE domain consists essentially of any one of the amino acid sequences of SEQ ID NOs: 3, 4, or 5. As used herein, a "C-terminal TALE domain" or "C-terminal domain" refers to any of the canonical C-terminal TALE domains or any of the modified TALE C-terminal domains provided herein.

In some embodiments, the proteins of the present disclosure comprise an amino acid sequence that is at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to any one of SEQ ID NOs: 3, 4, or 5.

Modified TALE Proteins

Some aspects of this disclosure are based on the surprising discovery that certain modifications (e.g., truncations, mutations and/or amino acid substitutions) of TALE proteins affect the target nucleic acid binding specificity with respect to the 5' nucleotide of a target nucleic acid. Typically, a TALE protein, comprises the following structure:

[N-terminal domain]-[TALE repeat array]-[C-terminal domain]

where each "-" individually indicates conjugation, either covalently or non-covalently, and where the conjugation can be direct, e.g., via direct bond, or indirect, e.g., via a linker.

In some embodiments, the N-terminal domain comprises any of the modified TALE N-terminal domains provided herein. In some embodiments, the TALE repeat array comprises any of the modified TALE repeat arrays provided herein. In some embodiments, the C-terminal domain comprises any of the modified TALE C-terminal domains provided herein. In some embodiments, the N-terminal domain comprises a truncated version of the N-terminal domain. In some embodiments, the C-terminal domain comprises a truncated version of the C-terminal domain. In some embodiments, the truncated domain comprises less than 90%, less than 80%, less than 70%, less than 60%, less than 50%, less than 40%, less than 30%, or less than 25% of the residues of the canonical domain. In some embodiments, the truncated C-terminal domain comprises less than 60, less than 50, less than 40, less than 30, less than 29, less than 28, less than 27, less than 26, less than 25, less than 24, less than 23, less than 22, less than 21, or less than 20 amino acid residues. In some embodiments, the truncated C-terminal domain comprises 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 residues. In some embodiments, the N-terminal domain and the TALE repeat array are directly adjoined. In some embodiments, the N-terminal domain and the TALE repeat array are joined by a linker. In some embodiments, the TALE repeat array and the C-terminal domain are directly adjoined. In some embodiments, the TALE repeat array and the C-terminal domain are joined by a linker.

In some embodiments, the protein further comprises an effector domain. In some embodiments, the effector domain may be positioned N-terminal or C-terminal to an N-terminal domain, a TALE repeat array, or a C-terminal domain of the protein. In some embodiments, the protein comprises the structure [N-terminal domain]-[TALE repeat array]-[C-terminal domain]-[effector domain], or [effector domain]-[N-terminal domain]-[TALE repeat array]-[C-terminal domain].

In some embodiments, the effector domain comprises a nuclease domain, a transcriptional activator or repressor domain, a recombinase domain, or an epigenetic modification enzyme domain. The effector domains provided herein can be used in the context of suitable TALE effector molecules, e.g., TALE nucleases, TALE transcriptional activators, TALE transcriptional repressors, TALE recombinases, and TALE epigenome modification enzymes. Additional suitable TALE effectors in the context of which the isolated TALE domains can be used will be apparent to those of skill in the art based on this disclosure. In general, the TALE proteins provided herein are engineered to bind a target sequence with a non-canonical 5' nucleotide (A, C, or G) over the native 5' T, thereby expanding the scope of DNA target sequences that can be bound a TALE protein.

In some embodiments, the nuclease domain is monomeric. In some embodiments, the nuclease domain dimerizes or multimerizes in order to cleave a nucleic acid. Homo- or heterodimerization or multimerization of TALEN monomers typically occurs via binding of the monomers to binding sequences that are in sufficiently close proximity to allow dimerization, e.g., to sequences that are proximal to each other on the same nucleic acid molecule (e.g., the same double-stranded nucleic acid molecule). In some embodiments, the nuclease domain comprises a FokI nuclease domain. In some embodiments, the FokI nuclease domain comprises a homodimeric FokI domain. In some embodiments, the FokI nuclease domain comprises a heterodimeric FokI domain. In some embodiments, the FokI nuclease domain comprises the amino acid sequence of SEQ ID NO: 14. In some embodiments, the FokI nuclease domain comprises the amino acid sequence that is at least 80% identical to the amino acid sequence of SEQ ID NO: 14. It should be understood that the FokI sequences provided herein are exemplary and provided for the purpose of illustrating some embodiments embraced by the present disclosure. They are not meant to be limiting and additional FokI sequences useful according to aspects of this disclosure will be apparent to the skilled artisan based on this disclosure.

In some embodiments, the effector domain comprises a domain capable of increasing transcription of a gene. In some embodiments, the effector domain comprises a transcriptional activation domain. As used herein, a "transcriptional activation" (TAD) refers to a region of a transcription factor which in conjunction with a DNA binding domain can activate transcription (e.g., from a promoter) by contacting transcriptional machinery (e.g., general transcription factors and RNA polymerase) either directly or through other proteins known as co-activators. In some embodiments, the transcriptional activation domain is from a naturally-occurring transcriptional activator or is a protein homologous to a transcriptional activation domain from a naturally-occurring transcriptional activator. Transcriptional activation domains are known in the art and would be recognized by the skilled artisan. In some embodiments, the transcriptional activation domain is from a naturally occurring transcription factor. In some embodiments, the transcription factor comprises a eukaryotic transcription factor. Exemplary eukaryotic transcription factors include, without limitation, p53, VP16, MLL, E2A, HSF1, NF-IL6, NFAT1 and NF-κB. In some embodiments, the transcription factor comprises a prokaryotic transcription factor. In some embodiments, the prokaryotic transcription factor comprises a sigma factor. Exemplary prokaryotic sigma factors include, without limitation, RpoD, FecI, RpoE, RpoF, RpoH, RpoS, and RpoN. In some embodiments, the transcriptional activation domain comprises a domain from an RNA polymerase. In some embodiments, the transcriptional activation domain comprises an omega subunit from RNA polymerase (RNAPω). In some embodiments, the RNA polymerase domain comprises an amino acid sequence that is at least 80% identical to the amino acid sequence provided in SEQ ID NO: 10.

In some embodiments, the RNA polymerase domain comprises an amino acid sequence is at least 85% identical, at least 90% identical, at least 95% identical, at least 98% identical, at least 99% identical, or at least 100% identical to the amino acid sequence provided in SEQ ID NO: 10. In some embodiments, the RNA polymerase domain comprises one or more of the following amino acid substitutions: V9G, D17G, M29T, P36S, and V38G as compared to SEQ ID NO: 10, or a homologous canonical RNA polymerase domain.

In some embodiments, the transcriptional activation domain comprises a domain from a transcription factor, e.g., a transactivating domain (TAD) regulating transcription. Suitable transactivating domains include, without limitation, those present in Gal4, Pdr1, Oaf1, GCN4, VP16, Pho4, Msn2, Ino2, and P201. In some embodiments, the transactivating domain is a transactivating domain of p53 (e.g., p53TAD1, p53TAD2), MLL, E2A, Rtg3, CREB, CREBb6a, Gli3, Gal4, Pip1, or Pip3, e.g., a 9aa TAD of any of these proteins. In addition, small RNA sequences capable of directly supporting transcription which could be fused to or covalently linked directly or through a secondary scaffold to the evolved DBD are embraced by this disclosure.

In some embodiments, the effector domain comprises a domain capable of decreasing transcription of a gene. In some embodiments, the effector domain comprises a transcriptional repressor domain. As used herein, a "transcriptional repressor domain" (TRD) refers to a region of a transcription factor which, in conjunction with a DNA binding domain, can repress transcription (e.g., from a promoter) by contacting transcriptional machinery (e.g., general transcription factors and RNA polymerase) either directly or through other proteins known as co-repressors. Transcriptional repressor domains are known in the art and would be recognized by a skilled artisan. Transcriptional repressor domains, in the context of TALE DNA-binding proteins have been described previously in Cong, L., Zhou, R., Kuo, Y. C., Cunniff, M. & Zhang, F. Comprehensive interrogation of natural TALE DNA-binding modules and transcriptional repressor domains *Nat Commun* 3, 968 (2012), the contents of which are incorporated herein by reference. It should be appreciated that the transcriptional repressor domains described herein and in the cited references are exemplary and are not meant to be limiting.

In some embodiments, the proteins of the present disclosure further comprise a linker, an epitope tag and/or a nuclear localization sequence (NLS). It will be apparent to those skilled in the art that it is desirable in some embodiments to adjust the length of the linker when linking any of the proteins or protein domains (e.g., N-terminal domains, TALE repeat sequences, TALE arrays, C-terminal domains, or effector domains) described herein. For example, the length of the linker may be used to accommodate truncated domains, e.g., truncated C-terminal domains, or to optimally position an effector domain (e.g. a nuclease domain, a transcriptional repressor domain, a transcriptional activator domain, a recombinase domain, or an epigenetic modification enzyme domain) to perform a function (e.g. DNA cleaving, regulating, or modifying a target sequence). In some embodiments, the linker comprises an amino acid. In some embodiments, the linker comprises or consists of one or more amino acids. In some embodiments, the amino acid linker is at least 1, at least 2, at least 3, at least 4, at least 5, at least 10, at least 20, at least 30, at least 40, at least 50, or at least 100 amino acids in length. In some embodiments, the linker comprises the amino acid sequence provided in SEQ ID NO: 8. The linker may be positioned between any of the proteins or protein domains, described herein. In some embodiments, the linker is positioned between the C-terminal domain and the effector domain. In some embodiments, the linker is positioned between the C-terminal domain and the effector domain. In some embodiments, the linker is positioned between the TALE repeat array and the C-terminal domain. In some embodiments, the linker is positioned between the N-terminal domain and the TALE repeat array.

In some embodiments, the proteins of the present disclosure comprise an epitope tag. An "epitope tag" as used herein refers to a peptide sequence that can be attached to a protein (e.g. by using molecular biology techniques). Typically, epitope tags are short peptide sequences that high-affinity antibodies can bind (e.g., for the purposes of detection or affinity purification). Exemplary epitope tags include, but are not limited to V5-tag, Myc-tag, HA-tag and FLAG tag. In some embodiments, the epitope tag comprises a FLAG tag. In some embodiments, the FLAG tag comprises the amino sequence provided in SEQ ID NO: 63 (DYKDDDDK).

In some embodiments, the proteins of the present disclosure comprise a nuclear localization signal (NLS). A "nuclear localization signal" (NLS) as used herein, refers to a peptide sequence that targets a protein, to which it is attached, to the nucleus. Typically, a NLS comprises one or more short sequences of positively charged lysines or arginines exposed on the protein surface. Nuclear localization sequences are known in the art and would be apparent to a skilled artisan. NLSs have been described previously, for example, in Kalderon D. et al., (1984). "A short amino acid sequence able to specify nuclear location". Cell 39 (3 Pt 2): 499-509, and Dingwall C, Robbins J, Dilworth S M, Roberts B, Richardson W D (September 1988). "The nucleoplasmin nuclear location sequence is larger and more complex than that of SV-40 large T antigen". J Cell Biol. 107 (3): 841-9, the contents of each of which are incorporated herein by reference. In some embodiments, the NLS comprises the amino acid sequence provided in SEQ ID NO: 64(PKK-KRKV).

In some embodiments, the protein comprises an amino acid sequence that is at least 80% identical to the amino acid sequence provided in SEQ ID NO: 9. In some embodiments, the protein further comprises an amino acid sequence that is at least 85% identical, at least 90% identical, at least 95% identical, at least 98% identical, or at least 99% identical to the amino acid sequence provided in SEQ ID NO: 9.

The epitope tag and/or the NLS may be positioned in any suitable location within any of the proteins described herein. In some embodiments, the epitope tag and/or the NLS is positioned N-terminal to an N-terminal domain, a TALE array, a C-terminal domain or an effector domain. In some embodiments, the epitope tag and/or the NLS is positioned C-terminal to an N-terminal domain, a TALE array, a C-terminal domain or an effector domain.

Numerous exemplary engineered TALE sequences have been provided herein. It will be understood that the present disclosure embraces all possible combinations of the various engineered TALE sequences, e.g., combinations of any N-terminal TALE domain, any TALE repeat, and any C-terminal TALE domain as provided herein. Those of skill in the art will understand that the TALE repeat array will vary depending on the nucleic acid sequence to be targeted. Methods and strategies to tailor a TALE repeat array for a specific target sequence are well known to those of skill in the art. The disclosure embraces TALE repeat arrays targeting any suitable nucleic acid sequence and comprising either the TALE repeat array modifications disclosed herein or fused to an engineered TALE domain as provided herein. It will be understood by those of skill in the art that the exemplary sequences provided herein are for illustration purposes only and are not intended to limit the scope of the present disclosure. The disclosure also embraces the use of each of the inventive TALE proteins and TALE domains, e.g., the modified N-terminal domains, C-terminal domains, TALE arrays and RNAPω domains described herein. Additional sequences that are useful in accordance to aspects of this disclosure will be apparent to the skilled artisan.

Some TALE proteins disclosed herein are provided as a monomer. Some TALE proteins described herein comprise a nuclease domain (e.g., a FokI domain). In some embodiments, the nuclease domain may dimerize to cleave a nucleic acid sequence. In some embodiments, the proteins described herein are TALENs. In some embodiments the TALENs provide herein form a homodimer. In some embodiments the TALENs provide herein form a heterodimer.

Some aspects of this disclosure are based on the recognition that certain modifications (e.g., mutations or amino acid substitutions) within TALE proteins or TALE domains (N-terminal domain, TALE array or C-terminal domain) affect the target nucleic acid binding specificity of the TALE with respect to the 5' nucleotide of a target nucleic acid. Typically, TALEs have been limited to the target nucleic acid sequences that they bind because the 5' nucleotide of the target site to which they bind is specified to be thymine (T). TALE domains with alternative 5' nucleotide specificities are described herein and expand the scope of DNA target sequences that can be bound by TALEs. Accordingly in some embodiments, the engineered TALE proteins provided herein bind a target sequence comprising an adenine (A) a cytosine (C), or a guanine (G) at the 5' end of a target sequence. In some embodiments, the TALE proteins provided herein bind a target sequence comprising a thymine (T) at the 5' end of a target sequence. In some embodiments the TALE proteins provided herein bind a target sequence comprising an adenine (A) a cytosine (C), or a guanine (G) at the 5' end of a target sequence with greater affinity as compared to the target sequence having a thymine (T) in place of the A, C or G at the 5' end of a target sequence. In some embodiments the TALE proteins provided herein bind a target sequence comprising an adenine (A) a cytosine (C), or a guanine (G) at the 5' end of a target sequence with at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 10%, at least 150%, at least 200%, at least 250%, at least 300%, at least 350%, at least 400%, at least 450%, or at least 500% greater affinity as compared to the target sequence having a thymine (T) in place of the A, C or G at the 5' end of a target sequence.

The affinity of the TALE protein to the target sequence may be determined by any suitable method known in the art. In some embodiments the affinity of the TALE protein to the target sequence is determined by measuring the binding affinity of the TALE protein to the target sequence. In some embodiments the affinity of the TALE protein to the target sequence is determined by indirectly measuring the binding affinity. For example, the binding affinity may be measured using an indirect readout such as expression of a nucleotide sequence (e.g., a gene), cleavage of a nucleotide sequence, or modification of a nucleotide sequence that is responsive to binding of the TALE protein to a target sequence. As one non-limiting example, a TALE protein comprising a transcriptional activator domain may induce transcription of a reporter gene (e.g., a fluorescent reporter gene) upon binding to a target sequence. Expression of the fluorescent reporter gene can be measured (e.g., based on fluorescence intensity) to determine the relative binding affinity of the TALE to one target sequence as compared to another target sequence.

In some embodiments, TALENs provided herein cleave their target sites with high specificity. For example, in some embodiments an engineered TALEN is provided that has been engineered to cleave a desired target site (e.g., within a genome) while binding and/or cleaving less than 1, less than 2, less than 3, less than 4, less than 5, less than 6, less than 7, less than 8, less than 9, less than 10, less than 20, or less than 50 off-target sites at a concentration effective for the nuclease to cut its intended target site within a genome. In some embodiments, a TALEN is provided that has been engineered to cleave a desired unique target site that has been selected to differ from any other site (e.g., within a genome) by at least 3, at least 4, at least 5, at least 6, at least 7, at least 8, at least 9, or at least 10 nucleotide residues. In some embodiments, a TALEN is provided that has been engineered to cleave a desired target site (e.g., within a genome) while binding and/or cleaving less than 1, less than 2, less than 3, less than 4, less than 5, less than 6, less than 7, less than 8, less than 9 or less than 10 off-target sites at a concentration effective for the nuclease to cut its intended target site. In some embodiments, a TALEN is provided that has been engineered to cleave a desired unique target site that has been selected to differ from any other site within a genome by at least 3, at least 4, at least 5, at least 6, at least 7, at least 8, at least 9, or at least 10 nucleotide residues.

In some embodiments, an engineered TALEN is provided that cleaves a target sequence more efficiently than one or more off-target sequences (e.g., in a genome). In some embodiments, an engineered TALEN is provided that cleaves a target sequence more efficiently by at least 0.1 fold, by at least 0.2 fold, by at least 0.3 fold, by at least 0.4 fold, by at least 0.5 fold, by at least 0.6 fold, by at least 0.7 fold, by at least 0.8 fold, by at least 0.9 fold, by at least 1 fold, by at least 2 fold, by at least 3 fold, by at least 4 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold as compared to one or more off-target sites (e.g., within a genome) at a concentration effective for the TALEN to cut its intended target site.

In some embodiments, the proteins provided herein comprise a TALE repeat array that binds a target sequence comprised in a genome. The term "genome", as used herein, refers to the genetic material of an organism. In some embodiments, the genome includes both the genes and the non-coding sequences of the genome. In some embodiments the genome comprises DNA. In some embodiments the genome comprises RNA. In some embodiments the genome comprises a eukaryotic genome, a prokaryotic genome, or a viral genome. In some embodiments, the genome comprises non-chromosomal genetic elements such as viruses, plasmids transposable elements. In some embodiments, the genome comprises genetic material stored within organelles that contain their own nucleic acids (e.g., mitochondria or chloroplasts).

In some embodiments, the genome is comprised in a cell. In some embodiments, the genome is comprised in a cell from an established cell line (e.g., a 293T cell), or a primary cell cultured ex vivo (e.g., cells obtained from a subject and grown in culture). In some embodiments, the genome is comprised in a hematologic cell (e.g., hematopoietic stem cell, leukocyte, or thrombocyte), or a cell from a solid tissue, such as a liver cell, a kidney cell, a lung cell, a heart cell, a bone cell, a skin cell, a brain cell, or any other cell found in a subject. In some embodiments, the genome or the cell comprising the genome is in a subject. Subjects comprising the genomes of the present disclosure include, but are not limited to, humans and/or other primates; mammals, including, but not limited to, cattle, pigs, horses, sheep, cats, dogs, mice, and/or rats; and/or birds, including commercially relevant birds such as chickens, ducks, geese, and/or turkeys.

The target sequence of any of the TALEs provided herein may bind a target sequence that is within a gene or in proximity to a gene known to be associated with a disease or disorder. In some embodiments, TALEs provided herein may be used for therapeutic purposes. For example, in some embodiments, TALEs provided herein may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc. In some embodiments, the TALE comprises an effector domain. For example, the effector domain may comprise a nuclease (e.g., a FokI domain). In some embodiments, the TALE (e.g., a TALEN) cleaves the target sequence upon dimerization of the nuclease domains when bound to the target sequence. In the context of TALENs, it should be appreciated that cleavage of a target site can occur upon dimerization of any of the TALENs described herein when bound to a target sequence. In some embodiments, the TALE comprises a transcriptional activator or repressor domain, a recombinase domain, or an epigenetic modification enzyme domain.

In some embodiments, a TALE provided herein cleaves a target site within an allele that is associated with a disease or disorder. In some embodiments, a TALE provided herein modulates expression of a gene associated with a disease or disorder when bound to a target site within the gene or in proximity to the gene. In some embodiments, the TALE cleaves a target site the cleavage of which results in the treatment or prevention of a disease or disorder. In some embodiments, the TALE binds a target site and modulates expression of a gene associated with a disease or disorder, which results in the treatment or prevention of the disease or disorder. In some embodiments, the disease is HIV/AIDS. In some embodiments, the disease is a proliferative disease. In some embodiments, the TALE binds a CCR5 target sequence (e.g., a CCR5 sequence associated with HIV). In some embodiments, the TALE binds an ATM target sequence (e.g., an ATM target sequence associated with ataxia telangiectasia). In some embodiments, the TALE binds a VEGFA target sequence (e.g., a VEGFA sequence associated with a proliferative disease). In some embodiments, the TALE binds a CFTR target sequence (e.g., a CFTR sequence associated with cystic fibrosis). In some embodiments, the TALE binds a dystrophin target sequence (e.g., a dystrophin gene sequence associated with Duchenne muscular dystrophy). In some embodiments, the TALE binds a CBX8 target sequence (e.g., a CBX8 sequence associated with a proliferative disease). In some embodiments, the TALE binds a target sequence associated with haemochromatosis, haemophilia, Charcot-Marie-Tooth disease, neurofibromatosis, phenylketonuria, polycystic kidney disease, sickle-cell disease, or Tay-Sachs disease. Suitable target genes, e.g., genes causing the listed diseases, are known to those of skill in the art. Additional genes and gene sequences associated with a disease or disorder will be apparent to those of skill in the art. Exemplary monogenic disease which can be targeted by the nucleases provided herein, and for which additional TALE or zinc finger nucleases could be evolved using the technology presented herein, include, but are not limited to any of the monogenic diseases listed at healthxchange.com.sg/News/Pages/Genetic-link-to-4000-diseases.aspx, and/or at genecards.org/cgi-bin/listdiseasecards.pl, the entire contents of each of which are incorporated herein by reference. In addition, in some embodiments, tractable polygenic diseases are embraced. The TALEs provided herein may modulate (e.g., increase, decrease or prevent) transcription of a gene when the TALE is bound to the target sequence. It should be appreciated that the target sequence may be within the gene or in proximity to the gene. When a TALE is bound to a target sequence in proximity to a gene, the TALE may modulate expression of the gene by regulating (e.g., promoting, or inhibiting) transcription of the gene (e.g., by binding a target sequence at or near a promoter sequence). Accordingly, in some embodiments, the TALE binds to a target sequence that is at least 1, at least 5, at least 10, at least 20, at least 50, at least 100, at least 200, at least 300, at least 400, at least 500, at least 600, at least 700, at least 800, at least 900, or at least 1000 nucleotides from the transcription start site of the gene to modulate expression of the gene. In some embodiments, the TALE protein increases transcription of the gene when the protein is bound to the target sequence. In some embodiments the TALE protein increases transcription of the gene by at least 1%, by at least 2%, by at least 5%, by at least 10%, by at least 15%, by at least 20%, by at least 25%, by at least 30%, by at least 35%, by at least 40%, by at least 45%, by at least 50%, by at least 60%, by at least 70%, by at least 80%, by at least 90%, by at least 100%, by at least 150%, or by at least 200% when the protein is bound to the target sequence. In some embodiments, the TALE protein decreases transcription of the gene when the protein is bound to the target sequence. In some embodiments the TALE protein decreases transcription of the gene by at least 1%, by at least 2%, by at least 5%, by at least 10%, by at least 15%, by at least 20%, by at least 25%, by at least 30%, by at least 35%, by at least 40%, by at least 45%, by at least 50%, by at least 60%, by at least 70%, by at least 80%, by at least 90%, or by at least 100% when the protein is bound to the target sequence.

In the context of nucleases that dimerize, for example, nucleases comprising a FokI DNA cleavage domain (e.g., TALENs), a target site typically comprises a left half-site (bound by one monomer of the nuclease), a right half-site (bound by the second monomer of the nuclease), and a spacer sequence between the half sites in which the cut is made. This structure ([left half-site]-[spacer sequence]-[right half-site]) is referred to herein as an LSR structure. In some embodiments, the left half-site and/or the right half-site is between 5-50 nucleotides long. In some embodiments, the left half-site and/or the right half-site is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. In some embodiments, both the left half-site and the right half-site are the same length. In some embodiments, either or both half-sites are shorter or longer. In some embodiments, the left and right half sites comprise different nucleic acid sequences. In some embodiments the target sequence comprises a left half-site. In some embodiments, the target sequence comprises a right half-site. In some embodiments, the target sequence comprises a left half-site and a right half-site. In some embodiments, the left half-site and/or the right half-site comprise an adenine (A), a cytosine (C), or a guanine (G) at the 5' position. In some embodiments, the left half-site and/or the right half-site comprise a thymine (T) at the 5' position.

Compositions

Also within the scope of the disclosure are compositions comprising any of the TALEs provided herein. In some embodiments, the composition comprises one or more of the TALEs provided herein. In some embodiments, the composition comprises the TALE nuclease (TALEN) monomer and a different TALE nuclease (TALEN) monomer that can form a heterodimer with the TALEN, wherein the dimer exhibits nuclease activity.

In some embodiments, the TALE is provided in a composition formulated for administration to a subject, e.g., to a human subject. For example, in some embodiments, a pharmaceutical composition is provided that comprises the TALE and a pharmaceutically acceptable excipient. In some embodiments, the pharmaceutical composition is formulated for administration to a subject. In some embodiments, the pharmaceutical composition comprises an effective amount of the TALE for cleaving a target sequence, for increasing transcription of a gene, for decreasing transcription of a gene or for preventing transcription of a gene in a cell in the subject. In some embodiments, the TALE binds a target sequence within a gene known to be associated with a disease or disorder and wherein the composition comprises an effective amount of the TALEN for alleviating a symptom associated with the disease or disorder.

For example, some embodiments provide pharmaceutical compositions comprising a TALE as provided herein, or a nucleic acid encoding such a TALE, and a pharmaceutically acceptable excipient. Pharmaceutical compositions may optionally comprise one or more additional therapeutically active substances.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21st Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a composition provided herein is administered to a subject, for example, to a human subject, in order to effect a targeted genomic modification within the subject. In some embodiments, cells are obtained from the subject and contacted with a nuclease or a nuclease-encoding nucleic acid ex vivo, and re-administered to the subject after the desired genomic modification has been effected or detected in the cells. Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with no more than routine experimentation. Subjects to which administration of the pharmaceutical compositions is contemplated include, but are not limited to, humans and/or other primates; mammals, including, but not limited to, cattle, pigs, horses, sheep, cats, dogs, mice, and/or rats; and/or birds, including commercially relevant birds such as chickens, ducks, geese, and/or turkeys.

In some embodiments, the TALEs, TALE domains, TALE-encoding or TALE domain-encoding nucleic acids, compositions, and reagents described herein are isolated. In some embodiments, the TALEs, TALE domains, TALE-encoding or TALE domain-encoding nucleic acids, compositions, and reagents described herein are purified, e.g., at least 60%, at least 70%, at least 80%, at least 90%, or at least 95% pure.

Modified TALE Domains and Proteins that Specifically Target CBX8

In some embodiments, the protein comprises an amino acid sequence that is at least 80% identical to the amino acid sequence provided in SEQ ID NO: 11, wherein the amino acid sequence comprises one of the amino acid substitutions or combination of amino acid substitutions selected from: A79E, P553L, and Q711P; A79E and L406F; A79E, L406F, and N425Y; A79E and Q711P; A79E, K226R, L406F, and Q711P; Q431P and Q711P; Q431P, Q711P, and P765S; T435A and Q711P; and D452G, E622K, and P689L; as compared to SEQ ID NO: 11.

In some embodiments, the protein comprises an amino acid sequence that is at least 80% identical to the amino acid sequence provided in SEQ ID NO: 11, wherein the amino acid sequence comprises one of the amino acid substitutions or combination of amino acid substitutions selected from: A79E and N562H; A79E, L508F, and K634R; A79E, L508F, and K634R; G138R and N629K; K226R and N629K; L508F and K634R; P587S and N629K; E622K and K634R; as compared to SEQ ID NO: 11.

In some embodiments, the protein comprises an amino acid sequence that is at least 80% identical to the amino acid sequence provided in SEQ ID NO: 11, wherein the amino acid sequence comprises one of the amino acid substitutions or combination of amino acid substitutions selected from: S62N, A125T, A412S, G565S, E622K, and V738G; A133G, H549L, D588N, and V738G; A133E, D588N, and V738G; A133G, D588N, and V738G; A133G, K396R and N683K; A133E, H549L, D588N, and V738G; A133E, K396R, and N683K; G117D, A169E, G565S, D582E, E622K, and V738G; T131A, P139S, N176T, K192R, G565S, E622K and V738G; P139S, L372F, G565S, P577S, E622K, and V738G; P139T, L372F, G565S, P577S, E622K, and V738G; K192R, G565S, E622K, and V738G; L270F, N629K, and V738G; and N631K and V738G; as compared to SEQ ID NO: 11.

In some embodiments, the protein comprises an amino acid sequence that is at least 80% identical to the amino acid sequence provided in SEQ ID NO: 11, wherein the amino acid sequence comprises one of the amino acid substitutions or combination of amino acid substitutions selected from: K27N, K59E, Q513K, N562H, E622K, V612G, Q711P, M758T, and V767G; K27N, K59E, P349L, Q513K, N562H, E622K, V612G, Q711P, M758T, and V767G; K59E, T280A, Q513K, N562H, E622K, Q711P, D746G, and V767G; and K59E, R61W, T280A, Q513K, N562H, E622K, Q711P, D746G, and V767G; as compared to SEQ ID NO: 11.

In some embodiments, the protein comprises an amino acid sequence that is at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to the amino acid sequence provided in SEQ ID NO: 11 comprising any of the amino acid substitutions or combination of amino acid substitutions provided herein.

In the context of CBX8-targeting TALEs that dimerize, for example, TALE nucleases comprising a FokI DNA cleavage domain (e.g., TALENs), a CBX8 target site typically comprises a left half-site (bound by one monomer of the nuclease), a right half-site (bound by the second monomer of the nuclease), and a spacer sequence between the half sites in which the cut is made. This structure ([left half-site]-[spacer sequence]-[right half-site]) is referred to herein as an LSR structure. In some embodiments, the left half-site comprises the nucleic acid sequence of SEQ ID NOs: 15, 17, 19, 21, or 23. In some embodiments, the left half site comprises the nucleic acid sequence of SEQ ID NOs: 16, 18, 20, 22, or 24. In some embodiments, the left half-site or right half-site comprises any of the nucleic acid sequences below:

```
CBX8 on target sequence with 5' T:
                                (SEQ ID NO: 36)
5'-TTCAGGAGGGCTTCGGC-'3

CBX8 on target sequence with 5' A:
                                (SEQ ID NO: 37)
5'-ATCAGGAGGGCTTCGGC-'3

CBX8 on target sequence with 5' C:
                                (SEQ ID NO: 38)
5'-CTCAGGAGGGCTTCGGC-'3

CBX8 on target sequence with 5'G:
                                (SEQ ID NO: 39)
5'-GTCAGGAGGGCTTCGGC-'3
```

```
-continued
CBX8 off-target sequence with 5'T:
                                (SEQ ID NO: 40)
5'-TTCATAAGGGATTAGGC-'3

CBX8 off-target sequence with 5'A:
                                (SEQ ID NO: 41)
5'-ATCATAAGGGATTAGGC-'3

CBX8 off-target sequence with 5'C:
                                (SEQ ID NO: 42)
5'-CTCATAAGGGATTAGGC-'3

CBX8 off-target sequence with 5'G:
                                (SEQ ID NO: 43)
5'-GTCATAAGGGATTAGGC-'3
```

Modified TALE Domains and Proteins that Specifically Target ATM

Some aspects of this disclosure are based on the recognition that certain modifications (e.g., mutations or amino acid substitutions) within ATM-targeting TALE proteins or ATM-targeting TALE domains increase the specificity of the ATM-targeting TALE protein to an ATM-target sequence relative to one or more off-target sequences. Accordingly, some aspects of this disclosure provide proteins with modified TALE N-terminal domains that target the ATM gene. The ATM gene encodes the ATM serine/threonine kinase and is also referred to as AT1, ATA, ATC, ATD, ATE, ATDC, TEL1, and TELO1. The protein encoded by the ATM gene belongs to the PI3/PI4-kinase family. Without wishing to be bound by any particular theory, this protein is a cell cycle checkpoint kinase that phosphorylates, and thus, regulates a wide variety of downstream proteins, including tumor suppressor proteins p53 and BRCA1, checkpoint kinase CHK2, checkpoint proteins RAD17 and RAD9, and DNA repair protein NBS1. This protein and the closely related kinase ATR are thought to be master controllers of cell cycle checkpoint signaling pathways that are required for cell response to DNA damage and for genome stability. Mutations in this gene are associated with ataxia telangiectasia, an autosomal recessive disorder. Accordingly, in some embodiments, the disclosure provides proteins comprising an amino acid sequence that is at least 80% identical to the amino acid sequence of SEQ ID NO: 1 comprising one or more of amino acid substitutions Q13R, A25E, W126C, and G132R as compared to SEQ ID NO: 1, or a homologous residue in a canonical N-terminal TALE domain. In some embodiments, the protein comprises one or more of amino acid substitutions: Q13R, A25E, W126C, and G132R as compared to SEQ ID NO: 1, or a homologous residue in a canonical N-terminal TALE domain.

Some aspects of this disclosure are based on the recognition that certain modifications (e.g., mutations or amino acid substitutions) within ATM-targeting TALE proteins or ATM-targeting TALE domains increase the specificity of the ATM-targeting TALE protein to an ATM target sequence relative to one or more off-target sequences. Accordingly, some aspects of this disclosure provide proteins that bind to an ATM target sequence with at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 10%, at least 150%, at least 200%, at least 250%, at least 300%, at least 350%, at least 400%, at least 450%, or at least 500% greater affinity as compared to an off-target sequence. The affinity of the ATM-targeting TALE protein to a target sequence may be determined by any suitable method known in the art. In some embodiments the affinity of the ATM-targeting TALE protein to the target sequence is determined by measuring the binding affinity of the ATM-targeting TALE protein to the target sequence. In some embodiments the affinity of the ATM-targeting TALE protein to the target sequence is determined by indirectly measuring the binding affinity. For example, the binding affinity is measured using an indirect readout such as expression of a nucleotide sequence (e.g., a gene), cleavage of a nucleotide sequence, or modification of a nucleotide sequence that is responsive to binding of the ATM-targeting TALE protein to a target sequence.

In some embodiments, the ATM-targeting TALE protein comprises a TALEN. In some embodiments, the ATM-targeting TALEN provided is a monomer. In some embodiments, the ATM-targeting TALEN monomer can dimerize with another ATM-targeting TALEN monomer to form an ATM-targeting TALEN dimer. In some embodiments the formed dimer is a homodimer. In some embodiments, the dimer is a heterodimer.

In some embodiments, the proteins of the present disclosure comprise an amino acid sequence that is at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to SEQ ID NO: 1. In some embodiments, the proteins of the present disclosure comprise one or more of amino acid substitutions Q13R, A25E, W126C, and G132R as compared to SEQ ID NO: 1 or a homologous residue in a canonical N-terminal TALE domain. It should be appreciated that the proteins of the present disclosure may comprise one, or any combination of amino acid substitutions including: Q13R, A25E, W126C, and G132R as compared to SEQ ID NO: 1, or a homologous residue in a canonical N-terminal TALE domain.

In some embodiments, the ATM target sequence comprises the nucleic acid sequence TGAATTGGGATGCTGTTT (SEQ ID NO: 15) and/or the nucleic acid sequence TTTATTTTACTGTCTTTA (SEQ ID NO: 16). In some embodiments, the ATM target sequence comprises a left half-site and/or a right half-site. In some embodiments, the left half-site comprises the nucleic acid sequence of (SEQ ID NO: 15). In some embodiments, the right half site comprises the nucleic acid sequence of (SEQ ID NO: 16). The ATM target sequence, in some embodiments, comprises an LSR structure. An LSR structure has a left half-site (which may bind one monomer of a TALE protein), a right half-site (which may bind a second monomer of a TALE protein), and a spacer sequence between the half sites. In the context of TALE nucleases (TALENs), the spacer sequence may be cut by the nuclease. In some embodiments, the ATM target sequence comprises the structure ([left half-site]-[spacer sequence]-[right half-site]). The spacer sequence may be any suitable length for use in accordance with any of the methods provided herein. In some embodiments, the spacer sequence is from 2 nucleotides to 100 nucleotides in length. In some embodiments, the spacer sequence is form 5 to 30 nucleotides in length. In some embodiments, the spacer sequence is 5, 6, 7, 8, 9, 10, 11, 12, 13, 14, 15, 16, 17, 18, 19, 20, 21, 22, 23, 24, 25, 26, 27, 28, 29, or 30 nucleotides in length. In some embodiments the spacer sequence comprises the nucleic acid sequence TTAGGTATTCTATTCAAA (SEQ ID NO: 25). In some embodiments, the ATM target site comprises the nucleic acid sequence of SEQ ID NO: 35 (TGAATTGGGATGCTGTTTTTAGGTATTCTATTCAAATTTATTTTACTGTCTTTA.

In some embodiments, the ATM target site comprises a left half-site. In some embodiments, the ATM left half-site comprises the nucleic acid sequence of any one of SEQ ID NOs: 17, 19, 21, or 23. In some embodiments, the ATM target site comprises a right half-site. In some embodiments, the ATM right half-site comprises the nucleic acid sequence of any one of SEQ ID NOs: 18, 20, 22, or 24.

In some embodiments, the protein comprises an amino acid sequence that is at least 80% identical to the amino acid sequence provided in SEQ ID NO: 13, wherein the amino acid sequence comprises one of the amino acid substitutions or combination of amino acid substitutions selected from Q53R and A252T; W166C, K260R, A398S, A514T, A592V, and Q745P; A252T, Q505K, and Q745P; and A252T, L338S, Q505K, and Q745P; as compared to SEQ ID NO: 13.

In some embodiments, the protein comprises an amino acid sequence that is at least 80% identical to the amino acid sequence provided in SEQ ID NO: 13, wherein the amino acid sequence comprises one of the amino acid substitutions or combination of amino acid substitutions selected from A65E and E815G; G172R and A252T; W166C, A398S, A514T, A592V, and P611Q; W166C, A398S, A514T, A592V, and K688R; A252T, K464R, and A568V; and D310E, V640I, and L644F; as compared to SEQ ID NO: 13.

In some embodiments, the protein comprises an amino acid sequence that is at least 80% identical to the amino acid sequence provided in SEQ ID NO: 13, wherein the amino acid sequence comprises one of the amino acid substitutions or combination of amino acid substitutions selected from A252T, Q505K, R506K, Q745P, and A789V; A252T, Q505K, Q745P, and A789V; and A252T, L338S, Q505K, Q745P, and A789V; as compared to SEQ ID NO: 13.

In some embodiments, the protein comprises an amino acid sequence that is at least 80% identical to the amino acid sequence provided in SEQ ID NO: 13, wherein the amino acid sequence comprises one of the amino acid substitutions or combination of amino acid substitutions selected from Q53R and A252T; or A252T, L338S, Q505K, and Q745P as compared to SEQ ID NO: 13.

In some embodiments, the protein comprises an amino acid sequence that is at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to the amino acid sequence provided in SEQ ID NO: 13 comprising any of the amino acid substitutions provided herein.

Some aspects of this disclosure are based on the recognition that certain modifications (e.g., mutations or amino acid substitutions) within ATM targeting TALE proteins or ATM targeting TALE arrays increase the specificity of the ATM targeting TALE protein to an ATM target sequence relative to one or more off-target sequences. Accordingly, some aspects of this disclosure provide proteins with modified TALE repeat arrays. In some embodiments, the disclosure provides proteins comprising an amino acid sequence that is at least 80% identical to the amino acid sequence of SEQ ID NO: 12 comprising one or more of amino acid substitutions A76T, K84R, D134E, L162S, A222S, K288R, Q329K, R330K, A338T, A392V, A416V, P435Q, V464I, L468F, and K512R as compared to SEQ ID NO: 12.

In some embodiments, the proteins of the present disclosure comprise an amino acid sequence is at least 82% identical, at least 84% identical, at least 86% identical, at least 88% identical, at least 90% identical, at least 92% identical, at least 94% identical, at least 95% identical, at least 96% identical, at least 97% identical, at least 98% identical, or at least 99% identical to SEQ ID NO: 12. In some embodiments, the proteins of the present disclosure comprise a TALE repeat array comprising one or more of the amino acid substitutions or combination of amino acid substitutions selected from A76T; A76T and Q329K; A76T, L162S, and Q329K; and K84R, A222S, A338T, and A416V; as compared to SEQ ID NO: 12. In some embodiments, the proteins of the present disclosure comprise a TALE repeat array comprising one or more of the amino acid substitutions or combination of amino acid substitutions selected from A76T; A76T, K288R, and A392V; D134E, V464I, and L468F; A222S, A338T, A416V, and P435Q; and A222S, A338T, A416V, and K512R; as compared to SEQ ID NO: 12. In some embodiments, the proteins of the present disclosure comprise a TALE repeat array comprising one or more of the amino acid substitutions or combination of amino acid substitutions selected from: A76T, Q329K and R330K; A76T and Q329K; A76T, L162S, and Q329K; and A76T and Q329K; as compared to SEQ ID NO: 12. In some embodiments, the proteins of the present disclosure comprise a TALE repeat array comprising one or more of the amino acid substitutions or combination of amino acid substitutions selected from A76T; and A76T, L162S, and Q329K; as compared to SEQ ID NO: 12.

Expression Constructs

Some aspects of this disclosure provide nucleic acids encoding any of the TALEs provided herein. In some embodiments, the nucleic acids encoding the TALEs are under the control of a heterologous promoter. In some embodiments, the encoding nucleic acids are included in an expression construct, e.g., a plasmid, a viral vector, or a linear expression construct. In some embodiments, the nucleic acid or expression construct is in a cell, tissue, or organism.

Nucleic acids encoding any of the proteins, described herein, may be in any number of nucleic acid "vectors" known in the art. As used herein, a "vector" means any nucleic acid or nucleic acid-bearing particle, cell, or organism capable of being used to transfer a nucleic acid into a host cell. The term "vector" includes both viral and nonviral products and means for introducing the nucleic acid into a cell. A "vector" can be used in vitro, ex vivo, or in vivo. Non-viral vectors include plasmids, cosmids, artificial chromosomes (e.g., bacterial artificial chromosomes or yeast artificial chromosomes) and can comprise liposomes, electrically charged lipids (cytofectins), DNA-protein complexes, and biopolymers, for example. Viral vectors include retroviruses, lentiviruses, adeno-associated virus, pox viruses, baculovirus, reoviruses, vaccinia viruses, herpes simplex viruses, Epstein-Barr viruses, and adenovirus vectors, for example. Vectors can also comprise the entire genome sequence or recombinant genome sequence of a virus. A vector can also comprise a portion of the genome that comprises the functional sequences for production of a virus capable of infecting, entering, or being introduced to a cell to deliver nucleic acid therein.

Expression of any of the proteins, described herein, may be controlled by any regulatory sequence (e.g. a promoter sequence) known in the art. Regulatory sequences, as described herein, are nucleic acid sequences that regulate the expression of a nucleic acid sequence. A regulatory or control sequence may include sequences that are responsible for expressing a particular nucleic acid (e.g., a nucleic acid encoding a TALE) or may include other sequences, such as heterologous, synthetic, or partially synthetic sequences.

The sequences can be of eukaryotic, prokaryotic or viral origin that stimulate or repress transcription of a gene in a specific or non-specific manner and in an inducible or non-inducible manner. Regulatory or control regions may include origins of replication, RNA splice sites, introns, chimeric or hybrid introns, promoters, enhancers, transcriptional termination sequences, poly A sites, locus control regions, signal sequences that direct the polypeptide into the secretory pathways of the target cell, and introns. A heterologous regulatory region is not naturally associated with the expressed nucleic acid it is linked to. Included among the heterologous regulatory regions are regulatory regions from a different species, regulatory regions from a different gene, hybrid regulatory sequences, and regulatory sequences that do not occur in nature, but which are designed by one of ordinary skill in the art.

The term operably linked refers to an arrangement of sequences or regions wherein the components are configured so as to perform their usual or intended function. Thus, a regulatory or control sequence operably linked to a coding sequence is capable of affecting the expression of the coding sequence. The regulatory or control sequences need not be contiguous with the coding sequence, so long as they function to direct the proper expression or polypeptide production. Thus, for example, intervening untranslated but transcribed sequences can be present between a promoter sequence and the coding sequence and the promoter sequence can still be considered operably linked to the coding sequence. A promoter sequence, as described herein, is a DNA regulatory region a short distance from the 5' end of a gene that acts as the binding site for RNA polymerase. The promoter sequence may bind RNA polymerase in a cell and/or initiate transcription of a downstream (3' direction) coding sequence. The promoter sequence may be a promoter capable of initiating transcription in prokaryotes or eukaryotes. Some non-limiting examples of eukaryotic promoters include the cytomegalovirus (CMV) promoter, the chicken β-actin (CBA) promoter, and a hybrid form of the CBA promoter (CBh).

Kits

Some aspects of this disclosure provide kits comprising an engineered TALE or TALE domain as provided herein, a cloning vector that encodes an engineered TALE or TALE domain as provided herein, or a composition (e.g., a pharmaceutical composition) comprising such a TALE. In some embodiments, the kit comprises a cloning vector comprising a nucleic acid sequence that encodes any of the engineered N-terminal TALE domains, any of the engineered C-terminal TALE domains, and/or any of the TALE repeat arrays provided herein. In some embodiments, the kit comprises a cloning vector comprising a nucleic acid sequence that encodes an engineered N-terminal TALE domain, and/or an engineered C-terminal TALE domain, provided herein. Such cloning vectors may be used to clone (e.g., using standard molecular biology techniques) in any TALE repeat array to specifically target any sequence of interest. In some embodiments, the kit comprises an excipient and instructions for contacting the TALE with the excipient to generate a composition suitable for contacting a nucleic acid with the TALE. In some embodiments, the excipient is a pharmaceutically acceptable excipient.

Typically, the kit will comprise a container housing the components of the kit, as well as written instructions stating how the components of the kit should be stored and used.

Methods

Some aspects of this disclosure provide methods for phage-assisted, continuous evolution of a DNA binding domains. In some embodiments, the methods comprise a negative selection against an undesired activity of the DNA-binding domain, e.g., a binding activity towards an off-target site. Such negative selection strategies can be used to improve the specificity of a DNA binding domain being evolved, e.g., in that binding to off-target sites is minimized or abolished. In some embodiments, the methods comprise a negative selection against a plurality of undesired activities, e.g., against binding activity towards a plurality of off-target sites. In some embodiments, the methods comprise a negative selection that is performed simultaneous to a positive selection, e.g., in a lagoon comprising host cells harboring both a positive and a negative selection construct, or in a lagoon harboring different host cells, e.g., host cells comprising a positive selection construct and host cells harboring a negative selection construct. In some embodiments, a plurality of negative selections is carried out simultaneously, e.g., in a lagoon comprising host cells harboring a plurality of different negative selection constructs, or in a lagoon harboring different host cells comprising different negative selection constructs. In some embodiments, the negative selection comprises a selection, either sequentially or simultaneously, against at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, or at least 100 different off-target sites.

In some embodiments, the methods for phage-assisted, continuous evolution of a DNA binding domain comprise identifying of-target sites that the DNA binding domain binds to. In some embodiments, such off-target sites are identified using high-throughput methods, e.g., library screening methods that identify off-target sites bound by the DNA binding domain from a library of candidate binding sites. Suitable library screening methods are disclosed herein, and additional suitable methods will be apparent to those of skill in the art based on the present disclosure. Exemplary suitable high-throughput methods for identifying off-target binding sites include, without limitation, those disclosed in International Patent Application WO2013/066438, the entire contents of which are incorporated herein by reference.

In some embodiments, the methods for phage-assisted, continuous evolution of a DNA binding domain provided herein comprise (a) contacting a flow of host cells through a lagoon with a selection phage comprising a nucleic acid sequence encoding a DNA-binding domain to be evolved, and (b) incubating the selection phage or phagemid in the flow of host cells under conditions suitable for the selection phage to replicate and propagate within the flow of host cells, and for the nucleic acid sequence encoding the DNA-binding domain to be evolved to mutate. In some embodiments, the host cells are introduced through the lagoon at a flow rate that is faster than the replication rate of the host cells and slower than the replication rate of the phage, thereby permitting replication and propagation of the selection phage in the lagoon. In some embodiments, the flow of host cells comprises a plurality of host cells harboring a positive selection construct comprising a nucleic acid sequence encoding a gene product essential for the generation of infectious phage particles, wherein the gene product essential for the generation of infectious phage particles is expressed in response to a desired DNA-binding activity of the DNA-binding domain to be evolved or an evolution product thereof. In some embodiments, the selection phage does not comprise a nucleic acid sequence encoding the gene product essential for the generation of infectious phage particles. In some embodiments, the flow of host cells comprises a plurality of host cells harboring a negative selection construct comprising a nucleic acid sequence encoding a dominant negative gene product that decreases or abolishes the production of infectious phage particles, wherein the dominant negative gene product is expressed in response to an undesired activity of the DNA-binding domain to be evolved or an evolution product thereof.

Some aspects of this disclosure provide methods for improving the specificity of a DNA-binding domain by phage-assisted, continuous evolution. The method comprises, in some embodiments, (a) contacting a flow of host cells through a lagoon with a selection phage comprising a nucleic acid sequence encoding a DNA-binding domain to be evolved, and (b) incubating the selection phage or phagemid in the flow of host cells under conditions suitable for the selection phage to replicate and propagate within the flow of host cells, and for the nucleic acid sequence encoding the DNA-binding domain to be evolved to mutate. In some embodiments, the host cells are introduced through the lagoon at a flow rate that is faster than the replication rate of the host cells and slower than the replication rate of the phage, thereby permitting replication and propagation of the selection phage in the lagoon. In some embodiments, the flow of host cells comprises a plurality of host cells harboring a negative selection construct comprising a nucleic acid sequence encoding a dominant negative gene product that decreases or abolishes the production of infectious phage particles, wherein the dominant negative gene product is expressed in response to an undesired activity of the DNA-binding domain to be evolved or an evolution product thereof.

In some embodiments of the PACE methods disclosed herein, the positive selection construct and/or the negative selection construct is comprised on an accessory plasmid. In some embodiments, the flow of host cells comprises a plurality of different negative selection constructs, wherein in each different negative selection construct, the dominant negative gene product is expressed in response to a different undesired activity of the DNA-binding domain to be evolved or an evolution product thereof. In some embodiments, the different negative selection constructs are comprised in different host cells within the flow of host cells.

In some embodiments, the method further comprises (i) identifying a plurality of undesired activities of the DNA-binding domain to be evolved or an evolution product thereof, and (ii) providing a plurality of different negative selection construct selecting against different undesired activities identified in (i), wherein each different negative selection construct selects against a different undesired activity. In some embodiments, the undesired activity is DNA-binding of an off-target sequence. In some embodiments, the identifying of (i) comprises performing a high-throughput screen of candidate off-target sequences.

In some embodiments, the dominant negative gene product is expressed in response to DNA-binding of an off-target sequence by the DNA-binding domain to be evolved or an evolution product thereof. In some embodiments, the different negative selection constructs comprise different off-target sequences. In some embodiments, the DNA-binding domain is a TALE domain.

The scope of this disclosure also embraces methods of using the TALEs provided herein. It will be apparent to those of skill in the art that the TALEs provided herein can be used in any method suitable for the application of TALEs, including, but not limited to, those methods and applications known in the art. Such methods may include TALE-mediated modulation of gene expression or TALE-mediated cleavage of DNA, e.g., in the context of genome manipulations such as, for example, targeted gene knockout through non-homologous end joining (NHEJ) or targeted genomic sequence replacement through homology-directed repair (HDR) using an exogenous DNA template, respectively. The improved features of the TALEs provided herein, e.g., the improved specificity of some of the TALEs provided herein, will typically allow for such methods and applications to be carried out with greater efficiency. For example, and without limitation, the instant disclosure provides the use of the TALENs provided herein in any method suitable for the use of TALEs (e.g., TALENs) as described in Boch, Jens (February 2011). "TALEs of genome targeting". Nature Biotechnology 29 (2): 135-6. doi:10.1038/nbt.1767. PMID 21301438; Boch, Jens; et. al. (December 2009). "Breaking the Code of DNA Binding Specificity of TAL-Type III Effectors". Science 326 (5959): 1509-12. Bibcode: 2009Sci . . . 326.1509B. doi:10.1126/science.1178811. PMID 19933107; Moscou, Matthew J.; Adam J. Bogdanove (December 2009). "A Simple Cipher Governs DNA Recognition by TAL Effectors". Science 326 (5959): 1501. Bibcode:2009Sci . . . 326.1501M. doi:10.1126/science.1178817. PMID 19933106; Christian, Michelle; et. al. (October 2010). "Targeting DNA Double-Strand Breaks with TAL Effector Nucleases". Genetics 186 (2): 757-61. doi:10.1534/genetics.110.120717. PMC 2942870. PMID 20660643; Li, Ting; et. al. (August 2010). "TAL nucleases (TALNs): hybrid proteins composed of TAL effectors and FokI DNA-cleavage domain". Nucleic Acids Research 39: 1-14. doi:10.1093/nar/gkq704. PMC 3017587. PMID 20699274; Mahfouz, Magdy M.; et. al. (February 2010). "De novo-engineered transcription activator-like effector (TALE) hybrid nuclease with novel DNA binding specificity creates double-strand breaks". PNAS 108 (6): 2623-8. Bibcode:2011PNAS . . . 108.2623M. doi:10.1073/pnas.1019533108. PMC 3038751. PMID 21262818; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". Nucleic Acids Research. doi:10.1093/nar/gkr218; Miller, Jeffrey; et. al. (February 2011). "A TALE nuclease architecture for efficient genome editing". Nature Biotechnology 29 (2): 143-8. doi:10.1038/nbt.1755. PMID 21179091; Hockemeyer, D.; Wang, H.; Kiani, S.; Lai, C. S.; Gao, Q.; Cassady, J. P.; Cost, G. J.; Zhang, L. et al. (2011). "Genetic engineering of human pluripotent cells using TALE nucleases". Nature Biotechnology 29 (8). doi:10.1038/nbt.1927; Wood, A. J.; Lo, T.-W.; Zeitler, B.; Pickle, C. S.; Ralston, E. J.; Lee, A. H.; Amora, R.; Miller, J. C. et al. (2011). "Targeted Genome Editing Across Species Using ZFNs and TALENs". Science 333 (6040): 307. doi:10.1126/science.1207773. PMC 3489282. PMID 21700836; Tesson, L.; Usal, C.; Ménoret, S. V.; Leung, E.; Niles, B. J.; Remy, S. V.; Santiago, Y.; Vincent, A. I. et al. (2011). "Knockout rats generated by embryo microinjection of TALENs". Nature Biotechnology 29 (8): 695. doi:10.1038/nbt.1940; Huang, P.; Xiao, A.; Zhou, M.; Zhu, Z.; Lin, S.; Zhang, B. (2011). "Heritable gene targeting in zebrafish using customized TALENs". Nature Biotechnology 29 (8): 699. doi:10.1038/nbt.1939; Doyon, Y.; Vo, T. D.; Mendel, M. C.; Greenberg, S. G.; Wang, J.; Xia, D. F.; Miller, J. C.; Urnov, F. D. et al. (2010) "Enhancing zinc-finger-nuclease activity with improved obligate heterodimeric architectures". Nature Methods 8 (1): 74-79. doi:10.1038/nmeth.1539. PMID 21131970; Szczepek, M.; Brondani, V.; Büchel, J.; Serrano, L.; Segal, D. J.; Cathomen, T. (2007). "Structure-based redesign of the dimerization interface reduces the toxicity of zinc-finger nucleases". Nature Biotechnology 25 (7): 786. doi:10.1038/nbt1317. PMID 17603476; Guo, J.; Gaj, T.; Barbas Iii, C. F. (2010). "Directed Evolution of an Enhanced and Highly Efficient FokI Cleavage Domain for Zinc Finger Nucleases". Journal of Molecular Biology 400 (1): 96. doi:10.1016/j.jmb.2010.04.060. PMC 2885538. PMID 20447404; Mussolino, C.; Morbitzer, R.; Lutge, F.; Dannemann, N.; Lahaye, T.; Cathomen, T. (2011). "A novel TALE nuclease scaffold enables high genome editing activity in combination with low toxicity". Nucleic Acids Research. doi:10.1093/nar/gkr597; Zhang, Feng; et. al. (February 2011). "Efficient construction of sequence-specific TAL effectors for modulating mammalian transcription". Nature Biotechnology 29 (2): 149-53. doi:10.1038/nbt.1775. PMC 3084533. PMID 21248753; Morbitzer, R.; Elsaesser, J.; Hausner, J.; Lahaye, T. (2011). "Assembly of custom TALE-type DNA binding domains by modular cloning". Nucleic Acids Research. doi:10.1093/nar/gkr151; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". Nucleic Acids Research. doi:10.1093/nar/gkr188; Geiβler, R.; Scholze, H.; Hahn, S.; Streubel, J.; Bonas, U.; Behrens, S. E.; Boch, J. (2011). "Transcriptional Activators of Human Genes with Programmable DNA-Specificity". In Shiu, Shin-Han. PLoS ONE 6 (5): e19509. doi:10.1371/journal.pone.0019509; Weber, E.; Gruetzner, R.; Werner, S.; Engler, C.; Marillonnet, S. (2011). "Assembly of Designer TAL Effectors by Golden Gate Cloning". In Bendahmane, Mohammed. PLoS ONE 6 (5): e19722. doi:10.1371/journal.pone.0019722; Sander et al. "Targeted gene disruption in somatic zebrafish cells using engineered TALENs". Nature Biotechnology Vol 29:697-98 (5 Aug. 2011) Sander, J. D.; Cade, L.; Khayter, C.; Reyon, D.; Peterson, R. T.; Joung, J. K.; Yeh, J. R. J. (2011). "Targeted gene disruption in somatic zebrafish cells using engineered TALENs". Nature Biotechnology 29 (8): 697. doi:10.1038/nbt.1934; the entire contents of each of which are incorporated herein by reference.

Aspects of the disclosure embrace methods for using any of the TALE proteins provided herein. In some embodiments, the methods include contacting a nucleic acid molecule, comprising a target sequence, with a TALE protein provided herein under conditions suitable for the protein to bind the target sequence. In some embodiments, the method comprises contacting the nucleic acid molecule in vitro. In some embodiments, the method comprises contacting the nucleic acid molecule in vivo. In some embodiments, the method comprises contacting the nucleic acid molecule in a cell. In some embodiments, the cell is a cell in vitro. In some embodiments, the cell is a cell in a subject. In some embodiments, the method comprises contacting the nucleic acid molecule in a subject. In some embodiments, the nucleic acid molecule is comprised in a genome. In some embodiments, the target sequence is comprised in or is in proximity to a gene known to be associated with a disease or disorder. In some embodiments, the disease or disorder is a proliferative disease or disorder. In some embodiments, the proliferative disease or disorder is cancer. In some embodiments, the gene associated with a disease or disorder is CBX8, ATM or CCR5. In some embodiments, the disease or disorder is acquired immunodeficiency syndrome (AIDS), or a human immunodeficiency virus (HIV) infection. In some embodiments, the target sequence comprises a left half-site. In some embodiments, the target sequence comprises a right half-site. In some embodiments, the target sequence comprises a left half-site and a right half-site. In some embodiments, the left half-site and/or the right half-site comprise an adenine (A), a cytosine (C), or a guanine (G) at the 5' position. In some embodiments, the left half-site and/or the right half-site comprise a thymine (T) at the 5' position. In some embodiments, the protein comprises an effector domain. In some embodiments, the effector domain comprises a nuclease domain (e.g., a FokI domain). In some embodiments, the nuclease domain is a FokI nuclease domain and/or wherein the protein is a TALEN. In some embodiments, the protein cleaves the target sequence when the protein is bound to the target sequence. In some embodiments, the protein dimerizes to cleave the target sequence. In some embodiments, the effector domain comprises a transcriptional activator or repressor domain, a recombinase domain, or an epigenetic modification enzyme domain. In some embodiments, the protein modulates transcription of the gene known to be associated with a disease or disorder. In some embodiments, the protein increases transcription of the gene known to be associated with a disease or disorder. In some embodiments, the protein decreases transcription of the gene known to be associated with a disease or disorder. In some embodiments, the protein prohibits transcription of the gene known to be associated with a disease or disorder.

In some embodiments, the methods of the present disclosure include administering any of the proteins, provided herein, to a subject having or diagnosed with a disease or disorder in an amount effective to ameliorate at least one symptom of the disease or disorder. In some embodiments, the disease or disorder is a proliferative disease. In some embodiments, the disease or disorder is cancer. In some embodiments, the disease or disorder is acquired immunodeficiency syndrome (AIDS), or a human immunodeficiency virus (HIV) infection. In some embodiments, the disease or disorder is a monogenic disease that is associated with a genetic defect in a single gene that can be addressed with a nuclease, e.g., a TALEN, or a ZFN.

EXAMPLES

Introduction

A system was developed that enables proteins to evolve continuously in the laboratory with virtually no researcher intervention[31]. The resulting system, phage-assisted continuous evolution (PACE), allows proteins to undergo directed evolution at a rate ~100-fold faster than conventional methods (FIG. 1A). During PACE, host E. coli cells continuously dilute an evolving population of filamentous bacteriophages ("selection phage", SP) in a fixed-volume vessel (a "lagoon"). Dilution occurs faster than cell division but slower than phage replication, ensuring that only the phage can accumulate mutations. Each SP carries an evolving gene instead of gene III, an essential phage gene that is required for infection. Phage encoding active variants trigger host-cell expression of gene III from the "accessory plasmid" (AP) and produce infectious progeny, while phage encoding less active variants produce non-infectious progeny that are diluted out of the lagoon. PACE has been used to rapidly evolve RNA polymerases and proteases with tailor-made properties[31-35]. It was tested whether the PACE system could be adapted to evolve DNA-binding domains with altered or improved DNA-binding specificity.

Presented herein is a general system for the continuous evolution of DNA-binding domains, DNA-binding PACE (DB-PACE). Using the previously described PACE platform as a starting point, described herein, is the development of positive and negative PACE selections for DNA binding, optimization of host cell flow rates and background activity levels, and integration of these advances to enable for the first time the continuous evolution of DNA-binding activity. The system was validated by evolving restored DNA-binding activity in mutated zinc fingers. The system was then applied to evolve TALEs that prefer a non-canonical 5' nucleotide (A, C, or G) over the native 5' T. Finally, this system was used to evolve TALE proteins with enhanced DNA specificity by selecting variants that maintain on-target DNA binding but lose affinity for their most highly cleaved off-target site in human cells. The improved DNA cleavage specificity of the corresponding TALENs was verified both in vitro using high-throughput specificity profiling, and in human cells. The results establish DB-PACE as a new strategy for tuning the affinity and specificity of DBDs including genome-editing proteins, identify substitutions in TALE proteins that determine DNA-binding preferences, and expand the scope of continuous protein evolution.

Example 1 Development of a PACE System for DNA-Binding Activity

Figure 1B:
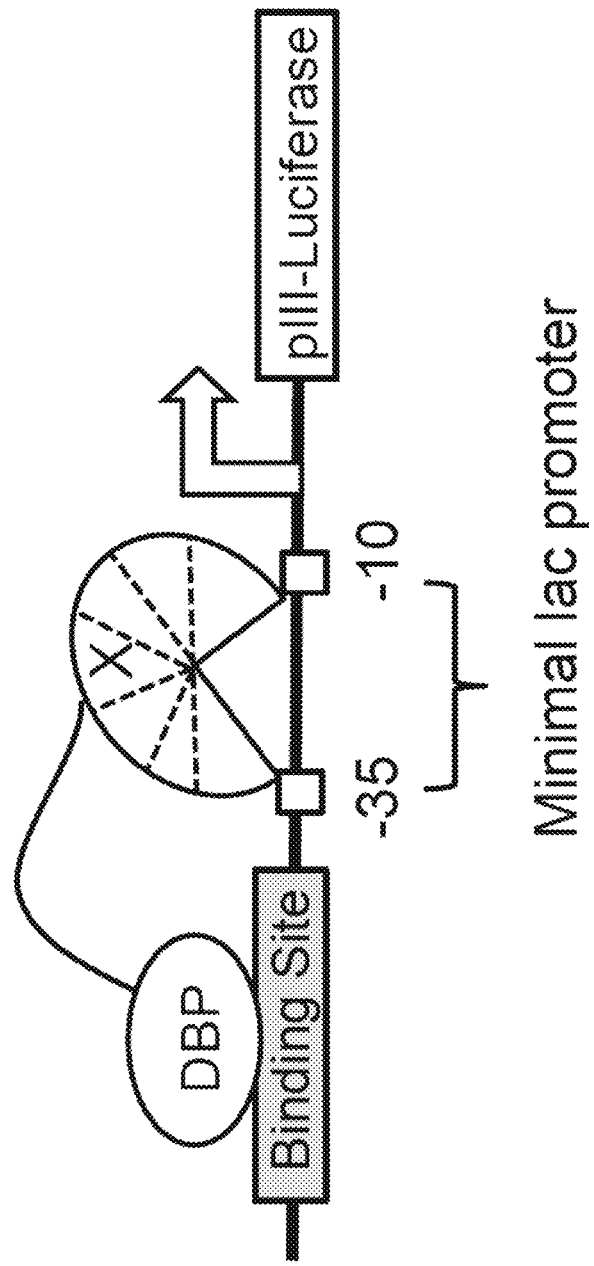
Figure 1C:
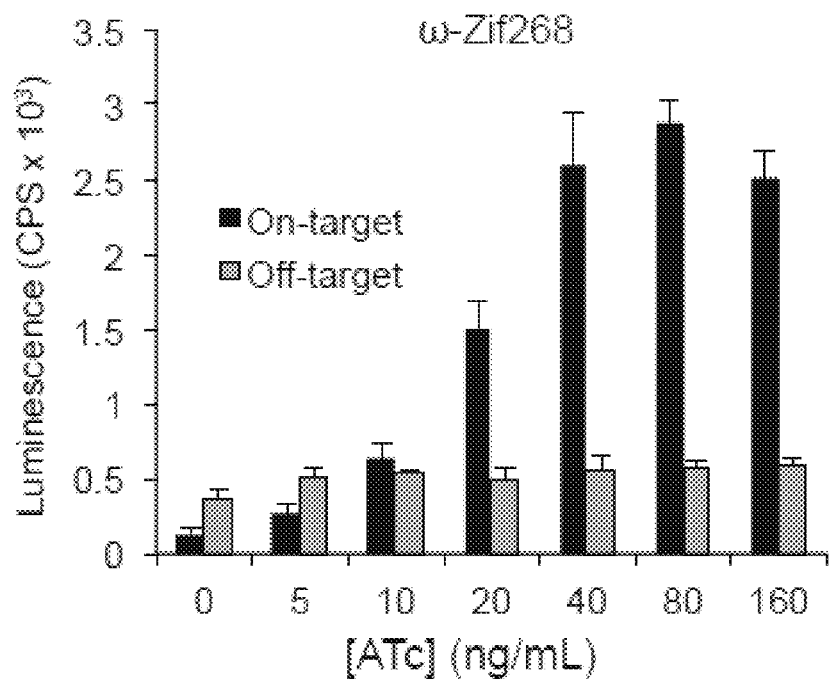
Figure 1D:
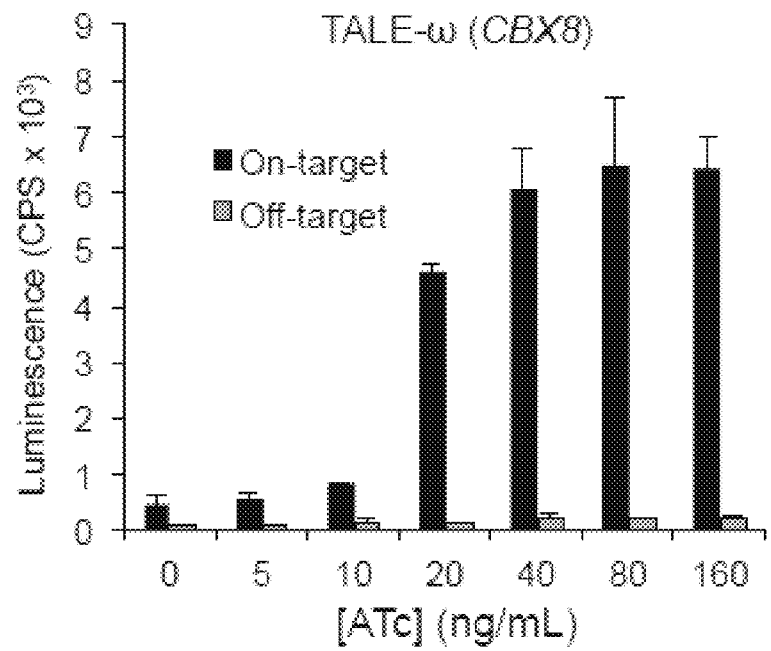
Figure 5A:
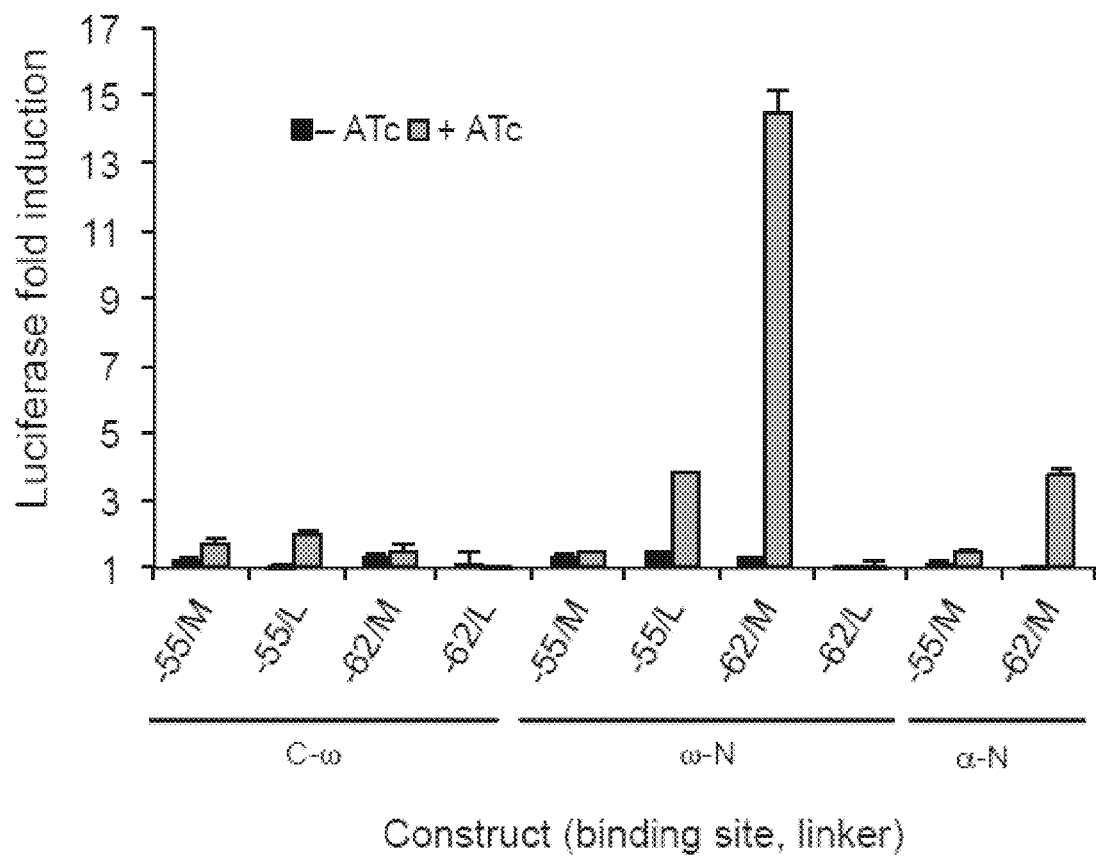
FIG. 5A shows the optimization of a one-hybrid architecture for PACE. Comparison of pIII-luciferase fold induction (ATc-induced Zif268 expression/non-induced luminescence) resulting from binding of a Zif268 fusion with either the α or ω subunit of RNAP to a Zif268 operator sequence (5'-GCGTGGGCG-3'; SEQ ID NO: 48) centered at either −55 or −62. M refers to a medium-length linker between Zif268 and the RNAP subunit (AAATSGGGGAA (SEQ ID NO: 52)), and L refers to a longer linker (AAGGGGSGGGGSGGGGSTAAA (SEQ ID NO: 53)). Data represent mean+s.d. (n=3).
Figure 6A:
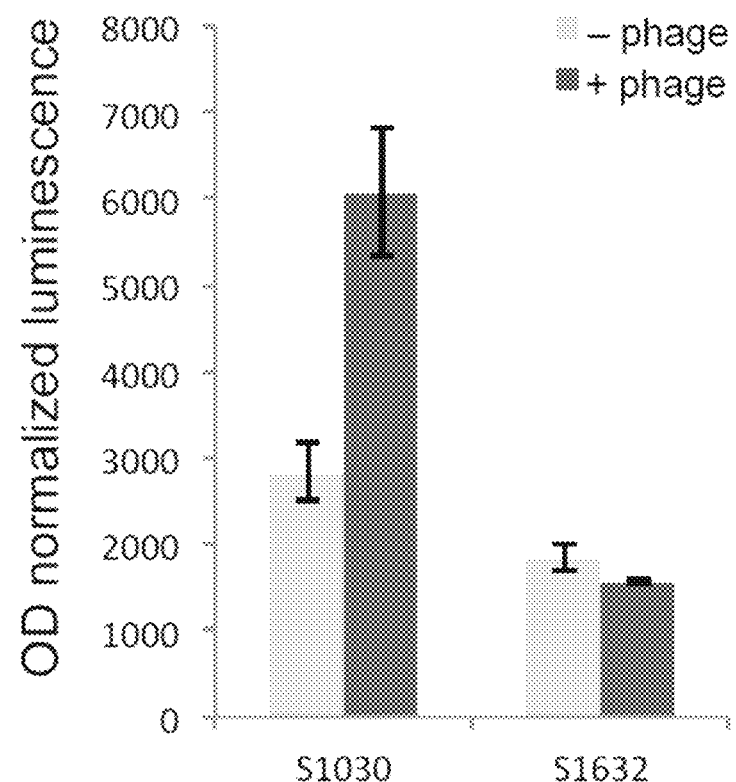
FIGS. 6A-6B show that chromosomal pspBC deletion enables small-molecule control of the phage shock promoter response.
Figure 6B:
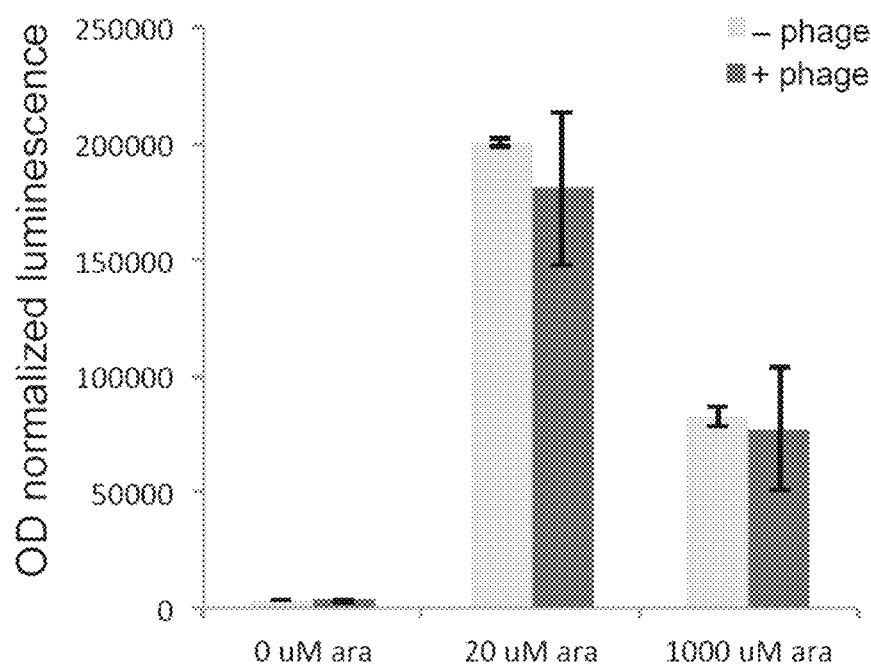
Figure 7A:
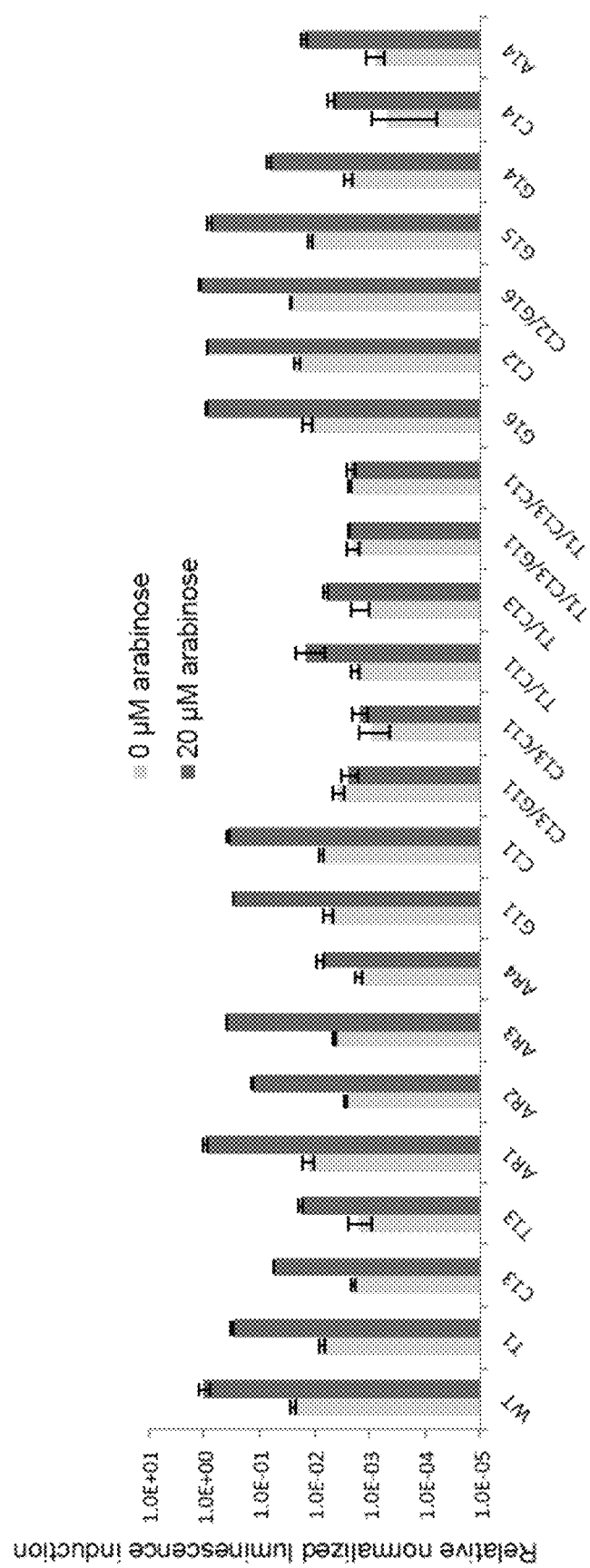
FIGS. 7A-7C show the generation of mutant PSP variants with altered dynamic range. Mutants abrogating the efficiency or background transcription of the PSP were constructed and tested through low-level expression of the phage shock sensors pspBC, which are master inducers of the phage shock response. Mutations were constructed based on prior knowledge of the PSP architecture[57] and σ54 promoter activities[58]. Generally, mutations were focused on the σ54 core promoter. The "AR" series carried additional mutations to reduce the strength of σ70 cryptic promoters that may influence background transcription levels.
Figure 7B:
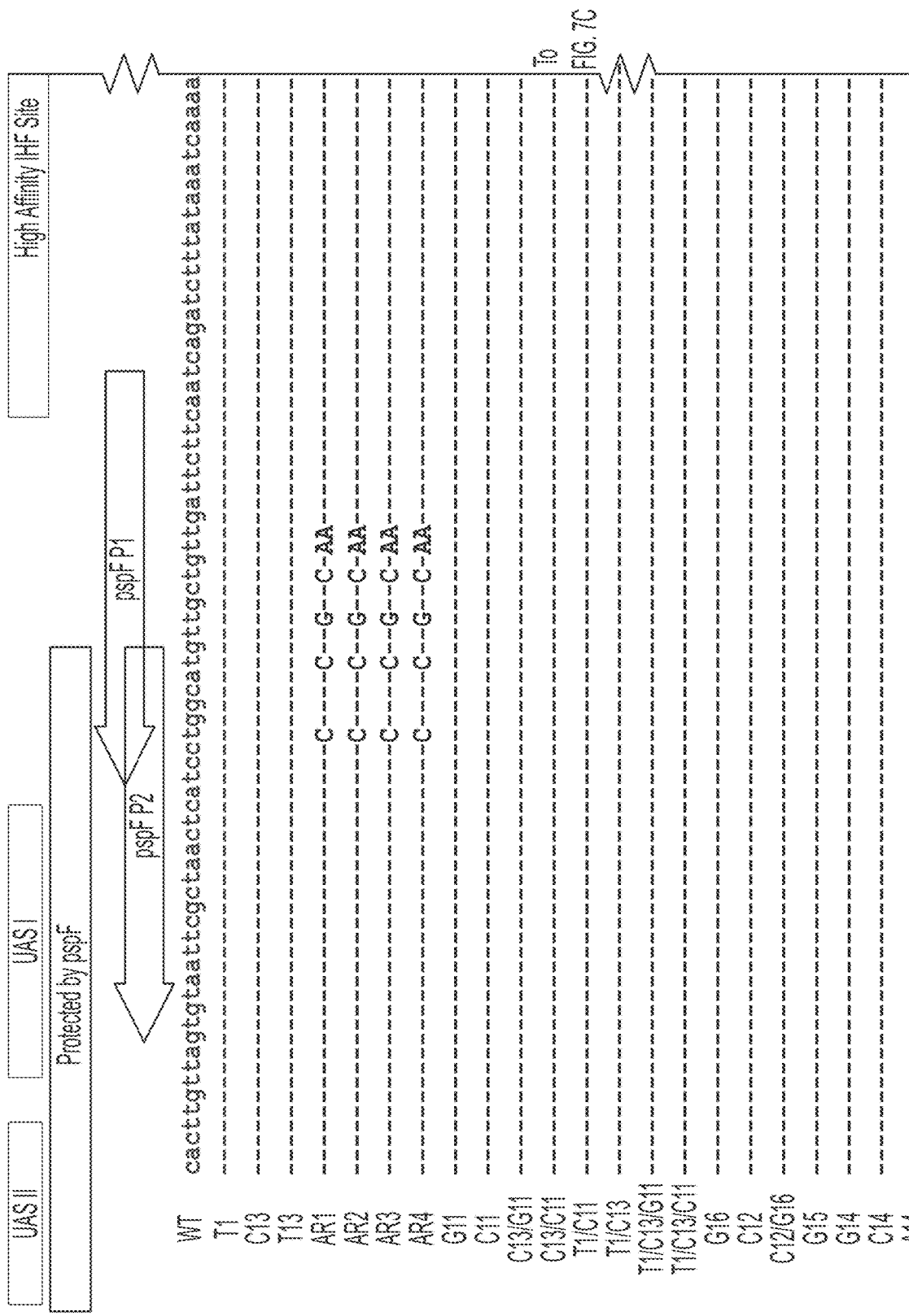
Figure 7C:
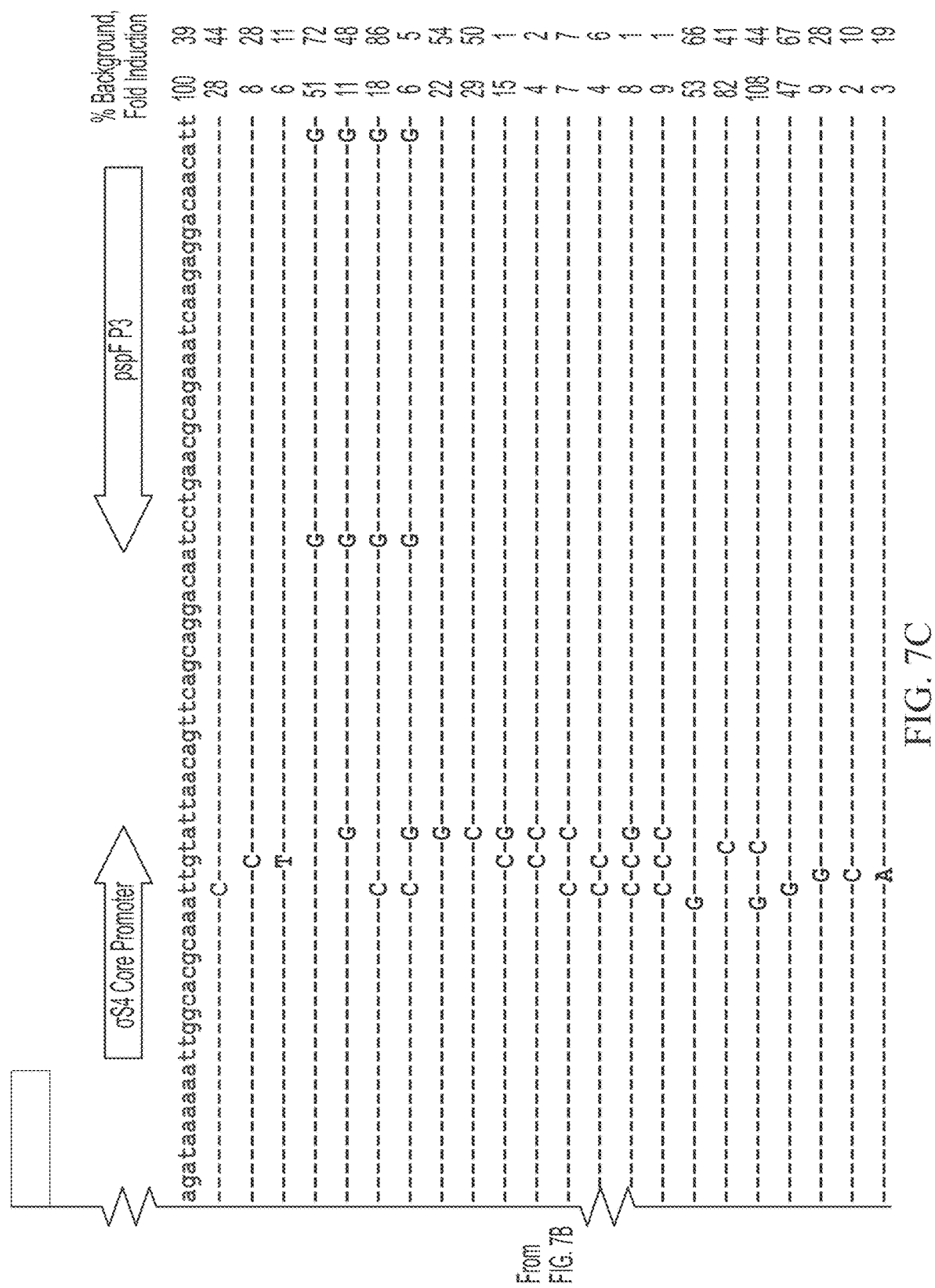
Figure 8A:
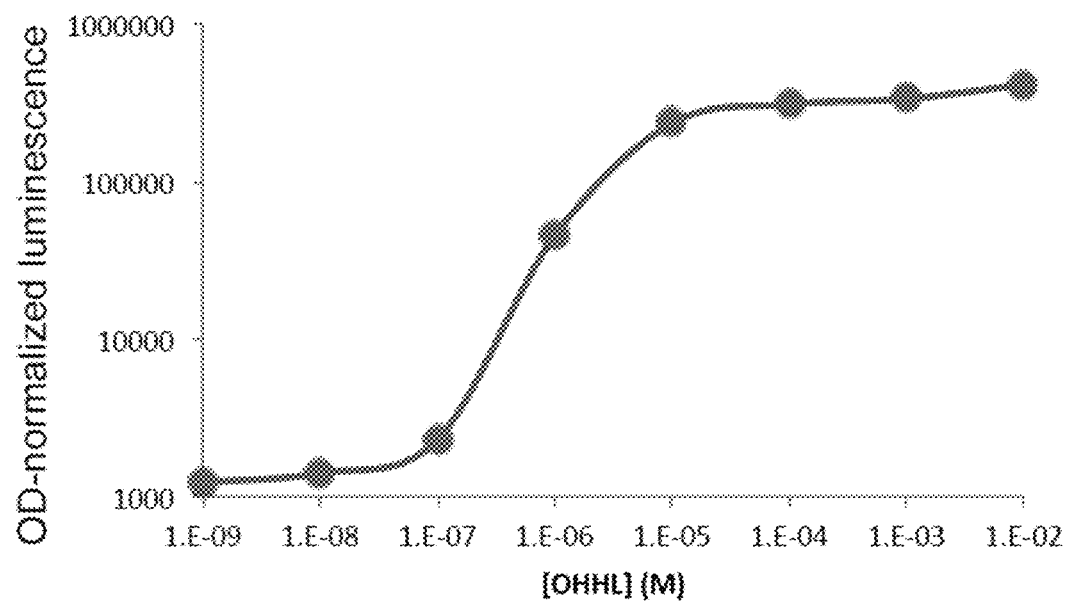
FIGS. 8A-8C show the generation of S2060, a bacterial strain for chaperone overexpression and robust visualization of phage plaques.
Figure 8B:
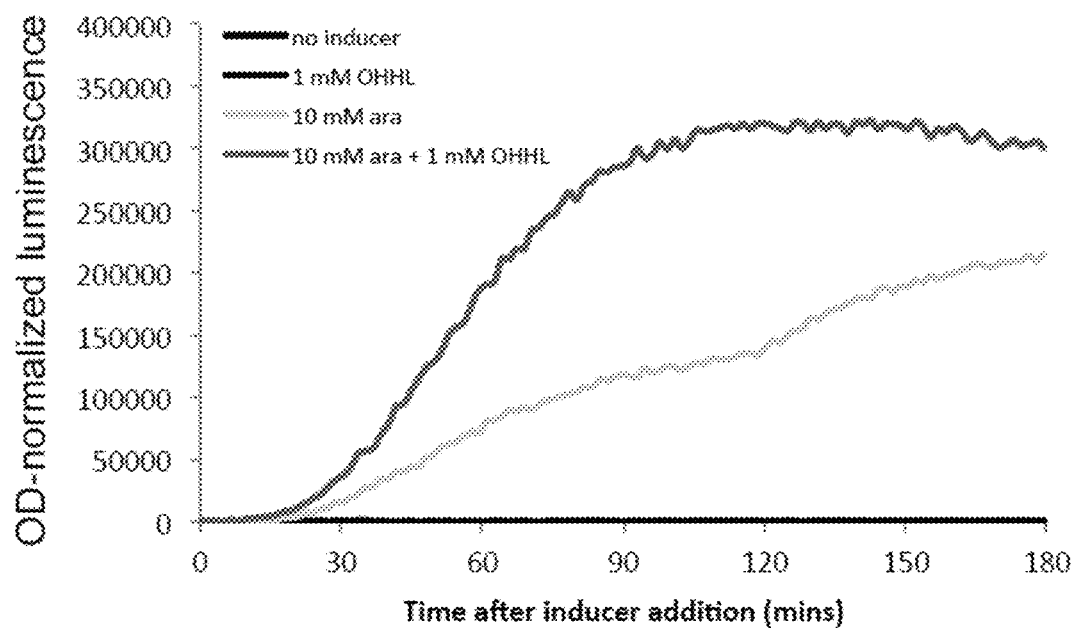
Figure 8C:
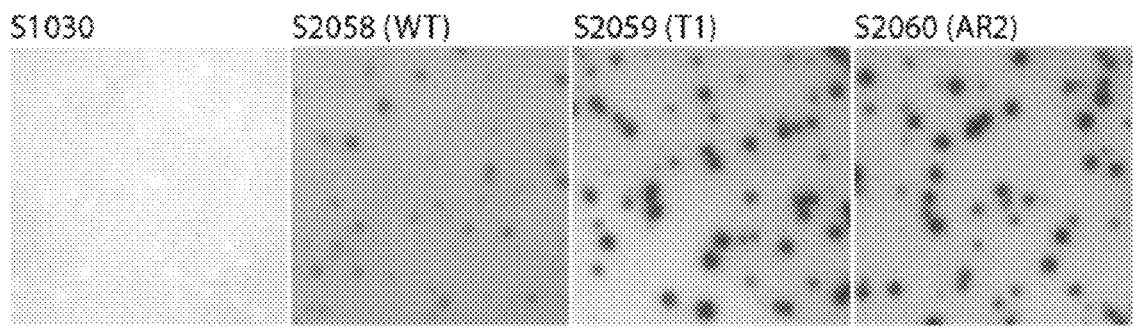

To develop a PACE-compatible DNA-binding selection, a DNA-binding domain of interest was linked to a subunit of bacterial RNA polymerase III (RNAP). It was intended that binding of this fusion protein to operator sequences upstream of a minimal lac promoter would induce transcription of a downstream gene III-luciferase reporter through recruitment or stabilization of the RNAP holoenzyme (FIG. 1B). To validate this strategy, an assay was developed that transduces cognate DNA-binding of the DBD from Zif268 (residues 333-420)[37], expressed from a tetracycline-inducible promoter, into activation of pIII-luciferase expression. This assay was used to evaluate a variety of DNA operator locations (at −55 and −62 bp with respect to the transcription initiation site)[36,38] and RNA polymerase fusion architectures. Fusing the RNAP ω subunit to the N-terminus of Zif268 with an 11-residue linker resulted in ≥10-fold increase in pIII-luciferase production when the consensus Zif268 binding site (5'-GCGTGGGCG-3'; SEQ ID NO: 48) was positioned at −62 (FIG. 5A). To test the DNA specificity of this system, a control construct with an off-target Zif268 binding site was created in which the middle triplet of the target DNA site was changed to 5'-TTA-3'[10]. Only E. coli containing the reporter downstream of the on-target sequence, but not those containing the off-target sequence, produced pIII-luciferase (FIG. 1C), establishing sequence-specific and DNA binding-dependent gene expression.

Figure 9A:
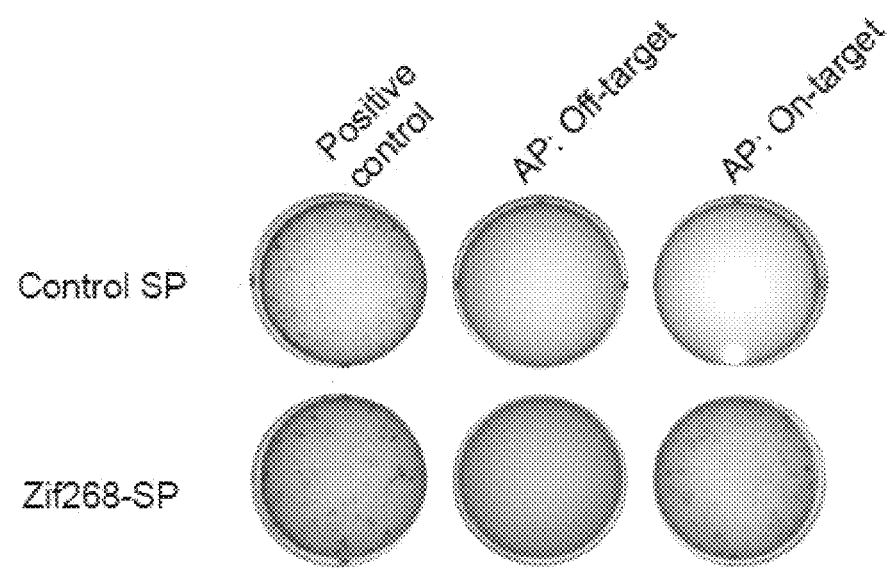
Figure 9B:
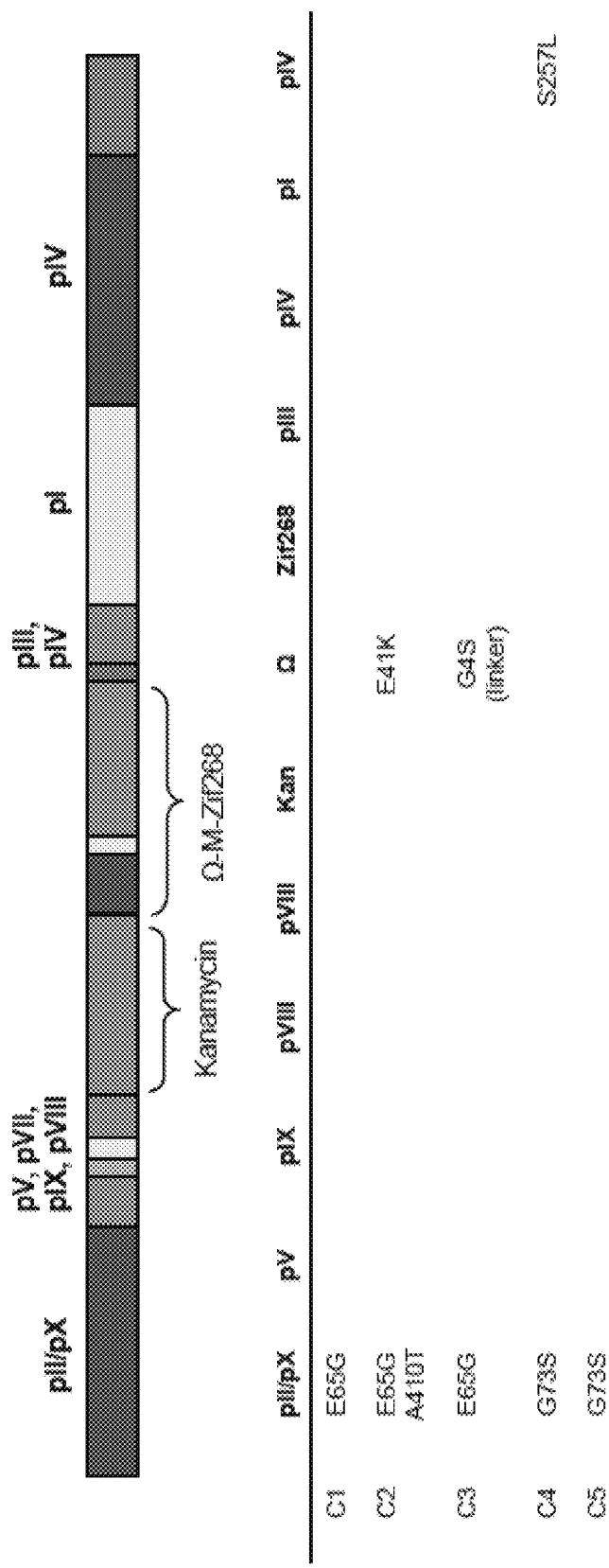

To integrate this system into PACE, the DNA operator-gene III-luciferase cassette was moved to an AP, and moved the RNAP ω-Zif268 protein to an SP. Next, an E. coli strain designated S2060 was developed capable of inducing LacZ in response to activation of the phage shock promoter, a transcriptional regulatory element that responds to a number of environmental signals including filamentous phage infection (FIGS. 6A-8C). This strain can be used in combination with colorimetric LacZ substrates such as X-gal to stain bacteria that have been infected with phage. It was tested whether ω-Zif268-SP could propagate in a DNA-binding activity-dependent manner on S2060 cells containing an AP with the cognate Zif268 binding sequence, or a mutated binding sequence. A robust formation of colored plaques was observed, indicative of phage propagation, on cells harboring the on-target AP, but not on cells harboring an AP containing the off-target sequence (FIG. 9A). These observations demonstrate DNA binding activity-dependent phage propagation. Next, an initial PACE experiment was performed to optimize the SP backbone. SPs encoding Zif268 in PACE over 24 h were continuously propagated on host cells carrying the cognate AP plasmid and a mutagenesis plasmid (MP)[31]. After 24 h of PACE, the surviving SPs contained mutations in the phage genes encoding pII/X and pIV, and the fusion protein linker (FIG. 9B). These results collectively establish a basis for the continuous evolution of DBDs using PACE.

To validate the ability of this positive selection PACE system to improve DNA-binding activity, the system was used to evolve DNA binding in an inactive Zif268 mutant protein. Mutation of Arg24 in Zif268 to a small hydrophobic residue is known to abrogate DNA binding[40]. A lagoon was seeded with inactive ω-Zif268 SP containing an R24V mutation. After 24 h of neutral drift (mutation in the absence of any selection pressure) followed by 24 h of PACE on host cells containing the cognate AP, the evolved SPs were capable of propagating on the target AP (FIG. 9C). All of the sequenced phage clones at the end of the 24-h PACE experiment contained the V24R reversion mutation using an Arg codon not present in the wild-type gene (AGA vs. CGC) (FIG. 9D). Collectively, these results validate that this system can rapidly evolve proteins with DNA-binding activity.

Example 2: Continuous Evolution of TALE 5' Specificity

Figure 10A:
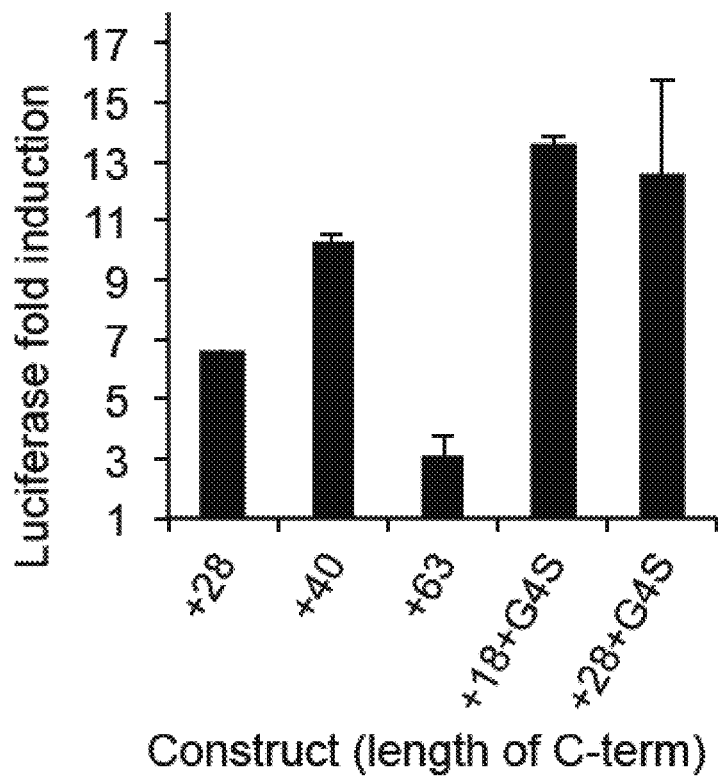
Figure 10B:
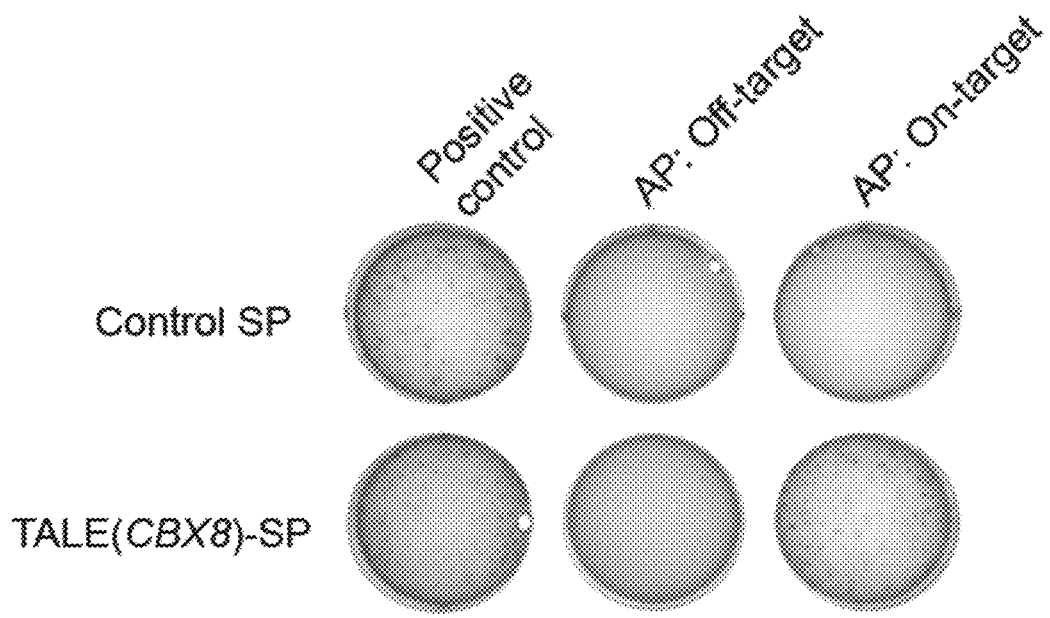

This system was used to continuously evolve TALE proteins with novel properties. A series of C-terminal fusions between a previously reported TALE array targeting CBX8 (right half-site TALE)[18], and the RNAP ω subunit were tested. Fusions using a linker of 18 or 28 amino acids of the natural TALE C-terminus followed by a GGGGS sequence resulted in >10-fold gene activation in a luciferase assay (FIG. 10A). The sequence specificity of the system was verified using an off-target sequence in the luciferase assay, and performed on- and off-target colorimetric plaque assays using TALE-ω SP and host cells harboring the AP containing the target CBX8 sequence. Similar to the findings with zinc fingers, both luciferase expression and phage propagation were dependent on the presence of the cognate TALE binding site (FIG. 10B). Finally, PACE was performed for 24 h on the cognate AP to optimize the SP backbone. This experiment resulted in several mutations in the phage genome, as well as an A8V substitution in the ωRNAP subunit (FIG. 10C). These observations collectively suggest the applicability of DB-PACE to TALE proteins.

Figure 2A:
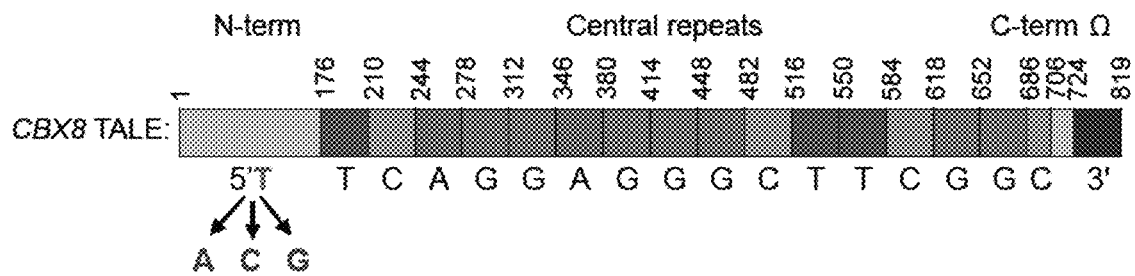
FIGS. 2A-2D show the continuous evolution of TALEs with altered 5' base specificity.
Figure 10D:
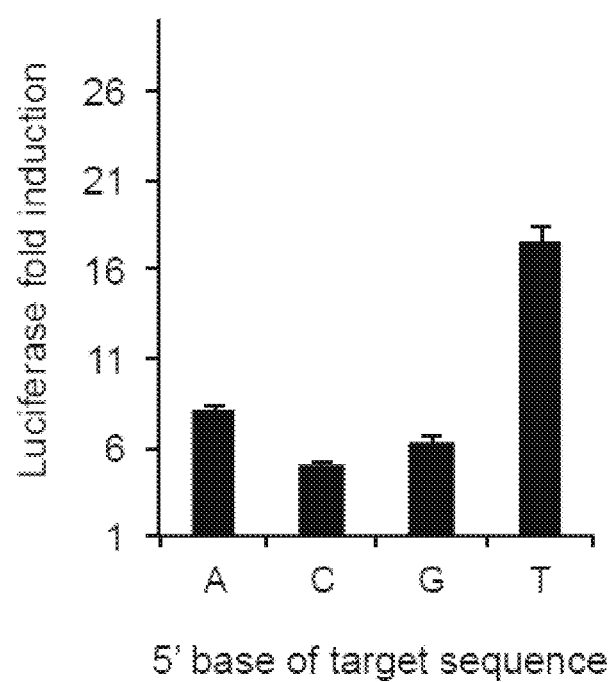

One of the limitations of canonical TALE arrays is that target sequences must begin with a 5' T for optimal binding[13,14]. PACE was used to evolve TALE proteins with altered 5' nucleotide preferences, both to expand the DNA sequences that can be targeted with TALEs without compromising DNA-binding activity, and to illuminate TALE domain structure-function relationships that contribute to 5' specificity. The 5' DNA specificity of the CBX8-targeting TALE was examined using the gene III-luciferase reporter assay. We observed 2- to 3-fold higher luciferase induction for 5' T over the other bases (FIG. 10D). Next, APs were created in which the 5' base of the cognate sequence was changed to 5' A, 5' C, or 5' G, and initiated three parallel PACE experiments to evolve TALEs with increased DNA-binding activity for each of these sequences (FIG. 2A). For each experiment, we performed selections in duplicate lagoons (L1 and L2). Following 48 h of PACE, we isolated phage with up to 6-fold increased activity on 5' A relative to the canonical TALE protein (FIG. 2B), 5-fold increased activity on 5' C (FIG. 11A), and 5-fold higher activity on 5' G target sequences (FIG. 11B).

Figure 2B:
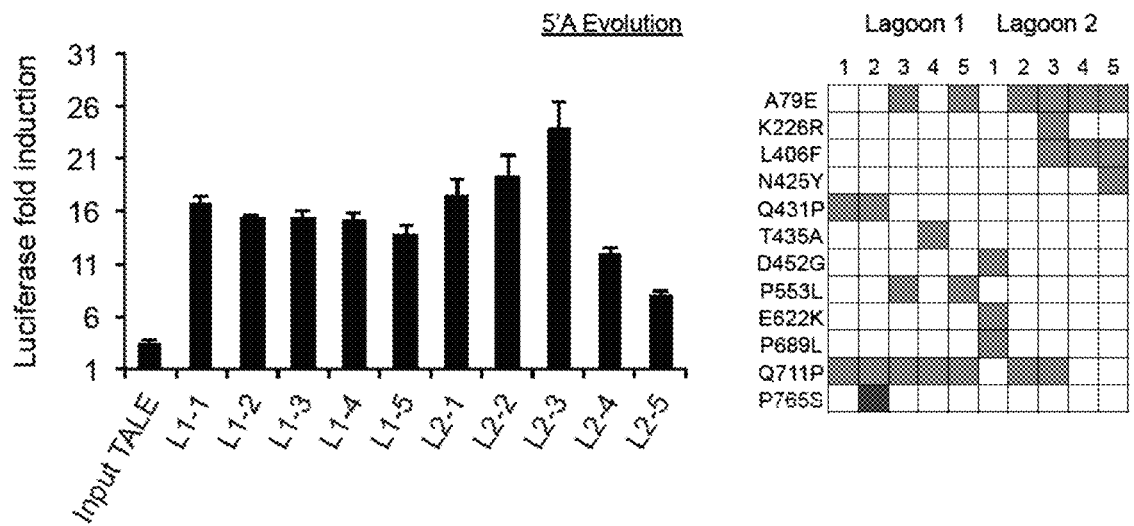
Figure 11A:
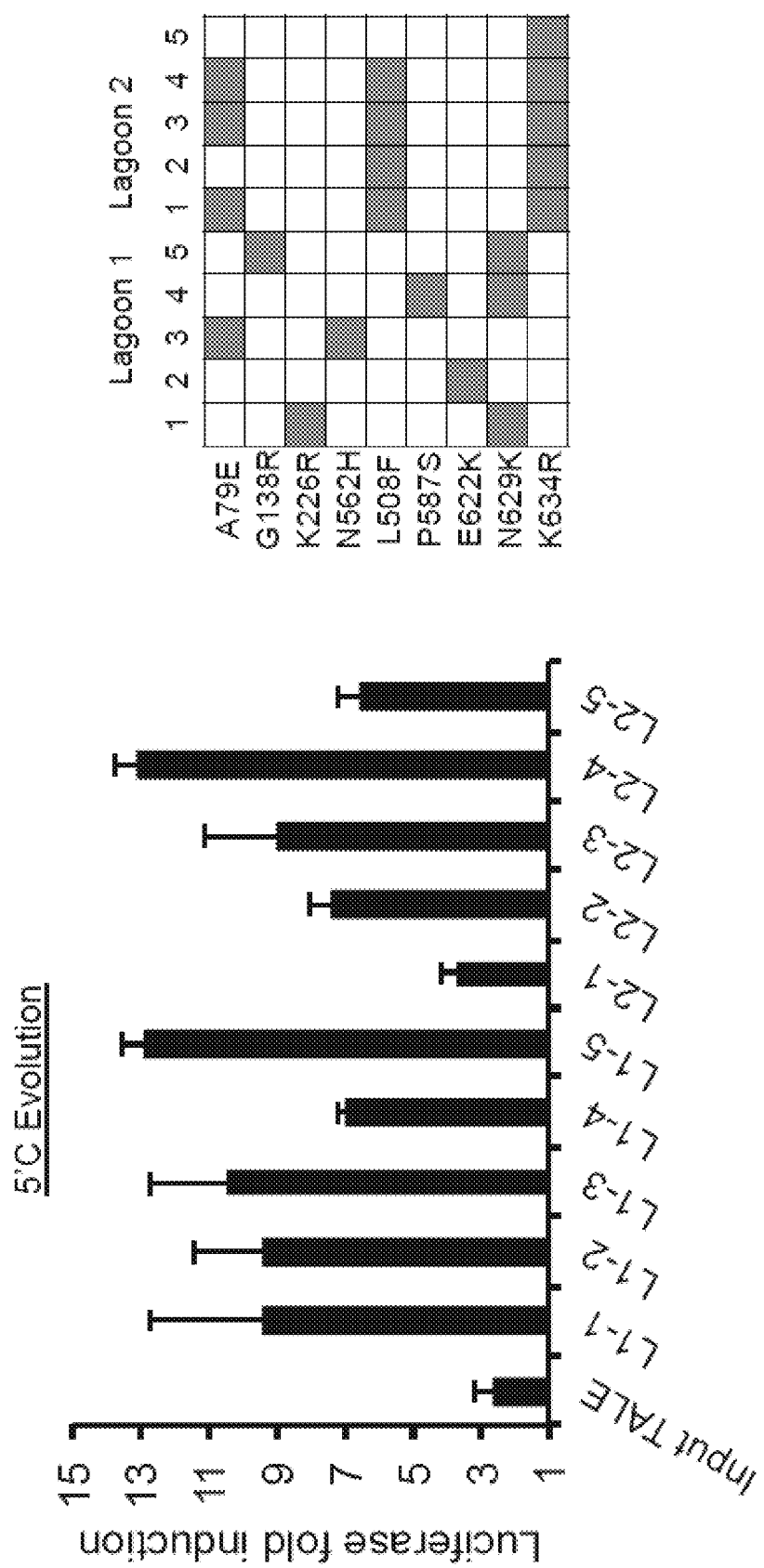
FIGS. 11A-11B show the evolution of CBX8-TALE variants with increased activity towards 5' C or 5' G sequences. The left panel of FIG. 11A depicts luciferase activity shown as fold induction (ATc-induced TALE luminescence/non-induced luminescence) for the canonical TALE (input TALE) and five PACE-evolved clones from either lagoon 1 (L1) or lagoon 2 (L2) evolved to bind a CBX8-target sequence beginning with 5' C. The right panel of FIG. 11A shows the genotypes for the clones shown in the left panel. The left panel in FIG. 11B is identical to FIG. 11A, but with clones evolved to bind a CBX8-target sequence beginning with 5' G. The right panel of FIG. 11B shows genotypes for the clones shown in the left panel. For FIGS. 11A-11B, blue shaded squares indicate mutations within the TALE domain, and green shaded squares indicate mutations within the ω subunit, and data show mean+s.d. (n=3).
Figure 11B:
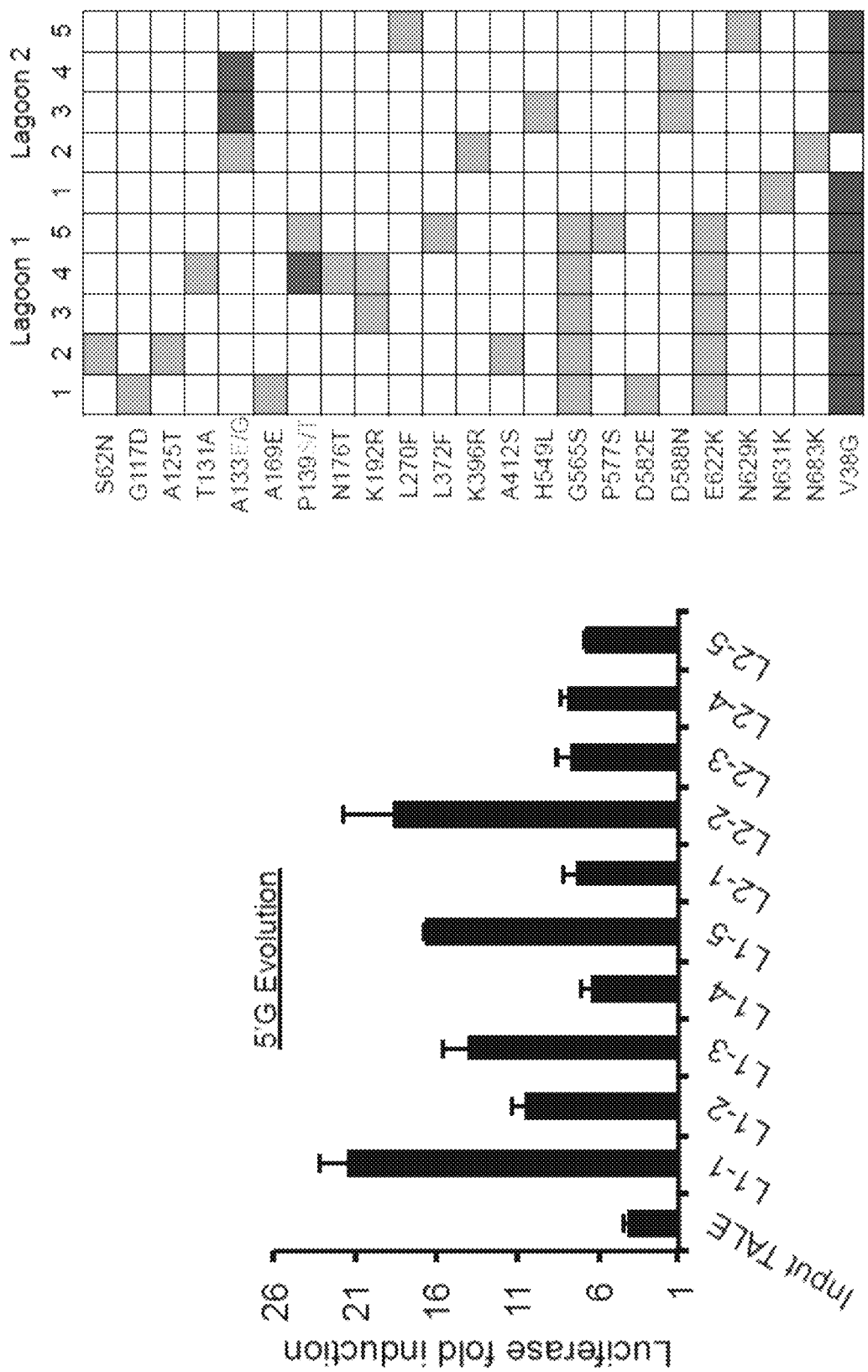
Figure 12A:
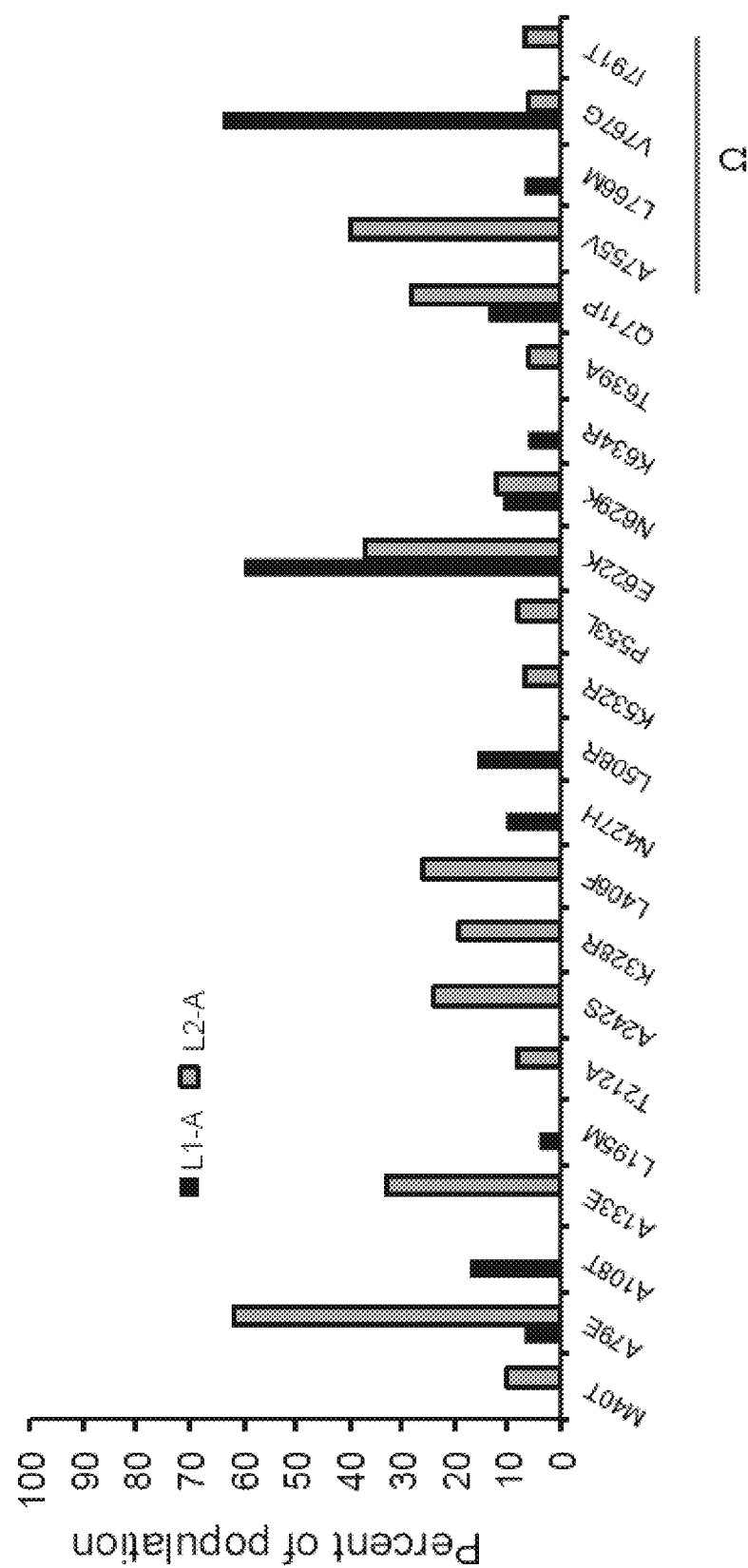
FIGS. 12A-12C show high-throughput sequence analysis of phage populations evolved to bind target sequences beginning with 5' A, C, or G. Frequency of mutations arising in lagoon 1 (L1) or lagoon 2 (L2) following 48 h of PACE in the presence of mutagenesis on CBX8-directed target sequences beginning with 5' A (FIG. 12A), 5' C (FIG. 12B), or 5' G (FIG. 12C). Only mutations observed at a frequency ≥5% are shown.
Figure 12B:
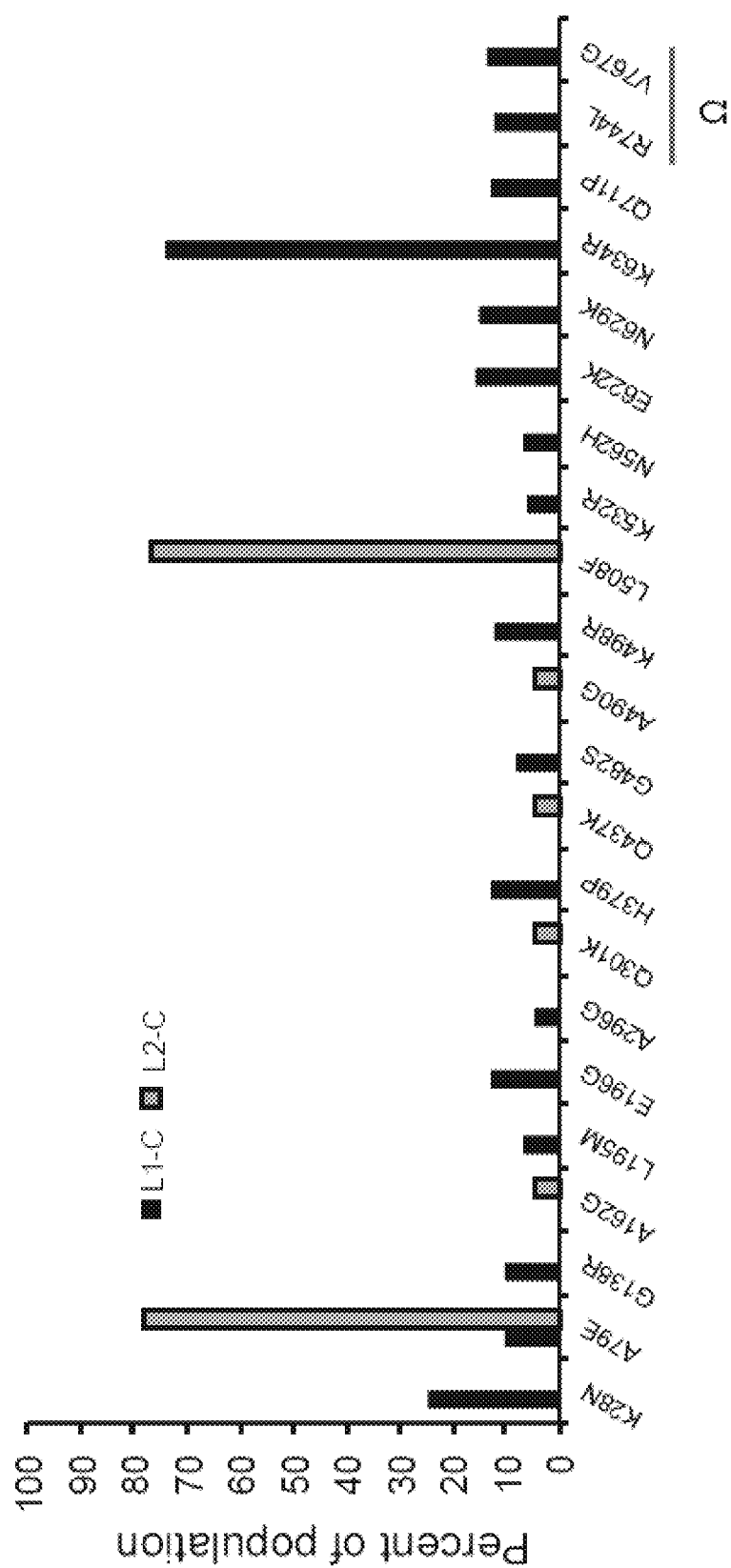
Figure 12C:
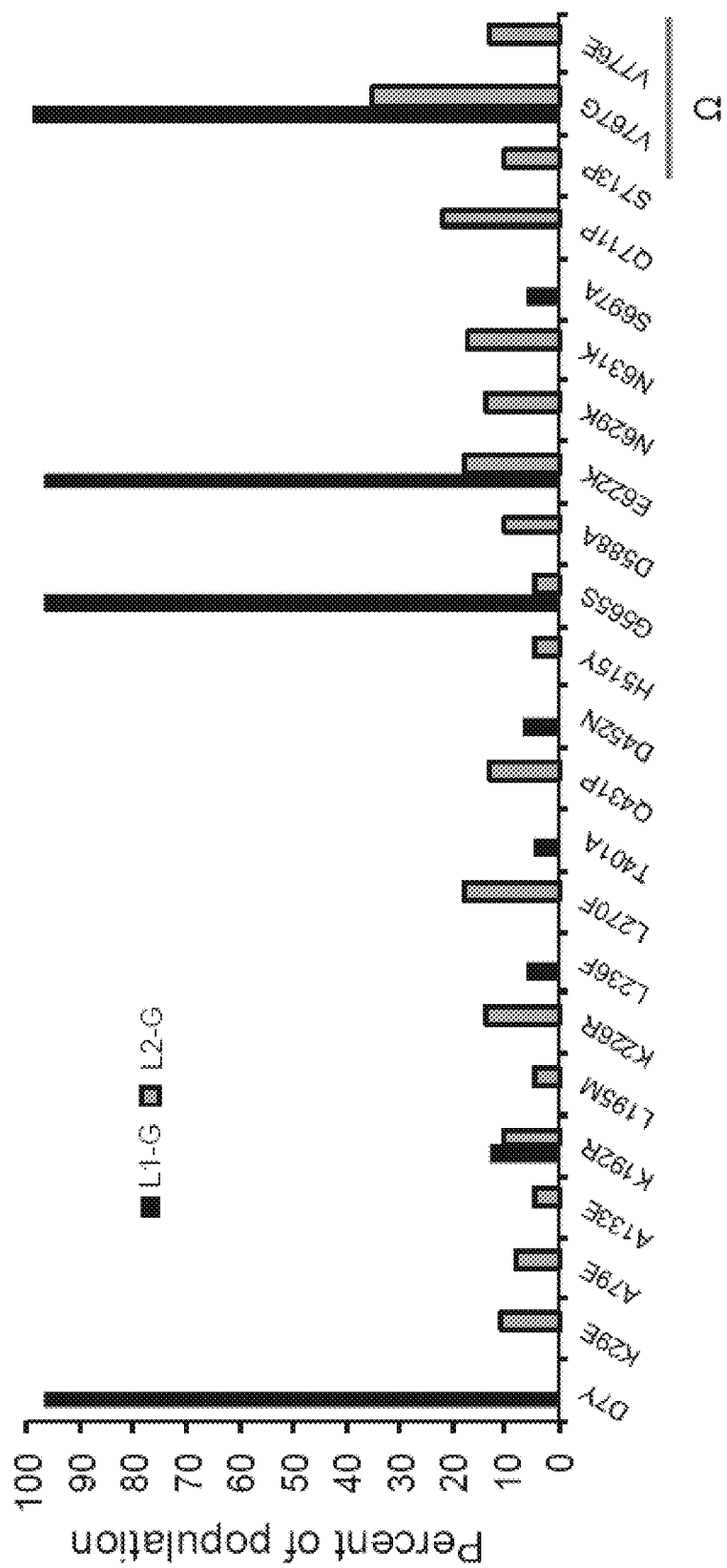
Figure 13E:
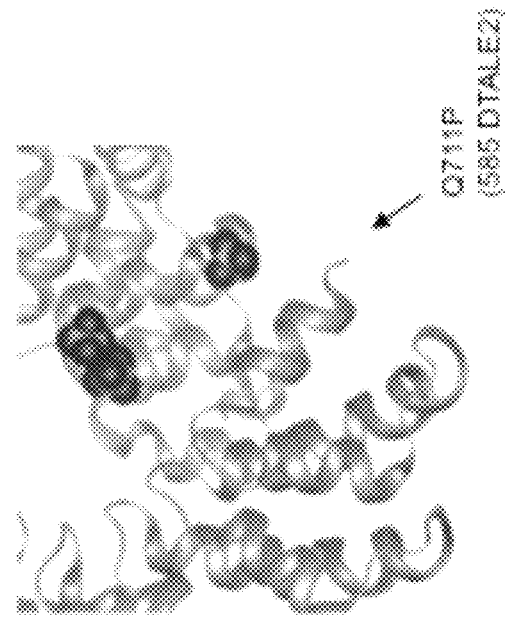

Analysis of individual clones from these three evolutions experiments revealed a variety of mutations occurring throughout the entire TALE protein sequence (FIG. 2B and FIG. 11A, 11B). High-throughput sequencing of ~$10^5$ phage revealed that TALE mutations A79E (62% L2), A133E (33% L2), E622K (60% L1, 37% L2), and Q711P (28% L2), were prevalent in 5' A lagoons (FIG. 12A), while A79E (78% L2), L508F (77% L2), and K634R (74% L1) were dominant in 5' C lagoons (FIG. 12B), and D7Y (97% L1), G565S (97% L1), and E622K (97% L1) were predominant in the 5' G lagoon (FIG. 12C). In addition, V767G, corresponding to V38G in the RNAP ω subunit, was common among phage evolved in the 5' A and 5' G lagoons (FIG. 12A, 12C). Combined with structure-activity analyses (FIG. 13), these data reveal substitutions that alter TALE 5' nucleotide specificity and binding activity, and highlight the value of unbiased mutagenesis in DB-PACE that allows the discovery of neutral and beneficial amino acid substitutions that cannot be easily predicted a priori.

Previous attempts to evolve 5' TALE specificity using traditional directed evolution methods did not achieve specific recognition of 5' A or 5' C[28,29]. To assay the specificity of the evolved phage pools, a series of plaque assays were performed using cells carrying APs with binding sequences beginning with a 5' A, C, G, or T. This assay revealed that the activity of evolved CBX8-targeting TALEs was increased in a promiscuous manner, as expected given the absence of a counter-selection, and was not specific to any 5' nucleotide (FIG. 14A). To evolve selective recognition of non-T 5' nucleotides, a negative selection strategy was adapted that links undesired activities to the production of pIII-neg, a dominant negative pIII variant that poisons, rather than enables, phage propagation[33].

Figure 2C:
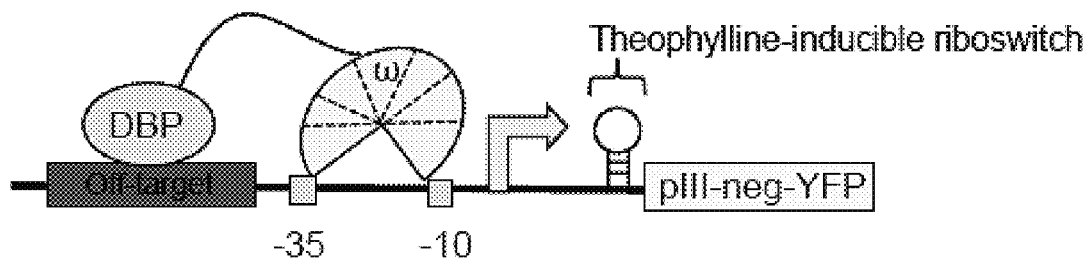

A series of negative selection APs (APNegs) were designed in which binding of a TALE-ω fusion protein to an off-target DNA sequence induces expression of gene III-neg (encoding pIII-neg) fused to yellow fluorescent protein (YFP) from a minimal lac promoter (FIG. 2C). To enable tuning of negative selection stringency, a theophylline-inducible riboswitch was placed upstream of gene III-neg-YFP. Next, cells carrying an AP requiring recognition of a 5'A-CBX8 sequence were generated, in combination with one of three APNegs bearing 5' C-, G-, or T-CBX8 sequences. Using the TALE-ω SP evolved to bind to the 5' A sequence, plaque assays were performed on each of these strains in the presence of increasing doses of theophylline to modulate pIII-neg production resulting from binding to 5' C, G, or T sequences in the corresponding APNeg. It was confirmed that phage propagation could be suppressed in an activity- and theophylline-dependent manner (FIG. 14B, 14C). Together, these results establish a negative selection system for DB-PACE.

This negative selection system was applied to evolve TALE domains that preferentially bind a 5' A target site over a 5' T using simultaneous positive and negative selection in PACE. To perform simultaneous multiplexed negative selection against binding of target DNA sequences beginning with 5' C, G, or T, three E. coli strains were mixed in equal proportion, each carrying an APNeg plasmid containing a 5' C, G, or T off-target sequence, together with a positive selection AP harboring the 5' A target site and an MP. The resulting mixed host cell population was used in a 144-h PACE experiment in which phage surviving the previous 5' A PACE experiment were subjected to increasing levels of negative selection stringency (+0.1 mM theophylline every 48 h).

Figure 2D:
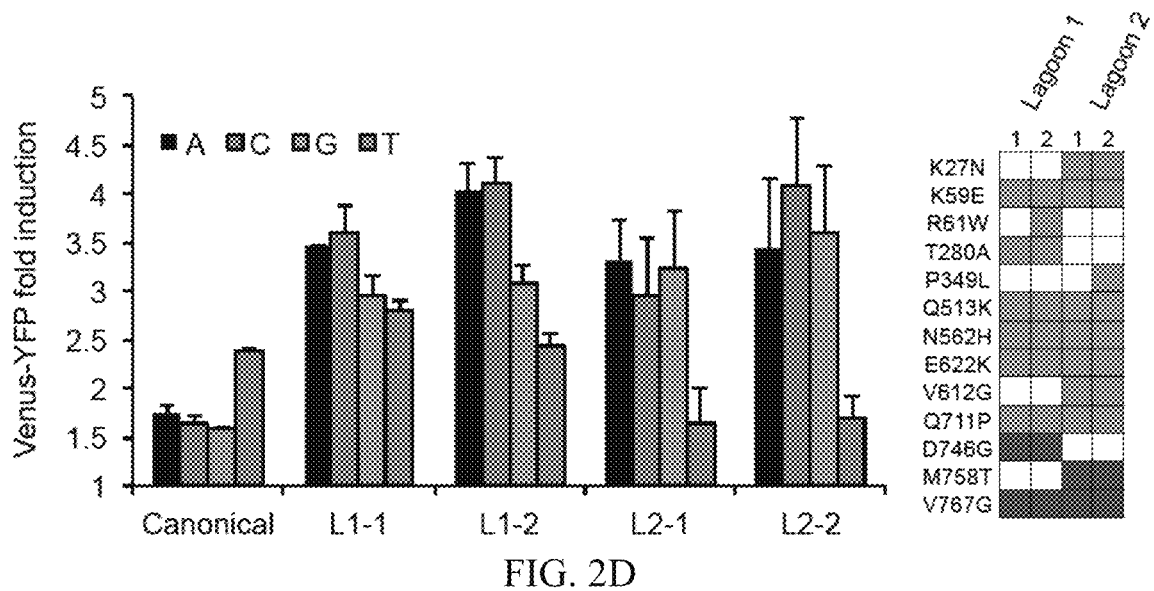

Several TALE-encoding genes surviving 144 h of dual positive and negative PACE were cloned into tetracycline-inducible expression plasmids and transformed each of them into four distinct cell strains containing APNeg plasmids with a CBX8 binding site starting with 5' A, C, G, or T, to assay their 5' specificity. Measurement of anhydrotetracycline (ATc)-induced YFP fluorescence revealed that all clones displayed substantial (>2-fold) increase in DNA-binding activity on sequences beginning with 5' A, 5' C, and 5' G, and that clones from lagoon 2 (L2) displayed a two-fold reduction in binding affinity for the canonical 5' T site, resulting in a ~4-fold 5' A vs. T specificity change relative to the canonical TALE protein (FIG. 2D). These results suggest stronger selection against binding 5' T sequences and weaker selection pressure against binding sequences starting with 5' C or 5' G. This outcome likely resulted from negative selection against the 5'T sequence engaging earlier in the 144 h experiment than negative selection on the 5' C and 5' G sequences. Consistent with this hypothesis, in vitro plaque assays showed that a low dose of theophylline (0.2 mM) is sufficient to suppress evolved 5'-A phage propagation on cells carrying a 5' T-CBX8 sequence, while a higher dose (0.4 mM) is required to block propagation on 5' C or 5' G sequences (FIG. 14C). Based on the theophylline titration schedule, phage experienced ~48 h of negative selection against the 5' T sequence, but only 24 h against the 5' C and 5' G sequences. While differences in the genotypes and phenotypes observed in L1 and L2 reflects the stochastic nature of protein evolution, 100% of the evolved TALEs assayed following negative selection exhibited preferences for 5' A over 5' T (FIG. 2D).

Figure 15A:
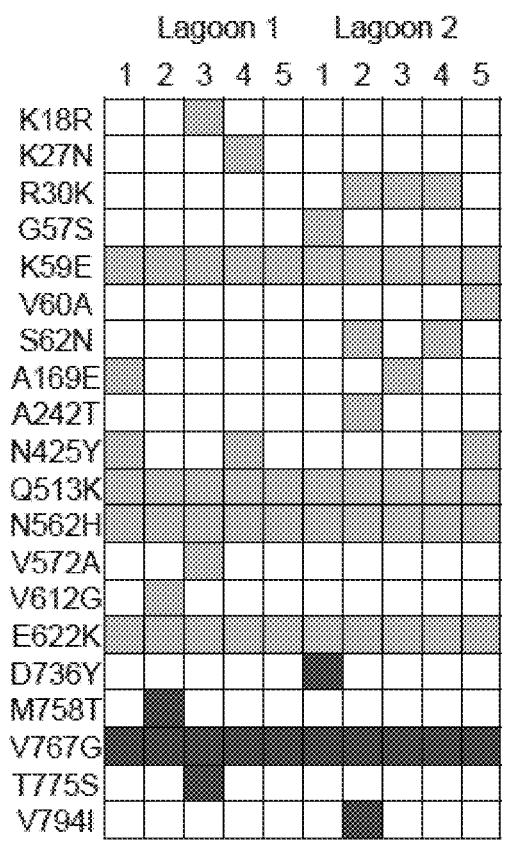
FIGS. 15A-15B show clonal and population genotypes following negative selection of 5' A-evolved phage against 5' C, G, and T binding.
Figure 15B:
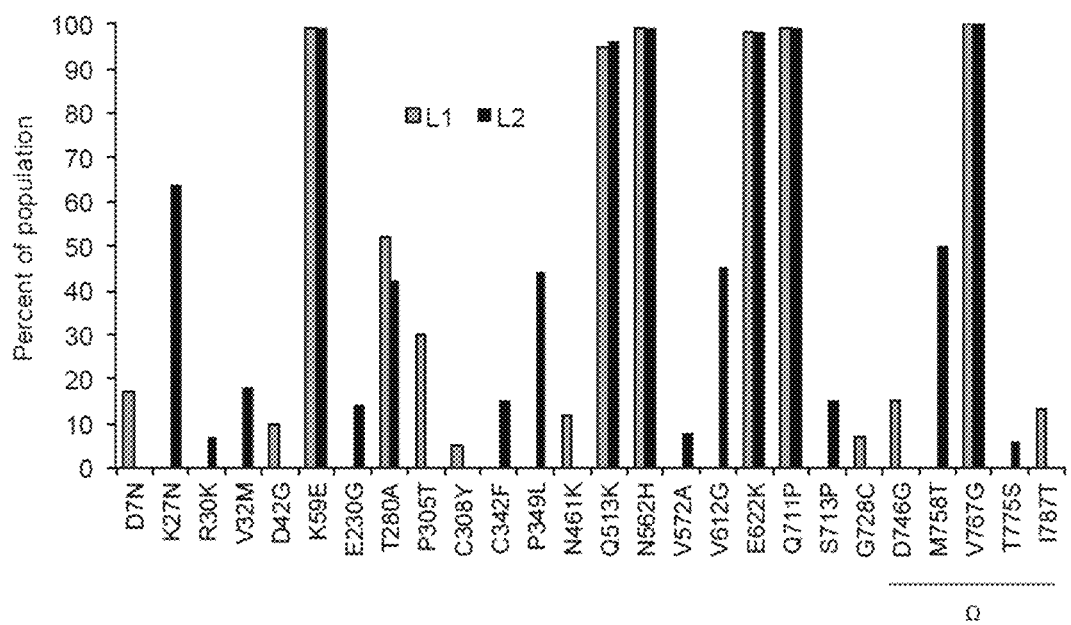
Figure 16A:
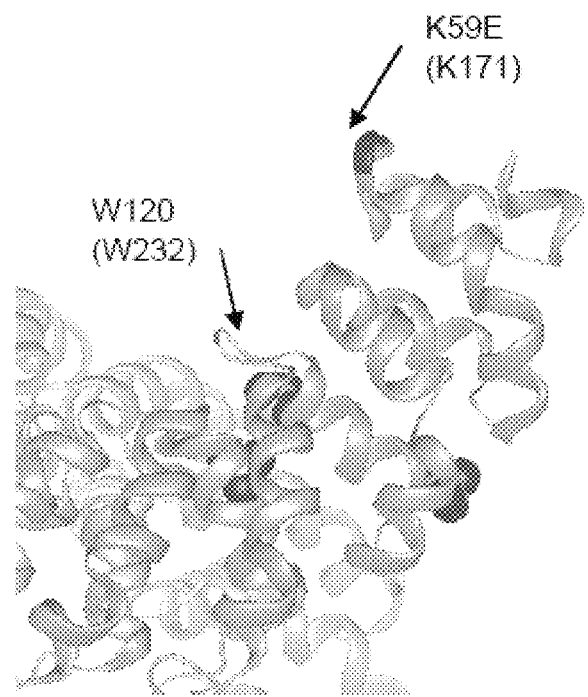
FIGS. 16A-16D show a characterization of mutations arising from negative selection PACE against target sequences beginning with 5' C, G, or T.
Figure 16B:
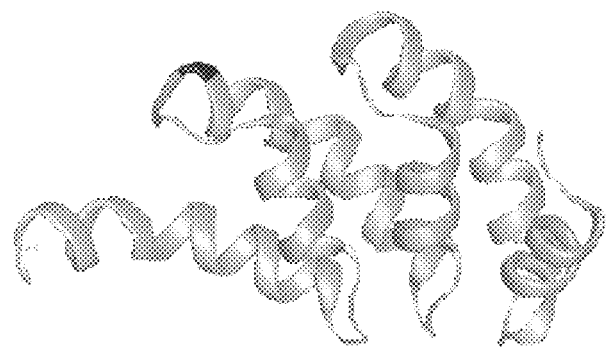
Figure 16C:
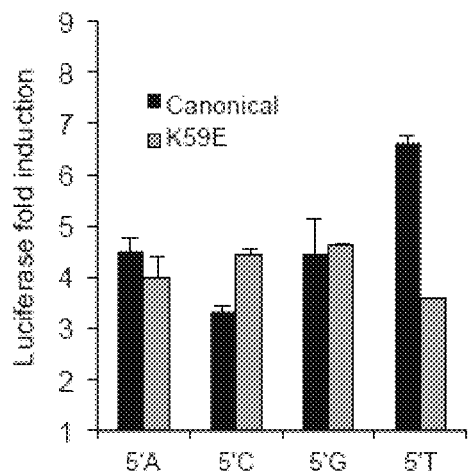
Figure 16D:
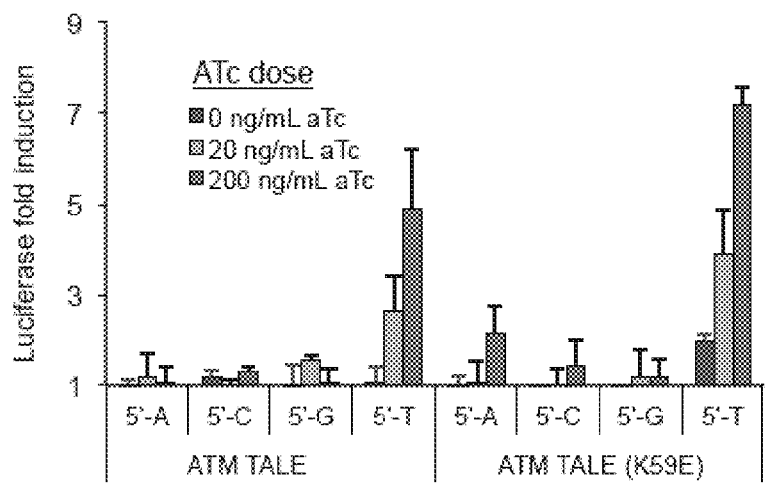

Sequencing ten individual clones from the end of the experiment revealed an average of nine amino acid substitutions distributed throughout each protein (FIGS. 2D and 15A), and high-throughput sequence analysis of phage pool genotypes revealed six predominant amino acid substitutions (K59E, Q513K, N562H, E622K, Q711P, V767G) in the 144 h population (FIG. 15B). Of these, only K59E and Q513K (FIG. 16A, 16B) emerged exclusively following negative selection, and only the N-terminal substitution K59E was amenable to study using site-directed mutagenesis due to the highly repetitive nature of TALE repeat arrays. It was found that when present in isolation on the CBX8 TALE K59E decreases affinity for the 5' T target sequence by 2-fold, but has little effect on sequences beginning with 5' A, C, or G (FIG. 16C). To test if the effect of the K59E mutation is CBX8-TALE context-dependent, or if the mutation alters TALE specificity in a general manner, this mutation was introduced to a different TALE protein targeting the ATM locus (see Table 2 for target sequences) and assayed the activity of the resulting mutant on the corresponding 5' A, C, G, or T target sequences. The K59E substitution in the ATM TALE increased activity on both 5' A and 5' T sequences by a factor of 2 and 1.5-fold, respectively, indicating that while this position impacts 5' specificity in both TALE proteins, the manner in which the K59E mutation affects DNA binding is context-dependent (FIG. 16D). These results collectively show that coupled positive and negative selection DB-PACE can rapidly alter TALE 5' DNA specificity in a context-dependent manner by maintaining TALE activity on a site containing a target 5' nucleotide while evolving mutations that decrease binding to other 5' off-target sequences.

TABLE 2

Full target sequences used to study ATM TALENs[a].

| Sequence | Left-half sequence | SEQ ID NO: | Right-half sequence[b] | SEQ ID NO: |
|---|---|---|---|---|
| On-target | TGAATTGGGATGCTGTTT | 15 | TTTATTTTACTGTCTTTA | 16 |
| OffA1 | TGAATaGGaAataTaTTT | 17 | TTTATTTTACTGTtTTTA | 18 |
| OffA11 | TGAATTGaGAgaagcaTT | 19 | TTTATTTTAtTaTtTTTA | 20 |
| OffA17 | gGAAaTGGGATaCTGagT | 21 | TTTATgTTACTaTtTcTA | 22 |
| OffA23 | TagATTGaaATGCTGTTT | 23 | TTTtTaTTAtTaTtTTTA | 24 |

[a]For in vitro cleavage assays, left and right half-site recognition sequences were separated by a constant 18-bp constant spacer sequence (5'-TTAGGTATTCTATTCAAA-'3) (SEQ ID NO: 25). For high-throughput specificity profiling, a range of spacer lengths was used in the library[30].
[b]For the right half-site the sense strand is displayed.

Example 3: Continuous Evolution of Improved TALEN Specificity

TALE arrays are frequently used in the context of TALENs to initiate genome editing[7]. The DNA cleavage specificity of TALENs is imperfect, and off-target DNA sites can undergo TALEN-mediated modification at appreciable levels both in vitro and in human cells[30,42,43] that compromise their usefulness as research tools and potential human therapeutics. It was determined whether DB-PACE could be used to evolve TALEs with improved specificity for a given target sequence by decreasing recognition of specific off-target genomic sequences while maintaining recognition of the on-target sequence. Off-target genomic sequences can be identified using in vitro high-throughput specificity profiling[30,44,45] or other approaches[20,42,46,47].

Figure 3A:
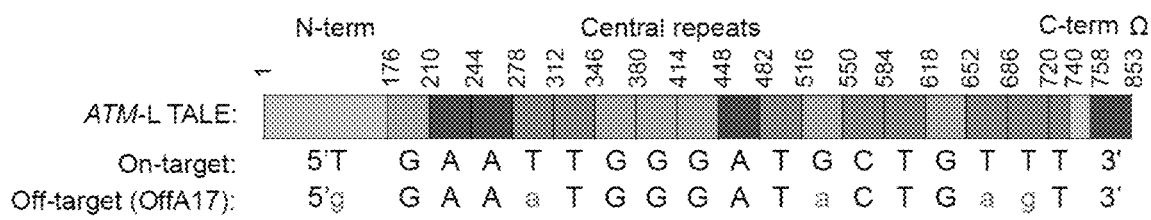
FIGS. 3A-3B show the continuous evolution of TALEs with improved specificity.

To validate the ability of DB-PACE to improve TALEN specificity, a TALEN pair that targets a 36-bp sequence within the human ATM locus was used (see Table 2 for target sequences) for which off-target cleavage sites in human cells[30] were previously identified. An SP encoding the TALE specifying recognition of the 18-bp left half-site (ATM-L) fused to the ω RNAP subunit was generated, and an AP containing the ATM on-target binding sequence. Next, an APNeg with an 18-bp operator sequence corresponding to the left half site of OffA17 was generated, which is the most frequently cleaved known off-target sequence of this TALEN in the human genome[30]. OffA17 differs from the on-target ATM site at five nucleotide positions (FIG. 3A). Both the positive selection AP and the negative selection APNeg were co-transformed into host cells to enable simultaneous positive and negative selection during PACE.

Using these cells, DB-PACE was performed on the ATM-L TALE in duplicate lagoons (L1 and L2) at a flow rate of 1.3 vol/h. Increasing quantities of theophylline were added to each lagoon from a starting dose of 0 mM to a final dose of 0.4 mM (+0.1 mM every 24 h) to successively increase negative selection stringency. At 120 h, the evolved phage populations from L1 and L2 were pooled, and subjected the mixture to a subsequent 24 h PACE experiment in a single lagoon (L3) using a fixed concentration of 0.4 mM theophylline and a higher lagoon flow rate of 2.0 vol/h.

Figure 3B:
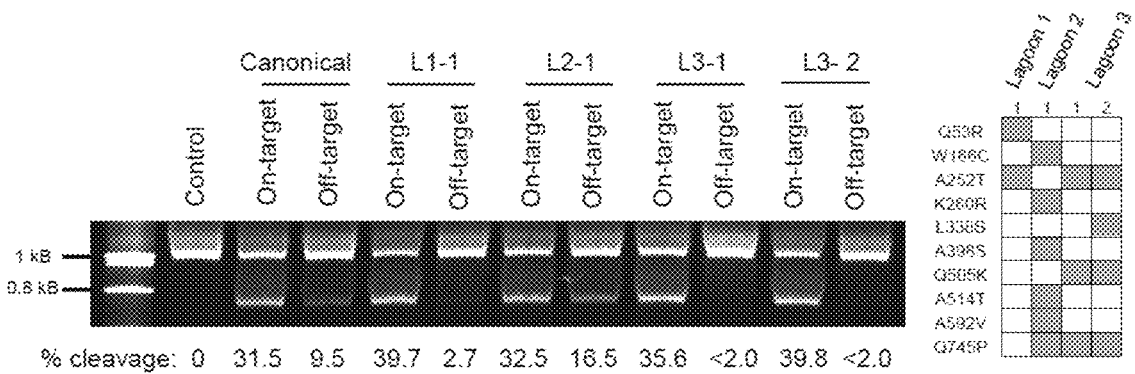
Figure 17A:
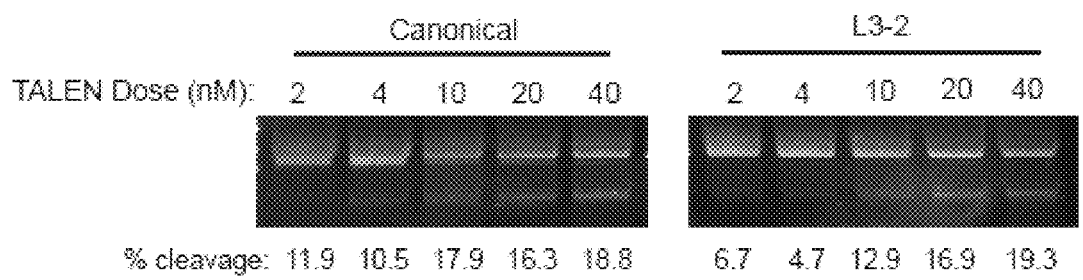
FIGS. 17A-17B present a comparison of on=target cleavage efficiency of canonical and evolved L3-2 TALENs.
Figure 17B:
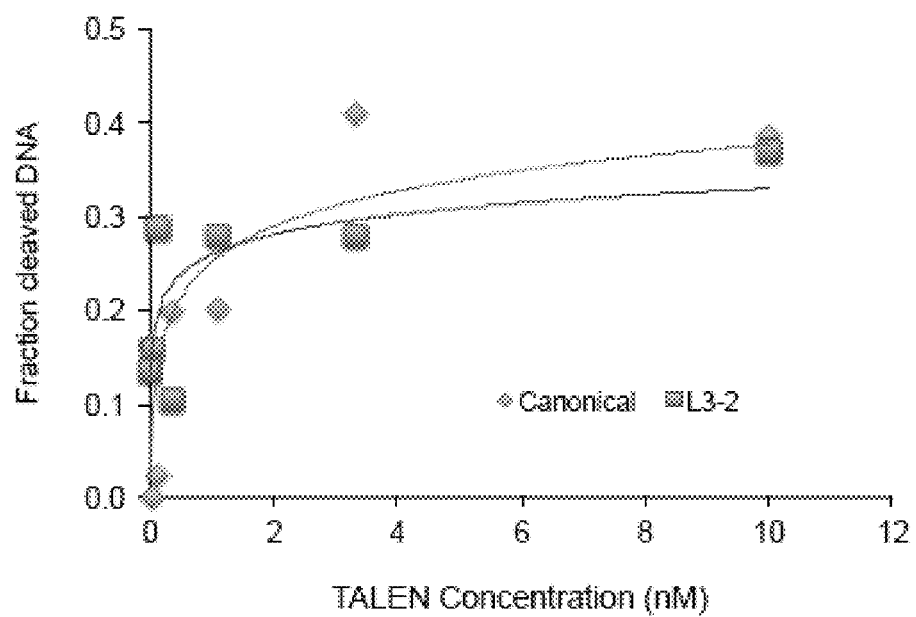
Figures 18A, 18B, 18C:
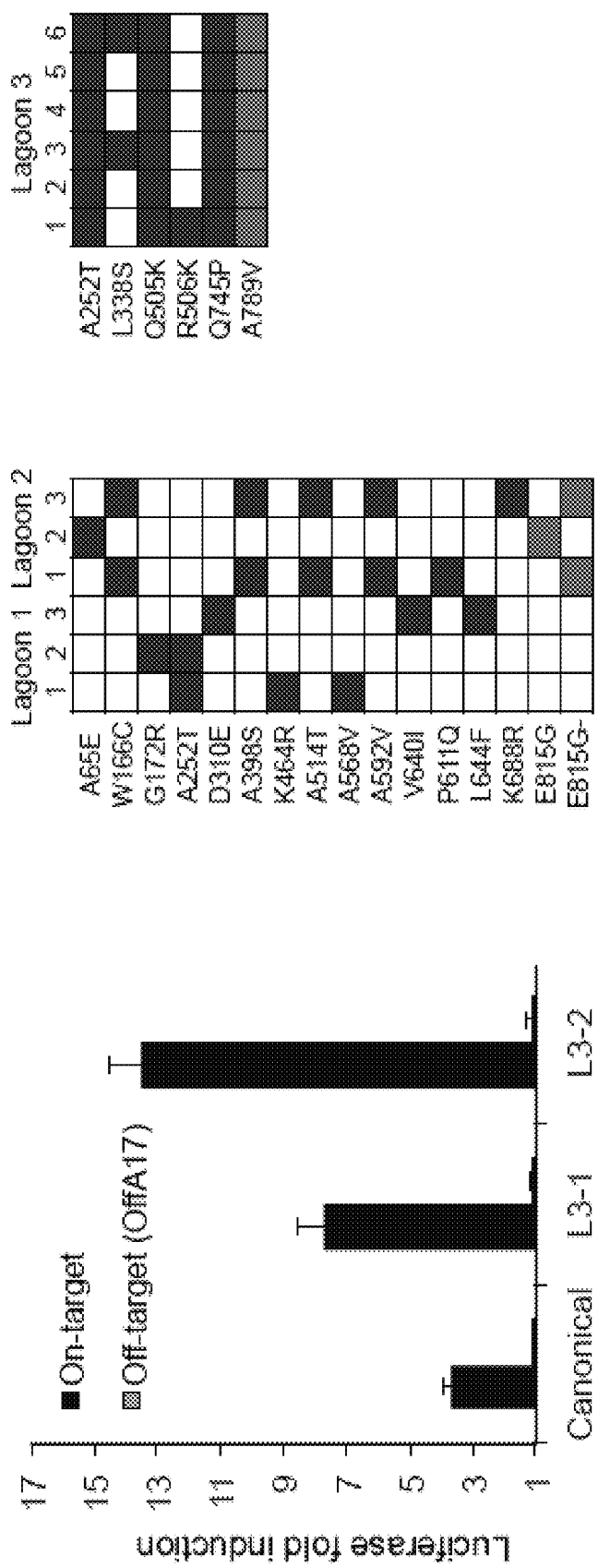
FIGS. 18A-18D show characterizations of evolved ATM-L TALEs following positive and negative selection PACE.

Several evolved TALE proteins emerging from L1, L2, and L3 were assayed in the context of the ATM TALEN pair using the in vitro DNA cleavage specificity profiling assay[30]. The canonical TALEN pair before evolution exhibited robust cleavage in vitro of the on-target sequence (31.5% cleavage at a concentration of 12 nM after 90 min) and substantial cleavage of the off-target sequence OffA17 (9.5% cleavage under the same conditions) (FIG. 3B). In contrast, TALEN pairs containing the evolved ATM-L TALEs from L1 or L3 retained on-target DNA cleavage activity comparable to that of the canonical TALEN, but exhibited virtually no detectable cleavage of OffA17 under these conditions (FIG. 3B). The L3 evolved clones showed at least 16-fold higher (bounded by the limit of detection) on-target:OffA17 off-target cleavage specificity in vitro than the canonical TALEN (FIG. 3B). Importantly, the on-target activities of the canonical and L3-2 TALEN pairs were comparable, indicating that on-target activity was not reduced by DB-PACE (FIG. 17). Indeed, luciferase assay of evolved ATM-L-TALEs in the context of ω subunit fusions revealed that they exhibited 2- to 3-fold higher activity on the on-target site than the canonical ATM-TALE, but no detectable activity on the OffA17 site (FIG. 18A). Taken together, these findings demonstrate the successful continuous evolution of TALE proteins with greatly improved on-target:off-target DNA specificities together with preserved or enhanced on-target DNA-binding activity.

Figure 18D:
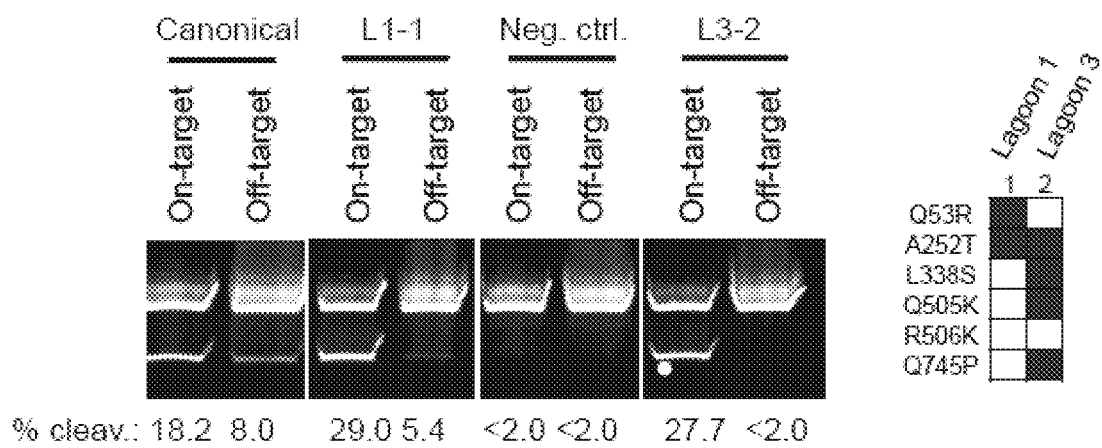
Figure 19A:
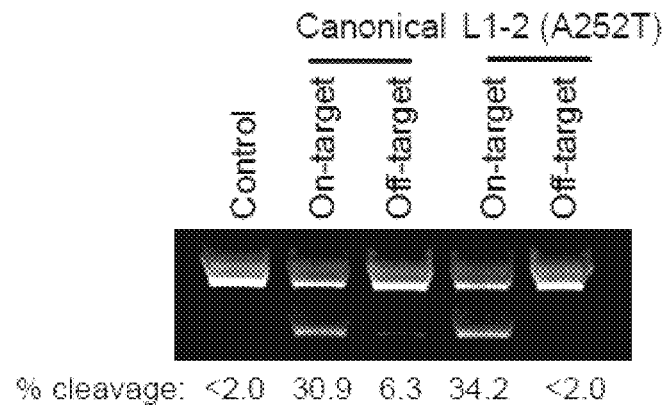
Figure 19B:
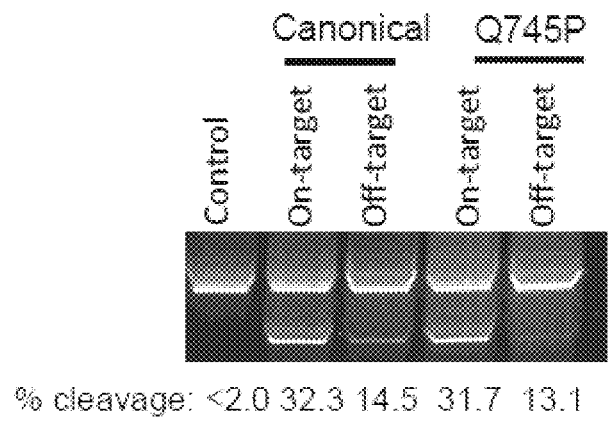

Sequencing of several evolved ATM-L TALEs revealed a variety of mutations in L1 and L2 (FIGS. 3B and 18B), but a fairly converged L3 population characterized by A252T, L338S, Q505K, and Q745P (FIGS. 3B and 18C). Analysis of a series of evolved clones revealed that while Q53R in combination with A252T improved specificity substantially, A252T in combination with Q505K, L338S, and Q745P improved specificity by an additional >2-fold (FIG. 18D). Although the highly repetitive nature of TALE array genes precludes site-directed mutagenesis studies on residues within repeats, we identified an ATM-L TALE variant containing only a single A252T mutation. This mutation in isolation exhibited on-target cleavage activity comparable to that of the canonical TALE, but drastically reduced cleavage of OffA17 (~0.3% compared to 6.3% for the canonical TALE) (FIG. 19A). The effect of the C-terminal Q745P substitution, corresponding to Q711P in the CBX8-TALE, was assayed in isolation by site-directed mutagenesis and determined that this mutation did not effect on-target or off-target cleavage activity in vitro (FIG. 19B). The dynamic range of the gel-based in vitro TALEN cleavage assay was insufficient to distinguish between the specificity enhancement of two clones containing identical genotypes differing only by the presence (L3-2) or absence (L3-1) of L338S (FIG. 3B). Collectively, these results identify A252T as a key mutation and L338S as a potential accessory mutation that alter the on-target:off-target cleavage propensity of the ATM-targeting TALE (FIGS. 3 and 19A-19D).

Figure 20A:
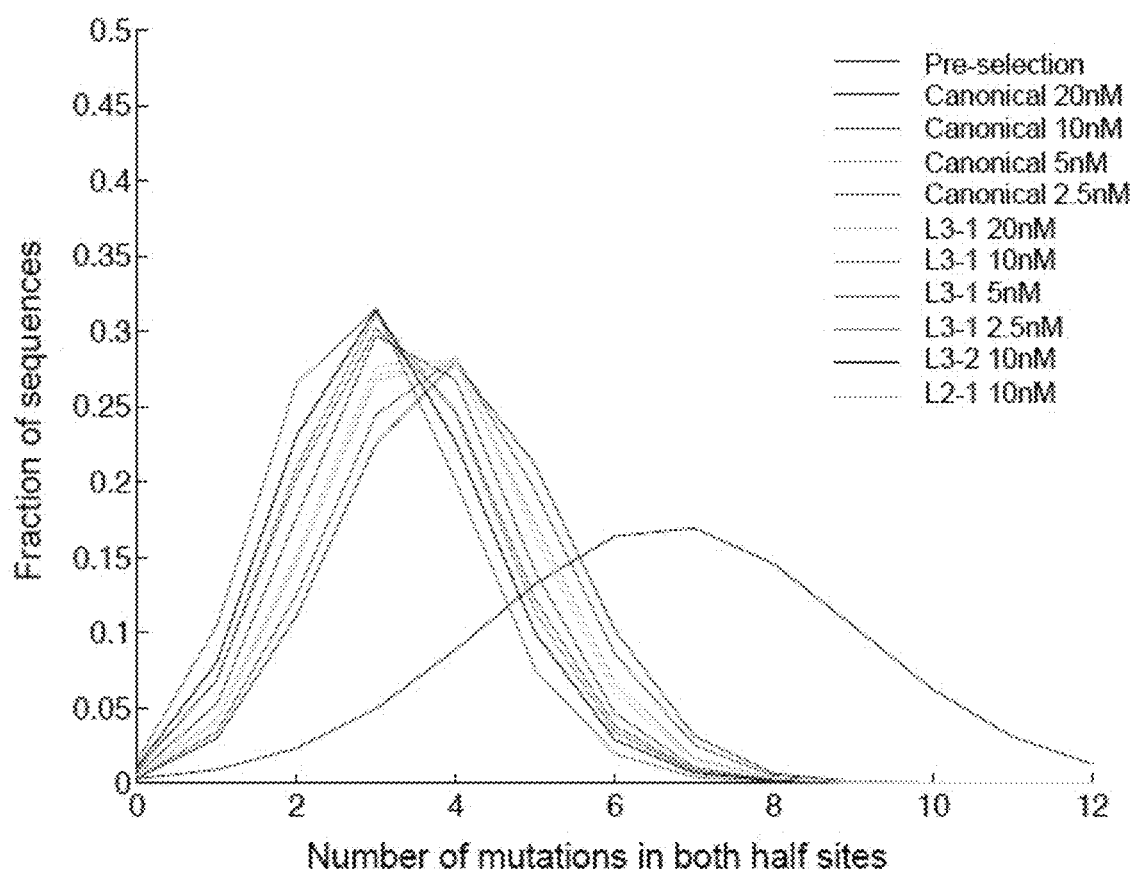
FIGS. 20A-20B show a global analysis of in vitro TALEN specificity.
Figure 20B:
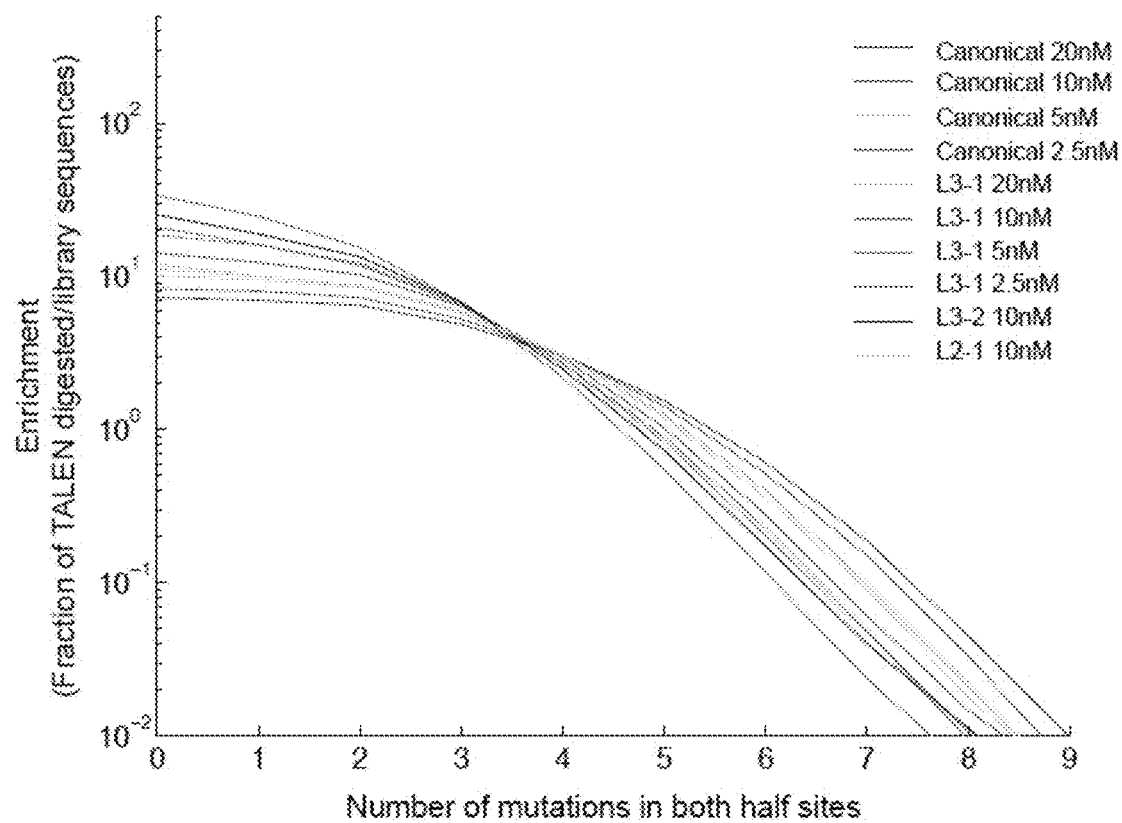

To investigate whether the evolved specificity enhancements are limited to the OffA17 off-target sequence, or if instead they also improve DNA cleavage specificity against other sequences, the ability of the evolved TALENs to cleave variants of OffA17 was assayed containing subsets of its five mutations. Cleavage of these sequences was similar between the canonical and evolved L3-1 TALEN pairs (FIG. 19E). To reveal the broad DNA cleavage specificity of the evolved TALENs, our previously described TALEN specificity profiling method[30] was used to measure the ability of a TALEN to cleave any of >10$^{12}$ DNA sequences that are related to the on-target site. A DNA library was digested that was sufficiently diverse to contain at least ten copies of all DNA sequences with six or fewer mutations from the on-target ATM sequence with either the canonical TALEN pair, or with TALEN pairs containing an evolved ATM-L TALE (L2-1, L3-1, or L3-2) in combination with the canonical ATM-R TALE (see Table 3 for statistics). The specificity profile was generated as previously described[30]. Next, we calculated the enrichment factor for each library member that survived selection by dividing its abundance after selection by its abundance before selection. Mean enrichment values for the on-target sequence ranged from ~8 to 20 across the various samples (FIG. 20A, 20B). Importantly, TALEN pairs containing the evolved TALEs L3-1 and L3-2 showed a substantially decreased ability to cleave off-target sequences containing four to nine mutations relative to the canonical TALEN (FIG. 20B). For example, L3-1 cleaved off-target sequences containing seven mutations ~7-fold less efficiently than the canonical TALEN (both at 2.5 nM), despite cleaving on-target sequences 2-fold more efficiently (FIG. 20B). These results indicate that the evolved TALEs exhibit general improvements in specificity that are not limited to the OffA17 off-target site used during negative selection PACE, but instead increase the ability of the evolved TALEs to reject other related off-target sequences as well (FIG. 20).

TABLE 3

Statistics of sequences selected by TALEN digestion.

| Selection | Seq. count | Mean mut. | Stdev mut. | P-value vs. library[a] |
|---|---|---|---|---|
| Canonical 20 nM | 181361 | 3.991 | 1.421 | $4.78 \times 10^{-11}$ |
| Canonical 10 nM | 180277 | 3.853 | 1.396 | $3.83 \times 10^{-11}$ |
| Canonical 5 nM | 206958 | 3.662 | 1.367 | $2.40 \times 10^{-11}$ |
| Canonical 2.5 nM | 343423 | 3.282 | 1.321 | $8.42 \times 10^{-12}$ |
| L3-1 20 nM | 137886 | 3.617 | 1.343 | $3.69 \times 10^{-11}$ |
| L3-1 10 nM | 141679 | 3.445 | 1.318 | $2.73 \times 10^{-11}$ |
| L3-1 5 nM | 190497 | 3.247 | 1.297 | $1.42 \times 10^{-11}$ |
| L3-1 2.5 nM | 342976 | 2.914 | 1.264 | $5.20 \times 10^{-12}$ |
| L3-2 10 nM | 187254 | 3.126 | 1.299 | $1.22 \times 10^{-11}$ |
| L2-1 10 nM | 181692 | 3.67 | 1.35 | $2.83 \times 10^{-11}$ |
| Pre-selection library | 453246 | 6.811 | 2.311 | NA |

Statistics are shown for the pre-selection library and for DNA surviving each TALEN selection on the ATM target sequence.
Seq. counts: total counts of high-throughput sequenced and computationally filtered selection sequences.
Mean mut.: mean mutations in selected sequences.
Stdev. mut.: standard deviation of mutations in selected sequences.
Stdev. mut.: standard deviation of mutations in selected sequences.
[a]Comparisons between the TALEN selection sequence distributions and the corresponding pre-selection library sequence distribution were determined as previously reported[44] using a one-sided t-test.

Figure 4A:
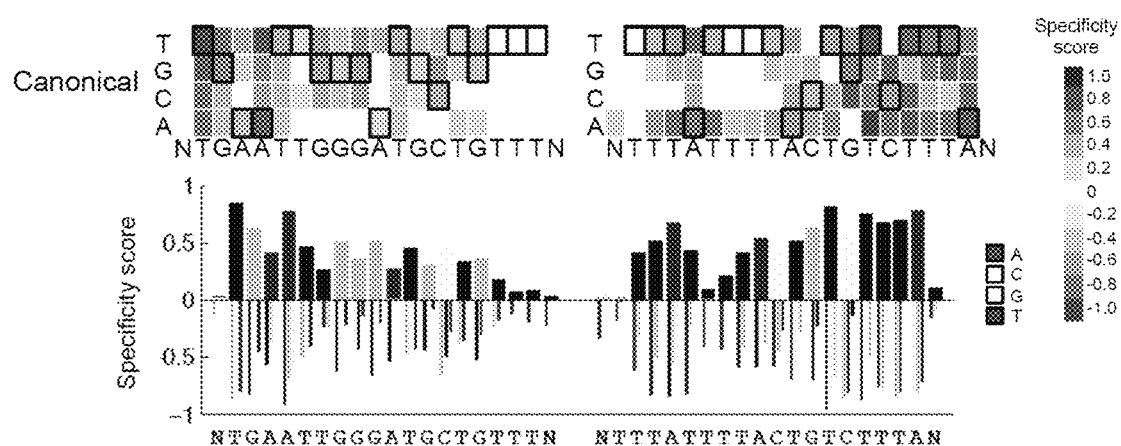
Figure 4B:
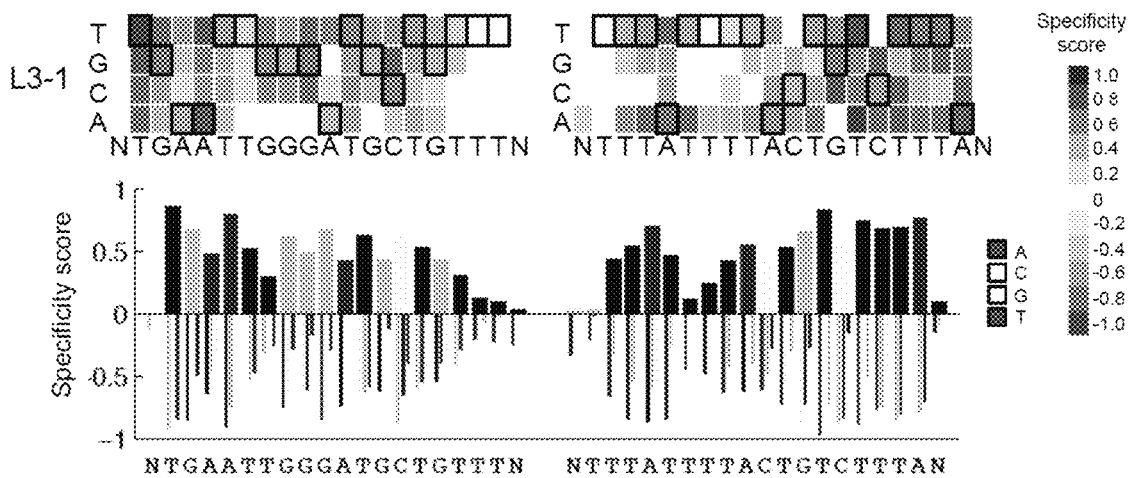
Figures 22A, 22B, 22C, 22D:
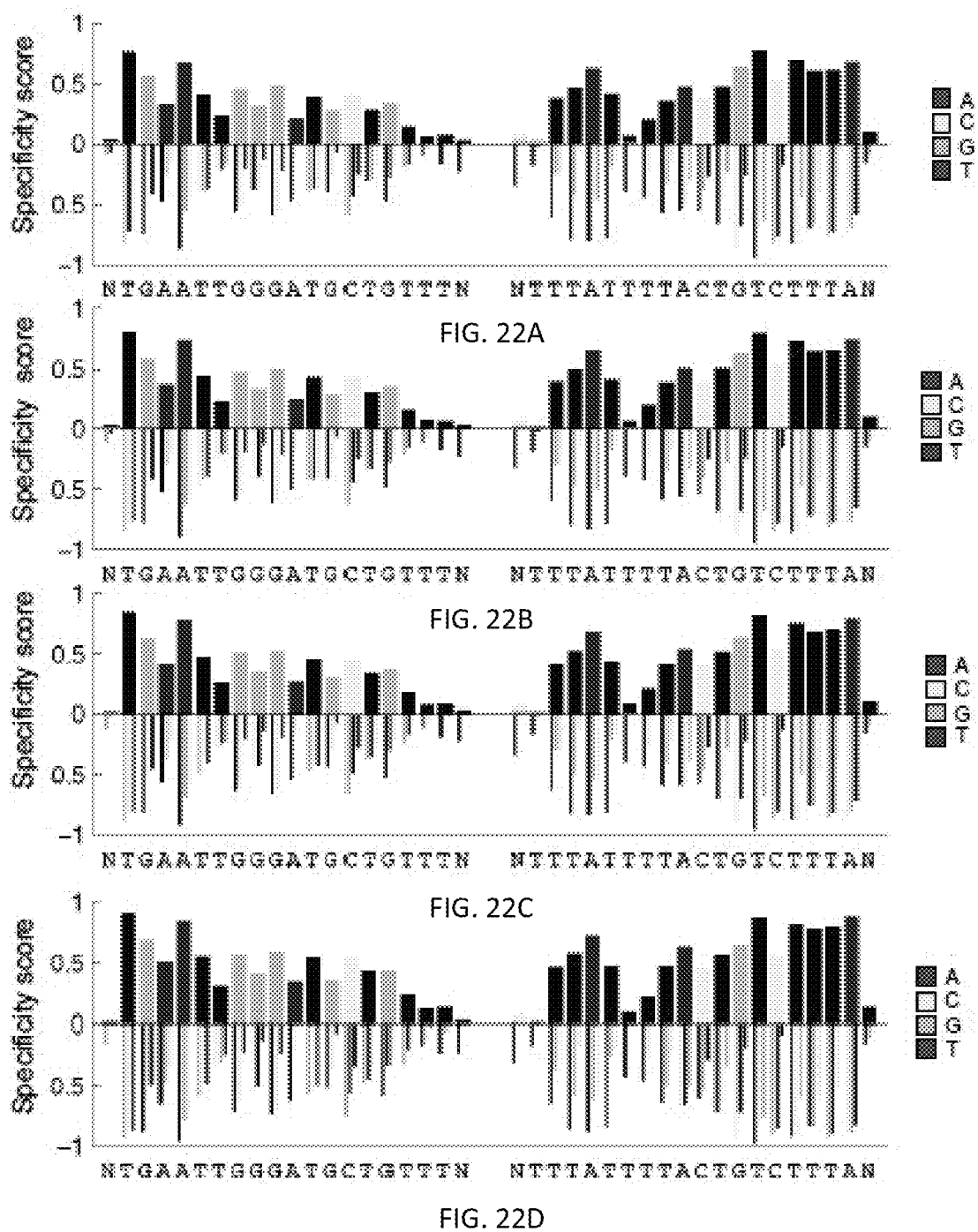
FIGS. 22A-22D are specificity profile bar graphs of the canonical ATM TALEN pair as a function of concentration. Bar graphs showing the quantitative specificity score for each nucleotide position for the canonical TALEN targeting the ATM locus used in the cleavage assay at doses of 20 nM (FIG. 22A), 10 nM (FIG. 22B), 5 nM (FIG. 22C), and 2.5 nM (FIG. 22D). Each position in the left and right half-sites plus a single flanking position (N) are shown. A score of zero indicates no specificity, while a score of 1.0 corresponds to perfect specificity. Negative specificity scores range from zero to −1.0, and represent enrichment against that base pair. Specified positions (specificity score >0) were plotted as stacked bars above the axis (multiple specified base pairs at the same position were plotted over each other with the shortest bar in front) while anti-specified base pairs were plotted as narrow, grouped bars below the axis. For the right half-site, data for the sense strand are displayed. The sequences, from left to right, correspond to SEQ ID NOs: 50 and 51.
Figure 24A:
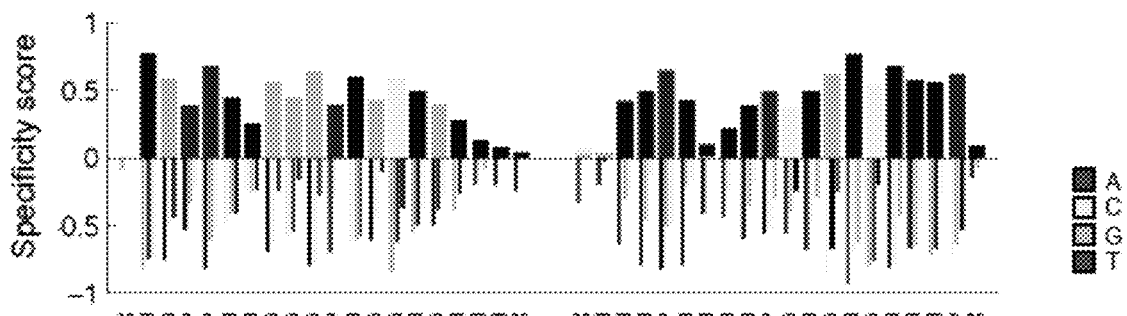
FIGS. 24A-24F are the specificity profile bar graphs of L2-1, L3-1, and L3-2 ATM TALEN pairs. Bar graphs showing the quantitative specificity score for each nucleotide position for the L3-1 TALEN pair at doses of 20 nM (FIG. 24A), 10 nM (FIG. 24B), 5 nM (FIG. 24C), and 2.5 nM (FIG. 24D), or TALEN pairs incorporating L3-2 and L2-1 TALEs at a dose of 10 Nm (FIGS. 24E and 24F, respectively). Each position in the left and right half-sites plus a single flanking position (N) are shown. A score of zero indicates no specificity, while a score of 1.0 corresponds to perfect specificity. Negative specificity scores range from zero to −1.0, and represent enrichment against that base pair. Specified positions (specificity score >0) were plotted as stacked bars above the axis (multiple specified base pairs at the same position were plotted over each other with the shortest bar in front) while antispecified base pairs were plotted as narrow, grouped bars below the axis. For the right half-site, data for the sense strand are displayed. The sequences, from left to right, correspond to SEQ ID NOs: 50 and 51.
Figure 24B:
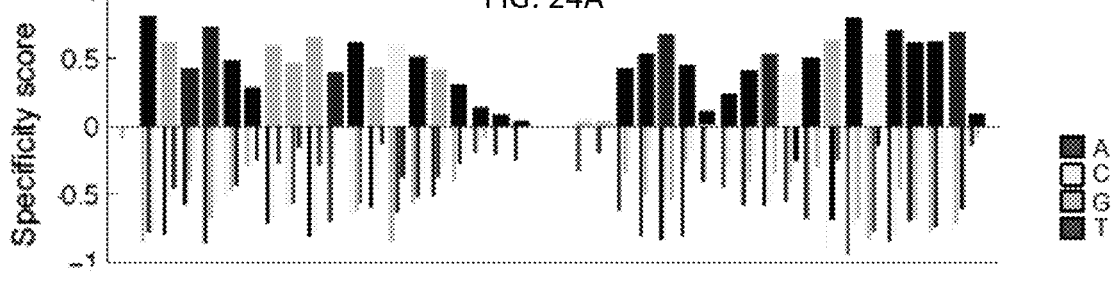
Figure 24C:
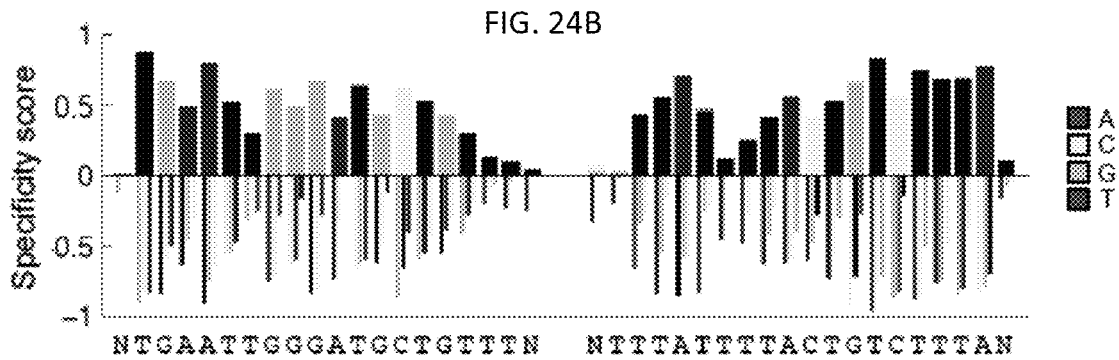
Figures 24D, 24E, 24F:
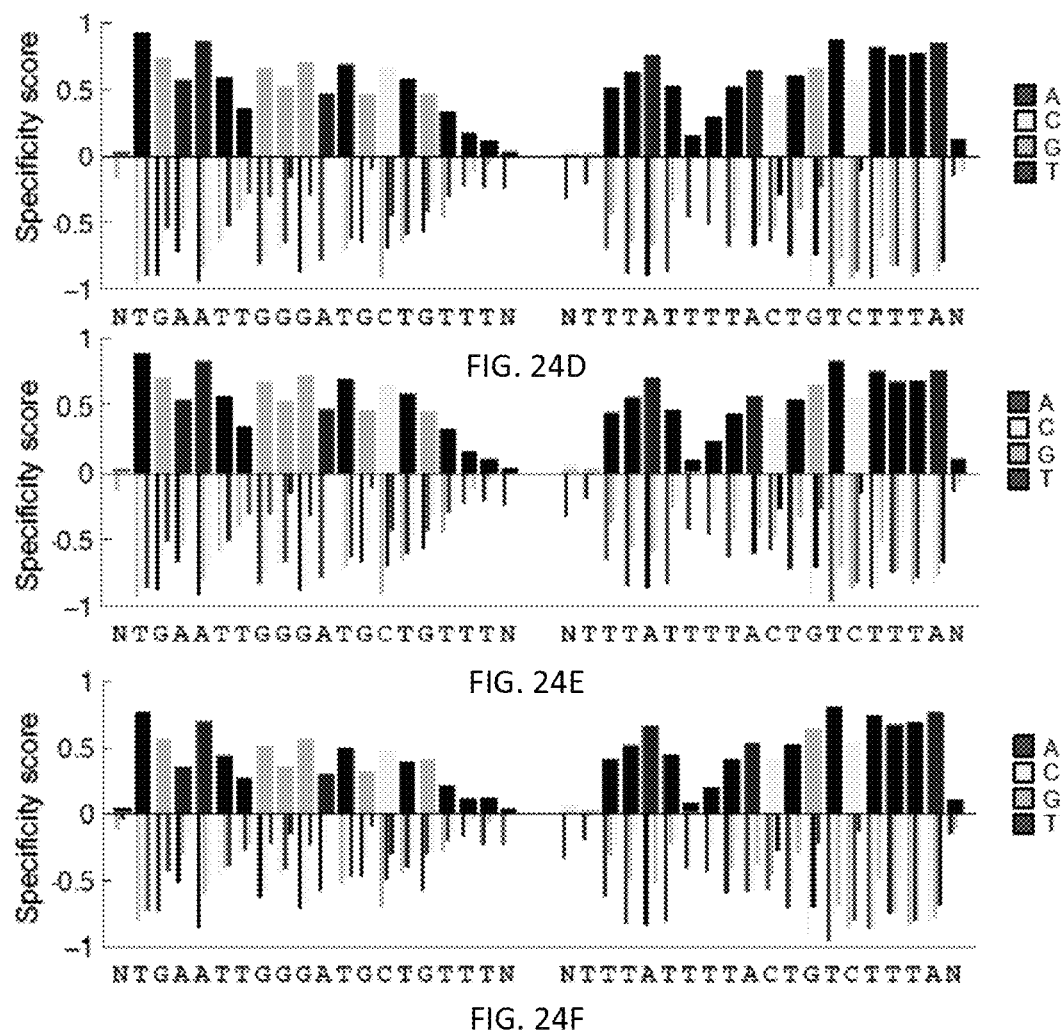
Figure 25A:
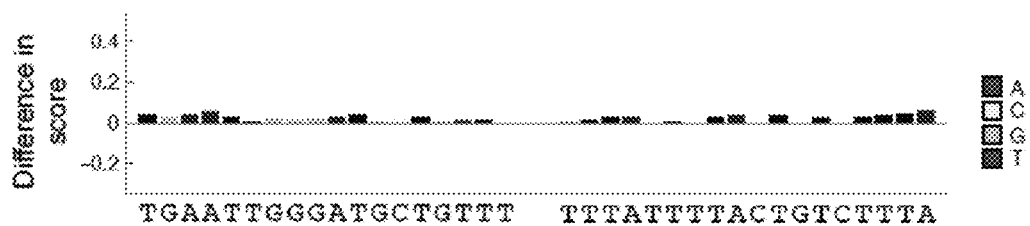
FIGS. 25A-25F show specificity profile difference as a function of TALEN concentration for canonical and L3-1 ATM TALEN pairs. Bar graph indicating the quantitative difference in specificity score at each position between cleavage using the canonical TALEN pair at a dose of 20 nM and 10 nM (FIG. 25A), 5 nM (FIG. 25B), and 2.5 nM (calculated as $score_{lowdose}-score_{20nM}$) (FIG. 25C), or TALEN pairs incorporating an evolved L3-1ATM TALE at a dose of 20 nM and 10 nM (FIG. 25D), 5 nM (FIG. 25E), and 2.5 nM (FIG. 25F). A score of zero indicates no change in specificity. For the right half-site, data for the sense strand are displayed. The sequences, from left to right, correspond to SEQ ID NOs: 15 and 16.
Figure 25B:
Figure 25C:
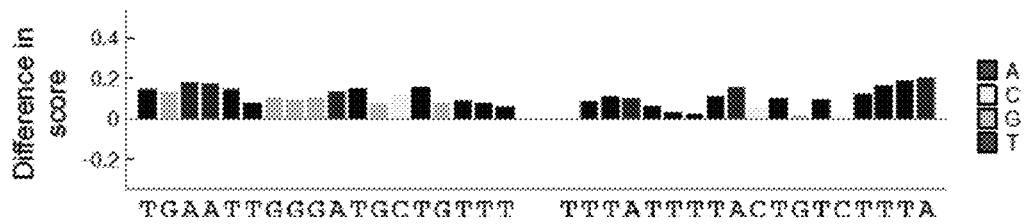
Figure 25D:
Figure 25E:
Figure 25F:
Figure 26A:
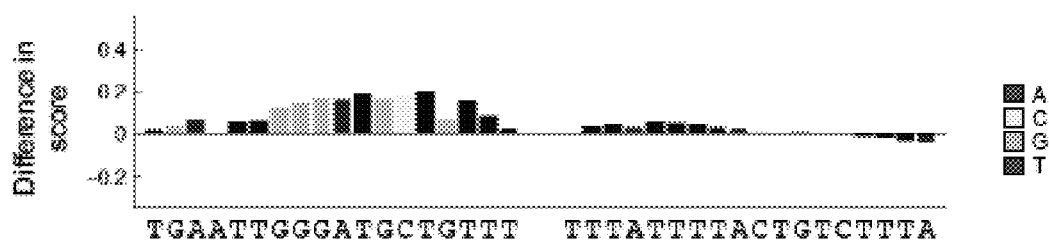
FIGS. 26A-26C are bar graphs showing the difference in specificity of the canonical TALEN pair versus the L2-1, L3-1, and L3-2 TALEN pairs. Bar graph indicating the quantitative difference in specificity score at each position between cleavage using the canonical TALEN pair or TALENs incorporating L3-1 (FIG. 26A) or L3-2 (FIG. 26B), or L2-1 (FIG. 26C) TALEs, all at a dose of 10 nM. Difference scores were calculated as $score_{L2/3}-score_{WT}$. Bases at each position in the target half-sites are displayed. A score of zero indicates no change in specificity. For the right half-site, data for the sense strand are displayed. The sequences, from left to right, correspond to SEQ ID NOs: 15 and 16.
Figure 26B:
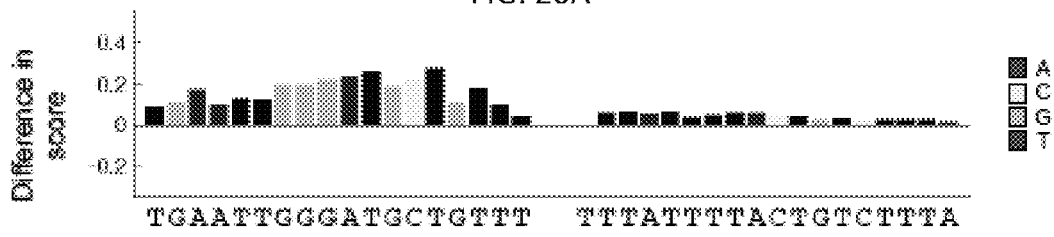
Figure 26C:

Specificity scores were calculated to directly compare the preference of canonical and evolved ATM-L TALEs at each position in the TALEN target site for A, C, G, or T. Scores were calculated by subtracting pre- and post-selection base-pair frequencies, and normalizing values to the maximum possible change of the pre-selection frequency from perfect specificity (1.0) to complete lack of specificity (−1.0). Heat maps and quantitative bar graphs generated for the canonical TALEN pair were in agreement with previously reported observations[30] (FIGS. 4A, 21, 22). Cleavage by TALEN pairs incorporating the evolved TALEs L3-1 or L3-2 exhibited substantially increased specificity relative to that of the canonical TALEN at nearly all positions in the left half-site of the ATM binding sequence, but no substantial change in specificity in the right half-site that was not used during DB-PACE (FIGS. 4B-4D, 23, 24, 25, and 26). Taken together, these results demonstrate that DB-PACE can be used to greatly reduce TALEN cleavage of a specific genomic off-target sequence, and that the resulting specificity enhancements are not confined to that off-target substrate but instead apply to many other off-target sequences.

The behavior of the evolved TALENs in two human cell lines was tested. U2OS cells were nucleofected with a control plasmid, or plasmids expressing heterodimeric FokI fusions to either the canonical ATM-L TALE or evolved L3-1 or L3-2 TALEs, together with a plasmid encoding the canonical ATM-R TALE-FokI fusion protein. After 48 h, genomic DNA was harvested and high-throughput sequencing analysis was performed to examine cleavage at the on-target site, off-target site OffA17, and three additional unrelated off-target sites OffA1, OffA11, and OffA23[30]. Cleavage at the on-target ATM site was comparable for the canonical and evolved TALENs (Tables 1, 2, and 4). Importantly, for all four off-target sites, both evolved TALENs exhibited reduced off-target activity relative to the canonical TALEN (Tables 1 and 4). For example, cleavage of OffA17 was reduced by >16-fold (Tables 1 and 4), and cleavage of OffA11 was reduced by >20-fold (Tables 1 and 4) using either the L3-1 or L3-2 TALENs in human cells versus the canonical TALEN. Comparable on-target activity and improved specificity of the L3-2 TALEN against the two most efficiently cleaved off-target sites, OffA17 and OffA11, using a homodimeric FokI nuclease architecture in HEK 293 cells (Tables 1 and 4). These data establish that DB-PACE can be used to improve the specificity of a DNA-binding domain. Moreover, the results demonstrate that the mutations that confer improved specificity during DB-PACE selection can be applied to other TALE effector contexts, such as incorporation into a TALEN pair for genome modification in human cells with improved DNA specificity.

TABLE 1

Cellular modification rates of the on-target ATM locus and four off-target sites by canonical and evolved TALENs in human U2OS and HEK 293 cells.

| Site | Canonical TALEN (%) | L3-1 TALEN (%) | L3-2 TALEN (%) |
|---|---|---|---|
| U2OS | | | |
| On-target (ATM locus) | 11.00 | 7.040 | 7.970 |
| OffA1 | 0.009 | <0.001 | 0.002 |
| OffA11 | 0.040 | 0.002 | 0.002 |
| OffA17 | 0.017 | <0.001 | <0.001 |
| OffA23 | 0.004 | <0.001 | <0.001 |
| 293 | | | |
| On-target (ATM locus) | 23.74 | ND | 23.26 |
| OffA11 | 0.748 | ND | <0.001 |
| OffA17 | 0.380 | ND | 0.025 |

Cellular modification rates are shown as a percentage based on the number of observed sequences containing insertions or deletions (indels) divided by the total number of genomic DNA fragments sequenced. Full target sites are listed in Table 2, and total sample sizes and P-values are shown in Table 4. ND: no data were collected.

Heterodimeric FokI nuclease (EL/KK) TALENs were used for experiments in U2OS cells, while homodimeric FokI nuclease TALENs were used for experiments in HEK 293 cells.

TABLE 4

Sample size and P value for high-throughput sequencing of TALEN cleavage in U2OS and 293 cells.

| Cell line | TALEN pair | Site | Indels | Total sequences | Percent modified[a] | P-value[b] |
|---|---|---|---|---|---|---|
| U2OS | Control | On-target | 1 | 10000 | 0.010 | |
| U2OS | Control | OffA1 | 0 | 253702 | <0.001 | |
| U2OS | Control | OffA11 | 5 | 421633 | 0.001 | |
| U2OS | Control | OffA17 | 2 | 438269 | <0.001 | |
| U2OS | Control | OffA23 | 2 | 281288 | 0.001 | |
| U2OS | ATM can. (EL/KK) | On-target | 1100 | 10000 | 11.000 | $<1.0 \times 10^{-300}$ |
| U2OS | ATM can. (EL/KK) | OffA1 | 18 | 193251 | 0.009 | $2.8 \times 10^{-7}$ |
| U2OS | ATM can. (EL/KK) | OffA11 | 144 | 357899 | 0.040 | $5.7 \times 10^{-42}$ |
| U2OS | ATM can. (EL/KK) | OffA17 | 95 | 569336 | 0.017 | $4.1 \times 10^{-21}$ |
| U2OS | ATM can. (EL/KK) | OffA23 | 12 | 338944 | 0.004 | $2.8 \times 10^{-2}$ |
| U2OS | L3-1 (EL/KK) | On-target | 704 | 10000 | 7.040 | $1.3 \times 10^{-204}$ |
| U2OS | L3-1 (EL/KK) | OffA1 | 0 | 275541 | <0.001 | |
| U2OS | L3-1 (EL/KK) | OffA11 | 5 | 314087 | 0.002 | |
| U2OS | L3-1 (EL/KK) | OffA17 | 1 | 420626 | <0.001 | |
| U2OS | L3-1 (EL/KK) | OffA23 | 0 | 351725 | <0.001 | |
| U2OS | L3-2 (EL/KK) | On-target | 797 | 10000 | 7.970 | $2.1 \times 10^{-231}$ |
| U2OS | L3-2 (EL/KK) | OffA1 | 4 | 235431 | 0.002 | $5.4 \times 10^{-2}$ |
| U2OS | L3-2 (EL/KK) | OffA11 | 5 | 303362 | 0.002 | |
| U2OS | L3-2 (EL/KK) | OffA17 | 2 | 489318 | <0.001 | |
| U2OS | L3-2 (EL/KK) | OffA23 | 2 | 401692 | <0.001 | |
| 293 | Control | On-target | 74 | 121714 | 0.061 | |
| 293 | Control | OffA11 | 1 | 64667 | <0.001 | |
| 293 | Control | OffA17 | 3 | 191726 | <0.001 | |
| 293 | ATM can. (Homo) | On-target | 23651 | 99604 | 23.745 | $<1.0 \times 10^{-300}$ |
| 293 | ATM can. (Homo) | OffA11 | 290 | 38761 | 0.748 | $8.8 \times 10^{-122}$ |
| 293 | ATM can. (Homo) | OffA17 | 639 | 168318 | 0.380 | $1.2 \times 10^{-204}$ |
| 293 | L3-2 (Homo) | On-target | 20944 | 90030 | 23.263 | $<1.0 \times 10^{-300}$ |
| 293 | L3-2 (Homo) | OffA11 | 0 | 52317 | <0.001 | |

[a] As previously described[56], the sensitivity of the high-throughput sequencing method for detecting genomic off-target cleavage is limited by the amount genomic DNA (gDNA) input into the PCR amplification of each genomic target site. Each sample was run with 600 ng of genomic DNA, equivalent to ~198,000 genomes. Thus, the theoretical detection limit of this technique is approximately 1 in 198,000, which has been indicated as <0.001%.
[b] P values were calculated as previously reported[30, 44] using a (right) one-sided Fisher's exact test between each TALEN-treated sample and the untreated control sample. P values less than the significance threshold, calculated as previously described[30], are not shown.
Indels are the number of observed sequences containing insertions or deletions consistent with TALEN-induced cleavage, and percent modified corresponds to the number of detected sequences containing indels divided by the total number of genomic DNA fragments sequenced multiplied by one hundred.

Discussion

DNA-binding PACE brings the power of continuous evolution to bear on improving the activity and specificity of a variety of DNA-binding proteins, including those relevant to genome editing (in this work, zinc fingers and TALE proteins). A distinguishing feature of DB-PACE is that it does not require the use of targeted libraries that can constrain or bias evolutionary outcomes. As evidenced by the findings of this study, the unconstrained manner in which mutations arise during PACE supports the discovery of evolved solutions with desired properties that could not be rationalized a priori. For example, while two directed evolution studies using combinatorial libraries[28,29] have supported the original notion that TALE specificity at the 5' position is mediated exclusively by W120 (W232 in AvrBs3 structure[48]), the results identify K59 and A79 as two residues that also determine 5' nucleotide specificity.

Figure 13D:
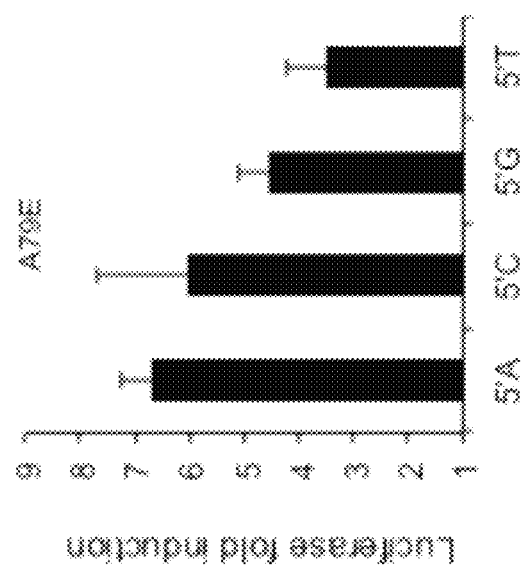

A small cluster of mutations (K59E, A79E, and A133E) arising during 5'-nucleotide-directed evolution were discovered that are predicted to be within an extended N-terminal DNA-binding region[49] near W120. Mutation of A79 or K59 to glutamate resulted in altered 5' specificity (FIGS. 13D and 16C, 16D). While these residues are not predicted to directly contact DNA (FIGS. 13C and 16A), their effects are likely mediated through their interactions with W120, which is predicted to contact the 5' nucleotide. Moreover, DB-PACE to alter 5' nucleotide targeting identified a large number of additional amino acid substitutions throughout the entire TALE sequence, and identified context-dependent effects for residues such as K59E that alter 5' specificity in a non-modular fashion (FIG. 16D). The results therefore support the more recent hypothesis that 5' base specificity is altered in a complex fashion that depends on the context of TALE repeats and their RVD compositions[50-52]. The findings also suggest that TALE proteins with the most desirable properties, including high activity and high specificity, may contain mutations such as K59E that are not entirely modular but rather specific to the TALE protein of interest. Because such mutations are difficult or impossible to predict using standard TALE design principles, DB-PACE may be an ideal method to improve TALE arrays designed by modular assembly.

The data also support recent observations that TALE activity can be altered in an effector-dependent manner[52]. Mutation of Q711 (or equivalent), was present in an unstructured area of the C-terminus (FIG. 13E), to Pro in all PACE experiments performed. While this substitution doubled the activity of TALE-ω fusions (FIG. 13B), likely through introduction of a kink in protein backbone that resulted in more effective presentation of the ω RNAP subunit, it had no effect on TALEN activity (FIG. 19B).

The high efficiency of PACE facilitates the accumulation of many permissive amino acid substitutions in evolving proteins. The results shown in FIG. 13A reveal novel sequence variability within the normally highly conserved core TALE unit. Of particular note are substitutions D4K/N and S11K within the first helix[16], and K16R, T21A, and L26F in the second helix[16], all of which arose in multiple evolution experiments, and in some cases, in multiple different TALE array repeats (FIG. 12). Position K16, as illustrated in the context of a K634R mutation in FIG. 13H, is adjacent to the RVD loop and makes a non-specific DNA contact[16]. These results suggest that Arg may be used as a possible alternative at position 16 for this DNA contact. In addition, it was observed that several RVD substitutions, including replacement of the less specific NN RVD, which targets both G and A[13], with the more specific NK and NH repeats[17], as well as substitution of NG with HG, a repeat present in naturally occurring TALEs that also specifies T, but is not typically used in the design of synthetic TALEs (FIG. 13A)[17]. It has been shown that the highly repetitive nature of TALEN genes is incompatible with lentiviral delivery vectors due to recombination between repeat units arising from "template-switching" during DNA replication[53]. The permissive core amino acid substitutions discovered in this work could enable recoding of TALE arrays to decrease sequence homology and thereby improve the manipulability and application scope of TALE proteins.

The data demonstrate that DB-PACE coupled with in vitro specificity profiling represents a systematic approach to removing specific off-target activities of TALENs. In theory, negative selection against binding to a particular TALE off-target site could result in the emergence of a new off-target activity. However, our broad specificity profiling data suggest that TALEs may possess an inherent degree of promiscuity, possibly arising from excess DNA-binding energy[30], that can be decreased through rapid protein evolution to improve TALE array specificity in a broad manner. It is tempting to speculate that TALEs from *Xanthomonas* may have evolved a degree of promiscuity to enable them to target slightly mutated pathogen sequences inside a plant host, a hypothesis supported by the recent identification of naturally occurring TALEs with the ability to bind target sequence variants with single nucleotide deletions[54]. It is remarkable that a single amino acid substitution, A252T, corresponding to the eighth residue within the third repeat of the ATM-L TALE, can greatly diminish binding of the OffA17 off-target site, which contains mutations at target site nucleotides 1, 5, 12, 16, and 17. Structural analysis predicts that A252 lies in close proximity to the RVD loop (FIG. 19C), and it has been suggested that this residue stabilizes the loop[15,16,55]. It is plausible that mutation of this residue to a larger and more polar Thr residue results in an altered or additional DNA contact, altering specificity of the entire array. The fact that evolved ATM-L TALE L3-2 showed even greater specificity than L3-1 (FIGS. 26A, 26B) and differed only by the presence of L338S suggests that this position is also a determinant of specificity. L338, which corresponds to position 26 in a TALE repeat, is adjacent to P339 (FIG. 19D), a residue that is essential for proper packing of TALE repeats[16]. L338S may adjust repeat packing in a way that decreases excess binding energy and thereby augments specificity.

Figure 27A:
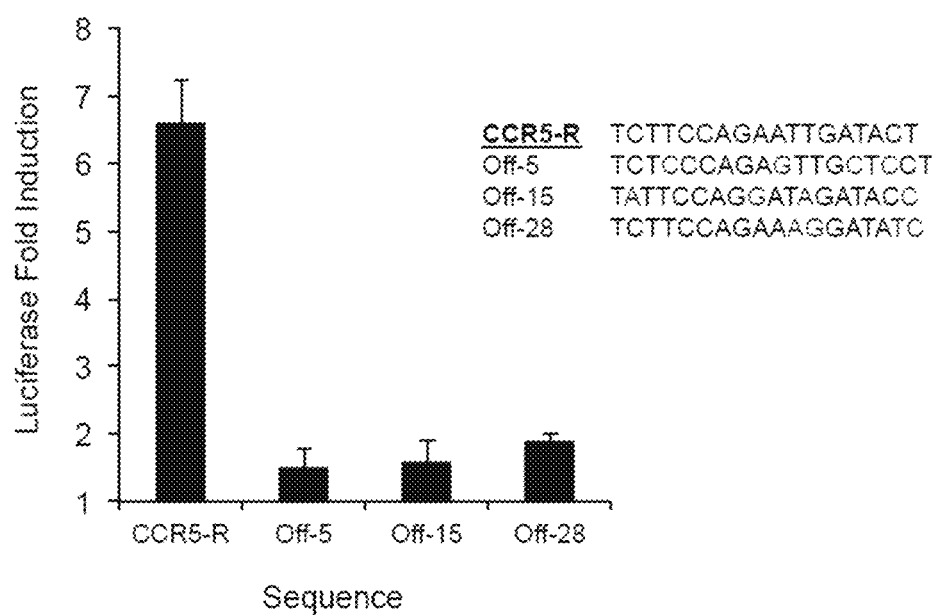
FIG. 27A shows the specificity of a CCR5-targeting TALE in the DB-PACE one-hybrid system. Luciferase activity represented as fold induction (ATc-induced TALE luminescence/non-induced luminescence) for a canonical CCR5-R-directed TALE on its on-target sequence or one of three previously described off-target sequences[30] (Off-5, Off-15, Off-28; sequences indicated in the figure). Data represent mean+s.d. (n=3). The sequences, from top to bottom, correspond to SEQ ID NOs: 59-62.

The development of DB-PACE may facilitate the generation of highly specific genome engineering tools for research or therapeutic applications. For example, DB-PACE could be used to evolve high-affinity matched TALE pairs for accurate SNP detection. Moreover, DB-PACE is amenable to improving the specificity of TALENs targeting loci of clinical relevance such as CCR5[30] (FIG. 27A), as well as improving other genome engineering tools with clinical potential such as Cas9. Accordingly, DB-PACE could be used to remove the undesirable ability of these proteins to modify specific off-target loci, thereby increasing their safety and therapeutic potential.

Materials and Methods

Cloning and Plasmid Construction.

PCR fragments for pOH, pAP, pAPNeg, pJG, and SP plasmids were generated using either PfuTurbo Cx Hotstart (Agilent) or VeraSeq Ultra (Enzymatics) DNA polymerases, and assembled by USER cloning (NEB) according to the manufacturer's instructions. The Q5 Site-Directed Mutagenesis kit (NEB) was used for all site-directed mutagenesis, and to produce minimized pOH plasmids (pTet). DNA encoding TALEN cleavage sites were purchased as gBlocks (IDT) and inserted into pUC19 using XbaI and HindIII restriction enzymes.

Phage-Assisted Continuous Evolution (PACE) of DNA-Binding Domains.

In general, PACE setup was performed as previously described[33]. *E. coli* were maintained in chemostats containing 200 mL of Davis' Rich Media (DRM) using typical flow rates of 1-1.5 vol/h. DRM media was supplemented with appropriate antibiotics to select for transformed plasmids: APs (50 µg/mL carbenicillin), APNegs (75 µg/mL spectinomycin), MPs (25 µg/mL chloramphenicol). Lagoon dilution rates were 1.3-2 vol/h. In all PACE experiments S1030 cells carried an MP, either the previously reported pJC184[33], or a variant of this plasmid lacking RecA, pAB086a. Mutagenesis was induced by continuously injecting arabinose (500 mM) at a rate of 1 mL/h into each 40-mL lagoon. Typical phage titers during each PACE experiment were $10^6$-$10^8$ p.f.u./mL. Specific parameters for each evolution experiment are detailed below.

Reversion of Zif268-V24R.

A lagoon receiving host cell culture from a chemostat containing S1059 cells transformed with an MP was inoculated with Zif268-V24R phage. The lagoon flow rate during drift was 2 vol/h. After 24 h of drift, phage were isolated and used to inoculate a PACE experiment with S1030 host cells carrying pAPZif268 and an MP. Evolved phage were isolated after 24 h and characterized using plaque assays.

Positive Selection of TALEs with Altered 5' Preference (5' A, C, G).

Three parallel evolution experiments were performed to evolve phage with higher affinity for 5' A, 5' C, or 5' G target sequences. For each experiment, two separate lagoons receiving culture from a chemostat containing S1030 cells transformed with the appropriate AP (pAPCBXTAL:5A, pAPCBXTAL:5C, pAPCBXTAL:5G) and an MP were inoculated with SPCBXTAL. PACE proceeded for 48 h at a lagoon dilution rate of 1.3 vol/h prior to harvest and analysis of the resultant phage pools.

Negative Selection to Generate TALEs with 5' A Specificity.

Two separate lagoons receiving culture from a chemostat containing a mixed population of S1030 cells were inoculated with evolved 5' A phage from the positive selection experiment. This *E. coli* population consisted of a 1:1:1 mixture of host cells carrying an APNeg plasmid (pAPNegCBXTAL:5C, pAPNegCBXTAL:5G, or pAPNegCBXTAL:5T) together with pAPCBXTAL:5A and an MP. Over the course of a six-day PACE experiment, an increasing dose of theophylline was added to each lagoon at a rate of 1 mL/h to yield increasing final theophylline lagoon concentrations of 0.1 mM, 0.2 mM, and 0.3 mM (+0.1 mM theophylline every 48 h).

Positive Selection and Negative Selection (OffA17) of ATM-L TALE.

Two separate lagoons receiving culture from a chemostat containing a S1030 cells transformed with pAPATMLTAL, pAPNegATMTAL:OffA17, and an MP were inoculated with SPATMTAL phage. The lagoon flow rate was 1.3 vol/h. Theophylline was added to each lagoon at increasing quantities (+0.1 mM every 24 h), from a starting dose of 0 mM to a final concentration of 0.4 mM; the injection rate into each lagoon was 1 mL/h. After 120 h of PACE, phage from both lagoons were pooled and subjected to an additional 24 h of PACE at a lagoon flow rate of 2 vol/h in the presence of 0.4 mM theophylline.

Luciferase Assay.

pOH plasmids were transformed by electroporation into S1030 cells, and grown overnight at 37° C. on LB-agar plates supplemented with 50 μg/mL carbenicillin. Single colonies were used to inoculate cultures which were allowed to grow for ~12 h at 37° C. in DRM supplemented with 50 μg/mL carbenicillin in a shaker. Cultures were diluted to an $OD_{600}$ of ~0.3 and allowed to grow for an additional 2 h at 37° C. Next, each culture was diluted 1:15 into 300 μL of DRM supplemented with 50 μg/mL carbenicillin in the presence or absence of 200 ng/mL anhydrotetracycline and incubated in a 96-well plate for an additional 4-6 h (shaking). 200 μL aliquots of each sample were then transferred to 96-well opaque plates and luminescence and $OD_{600}$ readings were taken using a Tecan Infinite Pro instrument. Luminescence data were normalized to cell density by dividing by the $OD_{600}$ value.

Plaque Assays.

S1030 cells were transformed with the appropriate plasmids via electroporation and grown in LB media to an $OD_{600}$ of 0.8-1.0. Diluted phage stock samples were prepared ($10^{-4}$, $10^{-5}$, $10^{-6}$, or $10^{-7}$-fold dilution) by adding purified phage stock to 250 μL of cells in Eppendorf tubes. Next, 750 μL of warm top agar (0.75% agar in LB, maintained at 55° C. until use) was added to each tube. Following mixing by pipette, each 1 mL mixture was pipetted onto one quadrant of a quartered petri plate that had previously been prepared with 2 mL of bottom agar (1.5% agar in LB). Following solidification of the top agar, plates were incubated overnight at 37° C. prior to analysis. Colorimetric plaque assays were performed in parallel with regular plaque assays using S2060 cells instead of S1030 cells, and used S-Gal/LB agar blend (Sigma) in place of regular LB-agar.

High-Throughput Analysis of TALE Mutations.

PCR fragments containing evolved phage with ~500 bp of flanking sequence on either end were amplified from minipreps (Qiagen) of cells infected with evolved phage pools using the following primers: HTSFwd-5'-GAAAATATTGT-TGATGCGCTGGCAGTGTTC-'3 (SEQ ID NO: 46), HTSRev-5'-TAGCAGCCTTTACAGAGA-GAATAACATAAAA-'3 (SEQ ID NO: 47). HTS preparation was performed as previously reported using a Nextera kit (Illumina). Briefly, 4 μL of amplified DNA (2.5 ng/μL), 5 μL TD buffer, and 1 μL TDE1 were mixed together and heated at 55° C. for 5 min to perform "tagmentation". Following DNA clean up using a Zymo-Spin column (Zymo), samples were amplified with Illumina-supplied primers according to the manufacturer's instructions. The resulting products were purified using AMPure XP beads (Agencourt), and the final concentration of DNA was quantified by qPCR using PicoGreen (Invitrogen). Samples were sequenced on a MiSeq Sequencer (Illumina) using 2×150 paired-end runs according to the manufacturer's protocols. Analysis of mutation frequency was performed using MATLAB as previously described[32]. Observed background mutation frequencies were subtracted from the mutation frequencies of each experimental sample to account for DNA sequencing errors[32].

YFP Assay.

pTet plasmids were co-transformed with pAPNeg plasmids by electroporation into S1030 cells, and grown overnight at 37° C. on LB-agar plates supplemented with 50 μg/mL carbenicillin and 100 μg/mL spectinomycin. Single colonies were used to inoculate cultures which were allowed to grow for ~12 h in antibiotic-supplemented DRM in a bacterial shaker. Cultures were diluted to an $OD_{600}$ of ~0.3 and allowed to grow for an additional 2 h at 37° C. Next, each culture was diluted 1:15 into 300 μL of DRM supplemented with antibiotics and 5 mM theophylline in the presence or absence of 50 ng/mL anhydrotetracycline and incubated in a 96-well deep well plate for an additional 4-6 h (shaking). 200 μL aliquots of each sample were then transferred to 96-well opaque plates and YFP fluorescence ($\lambda_{ex}$=514 nm, $\lambda_{em}$=527 nm) and $OD_{600}$ readings were taken using a Tecan Infinite Pro instrument. Fluorescence data were normalized to cell density by dividing by the $OD_{600}$ value.

In Vitro TALEN Cleavage Assay.

In vitro TALEN cleavage assays were performed as previously described with slight modifications to the procedure[30]. Briefly, 1 μg of each TALEN-encoding plasmid (pJG) was added individually to 20 μL of methionine-supplemented T7-TnT Coupled Transcription/Translation System (Promega) lysate and incubated for 1.5 h at 30° C. Determination of protein concentrations and preparation of linear DNA for TALEN cleavage was performed as previously reported[30]. Each reaction consisted of 50 ng of amplified DNA, 12 μL NEB Buffer 3, 3 μL of each in vitro transcribed/translated TALEN left and right monomers (corresponding to ~15 nM final TALEN concentration), and 6 μL of empty lysate brought up to a final volume of 120 μL in distilled water. The digestion reaction was allowed to proceed for 30 min at 37° C. (or 1 h where indicated), and then incubated with 1 µg/uL RNase A (Qiagen) for 2 minutes prior to being purified using a Minielute column (Qiagen). Reactions were subsequently run in a 5% TBE Criterion PAGE gel (Bio-rad), and stained with 1×SYBR Gold (Invitrogen) for 10 minutes. Gels were imaged using a Syngene G:BOX Chemi XRQ, and densitometry was performed using GelEval 1.37 software.

High-Throughput Specificity Profiling Assay.

High-throughput specificity profiling of canonical and evolved TALEN pairs and subsequent data analysis was performed as previously described[30].

TALEN Cleavage in HEK 293 and U2OS Cells.

pJG29 and pJG30 plasmids were transfected into HEK 293 cells (a cell line that has a high transfection efficiency; obtained from ATCC) using Lipoject (Signagen) according to the manufacturer's instructions. pJG51 and pJG52 plasmids were nucleofected into U2OS cells as previously described[30]. For both sets of experiments, genomic DNA isolation was performed as previously reported[30,56]. Primers for amplifying on and off-target genomic sites are provided herein. Illumina adapter ligation, AMPure XP bead cleanup (Agencourt), sequencing and post-analysis were performed as previously described[30,56].

Plasmid Construct Information

| Name | Class | Antibio. Res. | Origin of Rep. | Promoter | Binding Site | Gene |
|---|---|---|---|---|---|---|
| pOHZif268-1 | One-hybrid test plasmid | Carb | SC101 | $P_{lac}$ (pIII-luc) $P_{tet}$ (Zif268 fusion) | -55 (Zif268) | pIII-luxAB Zif268 DBD (M)-rpoZ |
| pOHZif268-2 | One-hybrid test plasmid | Carb | SC101 | $P_{lac}$ (pIII-luc) $P_{tet}$ (Zif268 fusion) | -55 (Zif268) | pIII-luxAB Zif268 DBD (L)-rpoZ |
| pOHZif268-3 | One-hybrid test plasmid | Carb | SC101 | $P_{lac}$ (pIII-luc) $P_{tet}$ (Zif268 fusion) | -62 (Zif268) | pIII-luxAB Zif268 DBD (M)-rpoZ |
| pOHZif268-4 | One-hybrid test plasmid | Carb | SC101 | $P_{lac}$ (pIII-luc) $P_{tet}$ (Zif268 fusion) | -62 (Zif268) | pIII-luxAB Zif268 DBD (L)-rpoZ |
| pOHZif268-5 | One-hybrid test plasmid | Carb | SC101 | $P_{lac}$ (pIII-luc) $P_{tet}$ (Zif268 fusion) | -55 (Zif268) | pIII-luxAB rpoZ-(M)-Zif268 DBD |
| pOHZif268-6 | One-hybrid test plasmid | Carb | SC101 | $P_{lac}$ (pIII-luc) $P_{tet}$ (Zif268 fusion) | -55 (Zif268) | pIII-luxAB rpoZ-(L)-Zif268 DBD |
| pOHZif268-7 | One-hybrid test plasmid | Carb | SC101 | $P_{lac}$ (pIII-luc) $P_{tet}$ (Zif268 fusion) | -62 (Zif268) | pIII-luxAB rpoZ-(M)-Zif268 DBD |
| pOHZif268-7: TTA | One-hybrid test plasmid | Carb | SC101 | $P_{lac}$ (pIII-luc) $P_{tet}$ (Zif268 fusion) | -62 5'GCGTTA GCG3' | pIII-luxAB rpoZ-(M)-Zif268 DBD |
| pOHZif268-8 | One-hybrid test plasmid | Carb | SC101 | $P_{lac}$ (pIII-luc) $P_{tet}$ (Zif268 fusion) | -62 (Zif268) | pIII-luxAB rpoZ-(L)-Zif268 DBD |
| pOHZif268-9 | One-hybrid test plasmid | Carb | SC101 | $P_{lac}$ (pIII-luc) $P_{tet}$ (Zif268 fusion) | -55 (Zif268) | pIII-luxAB rpoA-(M)-Zif268 DBD |
| pOHZif268-10 | One-hybrid test plasmid | Carb | SC101 | $P_{lac}$ (pIII-luc) $P_{tet}$ (Zif268 fusion) | -62 (Zif268) | pIII-luxAB rpoA-(M)-Zif268 DBD |
| SPZif268 | SP | Kan | F1 | $P_{gIII}$ | — | rpoZ-(M)-Zif268 DBD |
| SPZif268-R24V | SP | Kan | F1 | $P_{gIII}$ | — | rpoZ-(M)-Zif268 DBD-R24V |

-continued

| Name | Class | Antibio. Res. | Origin of Rep. | Promoter | Binding Site | Gene |
|---|---|---|---|---|---|---|
| pAPZif268 | AP | Carb | SC101 | $P_{lac}$ | −62 (Zif268) | pIII-luxAB |
| pAPZif268: TTA | AP | Carb | SC101 | Plac | −62 5'GCGTTAGCG3' | pIII-luxAB |
| pOHCBXTAL-1 | One-hybrid test plasmid | Carb | SC101 | Plac (pIII-luc) Ptet (CBX8 TALE fusion) | −62 (CBX8) | pIII-luxAB TALE(CBX8)-+28-rpoZ |
| pOHCBXTAL-2 | One-hybrid test plasmid | Carb | SC101 | Plac (pIII-luc) Ptet (CBX8 TALE fusion) | −62 (CBX8) | pIII-luxAB TALE(CBX8)-+40-rpoZ |
| pOHCBXTAL-3 | One-hybrid test plasmid | Carb | SC101 | Plac (pIII-luc) Ptet (CBX8 TALE fusion) | −62 (CBX8) | pIII-luxAB TALE(CBX8)-+63-rpoZ |
| pOHCBXTAL-4 | One-hybrid test plasmid | Carb | SC101 | $P_{lac}$ (pIII-luc) $P_{tet}$ (CBX8 TALE fusion) | −62 (CBX8) | pIII-luxAB TALE(CBX8)-+18G$_4$S-rpoZ |
| pOHCBXTAL-4:Offtarget | One-hybrid test plasmid | Carb | SC101 | $P_{lac}$ (pIII-luc) $P_{tet}$ (CBX8 TALE fusion) | −62 5' TTCATAA GGGATTA GGC3' | pIII-luxAB TALE(CBX8)-+18G$_4$S-rpoZ |
| pOHCBXTAL-4:A79E, A133E, Q711P, A755V V767G | One-hybrid test plasmid | Carb | SC101 | $P_{lac}$ (pIII-luc) $P_{tet}$ (CBX8 TALE fusion) | −62 (CBX8) | pIII-luxAB TALE(CBX8)-+18G$_4$S-rpoZ |
| pOHCBXTAL-4:5A, L1-1..5, L2-1..5, A79E, K59E | One-hybrid test plasmid | Carb | SC101 | $P_{lac}$ (pIII-luc) $P_{tet}$ (CBX8 TALE fusion) | −62 5'ATCAGG AGGGCTT CGGC 3' | pIII-luxAB TALE(CBX8)-+18G$_4$S-rpoZ |
| pOHCBXTAL-4:5C, L1-1..5, L2-1..5, A79E, K59E | One-hybrid test plasmid | Carb | SC101 | $P_{lac}$ (pIII-luc) $P_{tet}$ (CBX8 TALE fusion) | −62 5'CTCAGG AGGGCTT CGGC 3' | pIII-luxAB TALE(CBX8)-+18G$_4$S-rpoZ |
| pOHCBXTAL-4:5G, L1-1..5, L2-1..5, A79E, K59E | One-hybrid test plasmid | Carb | SC101 | $P_{lac}$ (pIII-luc) $P_{tet}$ (CBX8 TALE fusion) | −62 5'GTCAGG AGGGCTT CGGC3' | pIII-luxAB TALE(CBX8)-+18G$_4$S-rpoZ |
| pOHCBXTAL-5 | One-hybrid test plasmid | Carb | SC101 | $P_{lac}$ (pIII-luc) $P_{tet}$ (CBX8 TALE fusion) | −62 (CBX8) | pIII-luxAB TALE(CBX8)-+28G$_4$S-rpoZ |
| SPCBXTAL | SP | Kan | F1 | $P_{gIII}$ | — | TALE(CBX8)-+18G$_4$S-rpoZ |
| pApCBXTAL | AP | Carb | SC101 | $P_{lac}$ | −62 (CBX8) | pIII-luxAB |
| pApCBXTAL:5A | AP | Carb | SC101 | $P_{lac}$ | −62 5'ATCAGG AGGGCTT CGGC 3' | pIII-luxAB |
| pApCBXTAL:5C | AP | Carb | SC101 | $P_{lac}$ | −62 5'CTCAGG AGGGCTT CGGC 3' | pIII-luxAB |
| pApCBXTAL:5G | AP | Carb | SC101 | $P_{lac}$ | −62 5'GTCAGG AGGGCTT CGGC3' | pIII-luxAB |
| pAPCBXTAL:Off target | AP | Carb | SC101 | $P_{lac}$ | −62 5' TTCATAA GGGATTA GGC3' | pIII-luxAB |

| Name | Class | Antibio. Res. | Origin of Rep. | Promoter | Binding Site | Gene |
|---|---|---|---|---|---|---|
| pAPNegCBXTAL: 5A | AP-neg | Spect | ColE1 | $P_{lac}$ | -62 5'ATCAGG AGGGCTT CGGC 3' | TheoRibo-6xHistag-N-C83-Venus |
| pAPNegCBXTAL: 5C | AP-neg | Spect | ColE1 | $P_{lac}$ | -62 5'CTCAGG AGGGCTT CGGC 3' | TheoRibo-6xHistag-N-C83-Venus |
| pAPNegCBXTAL: 5G | AP-neg | Spect | ColE1 | $P_{lac}$ | -62 5'GTCAGG AGGGCTT CGGC 3' | TheoRibo-6xHistag-N-C83-Venus 3' |
| pAPNegCBXTAL: 5T | AP-neg | Spect | ColE1 | $P_{lac}$ | -62 5'TTCAGG AGGGCTT CGGC 3' | TheoRibo-6xHistag-N-C83-Venus |
| pAPNegCBXTAL: Offtarget | AP-neg | Spect | ColE1 | $P_{lac}$ | -62 5' TTCATAA GGGATTA GGC3' | TheoRibo-6xHistag-N-C83-Venus |
| PTetCBXTAL | Inducible TALE express. | Carb | SC101 | $P_{tet}$ (CBX8 TALE fusion) | — | TALE(CBX8)-+18G$_4$S-rpoZ |
| PTetCBXTAL:L1-1, L1-2, L2-1, L2-2 | Inducible TALE express. | Carb | SC101 | $P_{tet}$ (CBX8 TALE fusion) | — | TALE(CBX8)-+18G$_4$S-rpoZ |
| SPATMTAL | SP | Kan | F1 | $P_{gIII}$ | — | TALE(ATM-L)+18G$_4$S-rpoZ |
| pApATMTAL | AP | Carb | SC101 | $P_{lac}$ | -62 (ATM-L) | pIII-luxAB |
| pAPNegATMTAL: OffA17 | AP-neg | Spect | ColE1 | $P_{lac}$ | -62 5'-GAAATGG GATACTG AGT3' | TheoRibo-6xHistag-N-C83-Venus |
| pUC19-On-target | TALEN cleavage | Carb | pMB1 | — | Cleavage site: ATM-L | — |
| pUC19-Off-target, pUC19-OffD1-D4 | TALEN cleavage | Carb | pMB1 | — | Cleavage site: 5'-GAAATGG GATACTG AGT3' or derivative site | — |
| pOHATMTAL | One-hybrid test plasmid | Carb | SC101 | $P_{lac}$ (pIII-luc) $P_{tet}$ (TALE fusion) | -62 (ATM-L) | TALE(ATM-L)-+18G$_4$S-rpoZ |
| pOHATMTAL:L3-1, L3-2 | One-hybrid test plasmid | Carb | SC101 | $P_{lac}$ (pIII-luc) $P_{tet}$ (TALE fusion) | -62 (ATM-L) | TALE(ATM-L)-+18G$_4$S-rpoZ |
| pOHATMTAL: OffA17 | One-hybrid test plasmid | Carb | SC101 | $P_{lac}$ (pIII-luc) $P_{tet}$ (TALE fusion) | -62 5'-GAAATGG GATACTG AGT3' | TALE(ATM-L)-+18G$_4$S-rpoZ |
| pOHATMTAL: OffA17:L3-1, L3-2 | One-hybrid test plasmid | Carb | SC101 | $P_{lac}$ (pIII-luc) $P_{tet}$ (TALE fusion) | -62 5'-GAAATGG GATACTG AGT3' | TALE(ATM-L)-+18G$_4$S-rpoZ |

| Name | Class | Antibio. Res. | Origin of Rep. | Promoter | Binding Site | Gene |
|---|---|---|---|---|---|---|
| pOHATMTAL:5' A, C, G and K59E-5'A, C, G, T | One-hybrid test plasmid | Carb | SC101 | $P_{lac}$ (pIII-luc) $P_{tet}$ (TALE fusion) | −62 (ATM-L) or 5'A, C, G sequence variant | TALE(ATM-L or K59E mut)-+18G$_4$S-rpoZ |
| pOHCCR5TAL, pOHCCR5TAL: Off5, Off15, Off28 | One-hybrid test plasmid | Carb | SC101 | $P_{lac}$ (pIII-luc) $P_{tet}$ (TALE fusion) | 5'-TCTTCCA GAATTGA TACT-'3 or off-target site | TALE(CCR5-R)-+18G$_4$S-rpoZ |
| pAB086a pJG29:L1-1, L1-2, L2-1, L3-1..L3-4, Q745P | MP | Chlor | | | RecA-version of pJC184[33] Backbone information previously described[30] | |
| pJG30 | | | | Backbone information previously described[30] | | |
| pJG51: L3-2 | | | | Backbone information previously described[30] | | |
| pJG52 | | | | Backbone information previously described[30] | | |

Genotypes of Bacterial Strains

| Strain | Genotype |
|---|---|
| S1030 | F' proA+B+ Δ(lacIZY) zzf::Tn10 lacIQ1 PN25-tetR luxCDE/endA1 recA1 galE15 galK16 nupG rpsL ΔlacIZYA araD139 Δ(ara, leu)7697 mcrA Δ(mrr-hsdRMS-mcrBC) proBA::pir116 araE201 ΔrpoZ Δflu ΔcsgABCDEFG ΔpgaC λ– |
| S1059 | F' proA+B+ Δ(lacIZY) zzf::Tn10 lacIQ1 PN25-tetR luxCDE/endA1 recA1 galE15 galK16 nupG rpsL ΔlacIZYA araD139 Δ(ara, leu)7697 mcrA Δ(mrr-hsdRMS-mcrBC) proBA::pir116 araE201 ΔrpoZ λ– pJC175e[33] |
| S1632 | F' proA+B+ Δ(lacIZY) zzf::Tn10 lacIQ1 PN25-tetR luxCDE/endA1 recA1 galE15 galK16 nupG rpsL ΔlacIZYA araD139 Δ(ara, leu)7697 mcrA Δ(mrr-hsdRMS-mcrBC) proBA::pir116 araE201 ΔrpoZ Δflu ΔcsgABCDEFG ΔpgaC ΔpspBC λ– |
| S2058 | F' proA+B+ Δ(lacIZY) zzf::Tn10 lacIQ1 PN25-tetR luxCDE Ppsp lacZ luxR Plux groESL/endA1 recA1 galE15 galK16 nupG rpsL ΔlacIZYA araD139 Δ(ara, leu)7697 mcrA Δ(mrr-hsdRMS-mcrBC) proBA::pir116 araE201 ΔrpoZ Δflu ΔcsgABCDEFG ΔpgaC λ– |
| S2059 | F' proA+B+ Δ(lacIZY) zzf::Tn10 lacIQ1 PN25-tetR luxCDE Ppsp(T1) lacZ luxR Plux groESL/endA1 recA1 galE15 galK16 nupG rpsL ΔlacIZYA araD139 Δ(ara, leu)7697 mcrA Δ(mrr-hsdRMS-mcrBC) proBA::pir116 araE201 ΔrpoZ Δflu ΔcsgABCDEFG ΔpgaC λ– |
| S2060 | F' proA+B+ Δ(lacIZY) zzf::Tn10 lacIQ1 PN25-tetR luxCDE Ppsp(AR2) lacZ luxR Plux groESL/endA1 recA1 galE15 galK16 nupG rpsL ΔlacIZYA araD139 Δ(ara, leu)7697 mcrA Δ(mrr-hsdRMS-mcrBC) proBA::pir116 araE201 ΔrpoZ Δflu ΔcsgABCDEFG ΔpgaC λ– |
| S2208 | F' proA+B+ Δ(lacIZY) zzf::Tn10 lacIQ1 PN25-tetR luxCDE Ppsp(AR2) lacZ luxR Plux groESL/endA1 recA1 galE15 galK16 nupG rpsL ΔlacIZYA araD139 Δ(ara, leu)7697 mcrA Δ(mrr-hsdRMS-mcrBC) proBA::pir116 araE201 ΔrpoZ Δflu ΔcsgABCDEFG ΔpgaC λ– pJC175e[33] |

Primer Sequences Used to Amplify On- and Off-Target ATM Genomic Sites

OnATM F:
(SEQ ID NO: 26)
5'GGAGTTCAGACGTGTGCTCTTCCGATCTAGCGCCTGATTCGAGATCCT-'3

OnATM R:
(SEQ ID NO: 27)
5'-CACTCTTTCCCTACACGACGCTCTTCCGATCTNNNNATGCCAAATTCATATGCAAGGC-'3

OffA-1F:
(SEQ ID NO: 28)
5'-GGAGTTCAGACGTGTGCTCTTCCGATCTCCTGCCATTGAATTCCAGCCT-'3

OffA-1R:
(SEQ ID NO: 29)
5'-CACTCTTTCCCTACACGACGCTCTTCCGATCTNNNNTGTCTGCCTTTCCTGTCCCC-'3

-continued

OffA-11F:
5'-
GGAGTTCAGACGTGTGCTCTTCCGATCTTGCAGCTACGGATGAAAACCA

T-'3

OffA-11R:
(SEQ ID NO: 30)
5'-CACTCTTTCCCTACACGACGCTCTTCCGATCTNNNNTCAGAATACCT

CCCCGCCAG-'3

OffA-17F:
(SEQ ID NO: 31)
5'-GGAGTTCAGACGTGTGCTCTTCCGATCTGGTGGAACAATCCACCTGT

ATTAGC-'3

OffA-17R:
(SEQ ID NO: 32)
5'-CACTCTTTCCCTACACGACGCTCTTCCGATCTNNNNGAATGTGACAC

CACCACCGC-'3

OffA-23F:
(SEQ ID NO: 33)
5'-GGAGTTCAGACGTGTGCTCTTCCGATCTTGTTTAGTAATTAAGACCC

TGGCTTTC-'3

OffA-23R:
(SEQ ID NO: 34)
5-'CACTCTTTCCCTACACGACGCTCTTCCGATCTNNNNGCGACAGGTAC

AAAGCAGTCCAT-'3

DNA Sequence of ω-Zif268-DBD Fusion Protein

Bases 997-1260 of *M. musculus* Zif268, corresponding the zinc finger DNA-binding domain (residues 333-420)[37], were cloned in downstream of the RNAP ω subunit. Bases 997-1260 of *M. musculus* Zif268

(SEQ ID NO: 44)
5'ATGGCACGCGTAACTGTTCAGGACGCTGTAGAGAAAATTGGTAACCGT

TTTGACCTGGTACTGGTCGCCGCGCGTCGCGCTCGTCAGATGCAGGTAGG

CGGAAAGGATCCGCTGGTACCGGAAGAAACGATAAAACCACTGTAATC

GCGCTGCGCGAAATCGAAGAAGGTCTGATCAACAACCAGATCCTCGACG

TTCGCGAACGCCAGGAACAGCAAGAGCAGGAAGCCGCTGAATTACAAGCC

GTTACCGCTATTGCTGAAGGTCGTCGTGCGGCGGGCGGCGGCGGCAGCA

CCGCGGCGGCTGAACGCCCATATGCTTGCCCTGTCGAGTCCTGCGATCG

CCGCTTTTCTCGCTCGGATGAGCTTACCCGCCATATCCGCATCCACACAG

GCCAGAAGCCCTTCCAGTGTCGAATCTGCATGCGTAACTTCAGTCGTAG

TGACCACCTTACCACCCACATCCGCACCCACACAGGCGAGAAGCCTTTT

GCCTGTGACATTTGTGGGAGGAAGTTTGCCAGGAGTGATGAACGCAAGA

GGCATACCAAAATCCA TTTAAGACAGAAGTAA-3'

Coding Sequence for ω-Zif268-DBD Fusion Protein

The protein sequence of the ω-Zif268-DBD fusion protein is shown below. The residues highlighted in bold correspond to the ω subunit, while the underlined correspond to the 11-amino acid linker. Residues shown in italics comprise the Zif268-DBD (residues 333-420)[37]. ω-Zif268-DBD fusion protein:

(SEQ ID NO: 45)
MARVTVQDAVEKIGNRFDLVLVAARRARQMQVGGKDPLVPEENDKTTVIA

LREIEEGLINNQILDVRERQEQQEQEAAELQAVTAIAEGRRA<u>AGGGGSTA</u>

<u>AAER</u>*PYACPVESCDRRFSRSDELTRHIRIHTGQKPFQCRICMRNFSRSD*

*HLTTHIRTHTGEKPFACDICGRKFARSDERKRHTKIHLRQK*

Coding Sequences for CBX8- and ATM-L-Directed TALE-ω Fusion Proteins

DNA sequences for the CBX8-directed TALE[18,20] and the ATM-L directed TALE[18, 20, 30] have previously been reported. The protein sequences of both TALE-ω fusion proteins are included below, indicating the appropriate residue numbering convention used in this manuscript. The unformatted residues comprise an N-terminal Flag-tag and NLS sequence, while the bold residues correspond to the canonical N-terminal TALE sequence. TALE repeats are italicized, the C-terminal region and linker sequence underlined, and the ω subunit is in bold and italicized. The DNA and protein sequences for the CCR5-R TALE have also been previously reported[30]. The fusion architecture for the CCR5-R TALE-ω protein is identical to that of the CBX8 and ATM-L-directed TALEs described below.

CBX8-Directed TALE-ω Fusion Protein:

(SEQ ID NO: 11)
MDYKDHDGDYKDHDIDYKDDDDKMAPKKKRKVGIHRGVPMVDLRTLGYSQ

QQQEKIKPKVRSTVAQHHEALVGHGFTHAHIVALSQHPAALGTVAVKYQD

MIAALPEATHEAIVGVGKQWSGARALEALLTVAGELRGPPLQLDTGQLLK

IAKRGGVTAVEAVHAWRNALTGAPLN<u>L</u>*TPDQVVAIASNGGGKQALETVQR*

*LLPVLCQDHGLTPEQVVAIASHDGGKQALETVQRLLPVLCQAHGLTPDQV*

*VAIASNIGGKQALETVQRLLPVLCQAHGLTPAQVVAIANNNGGKQALETV*

*QRLLPVLCQDHG*

*LTPDQVVAIANNNGGKQALETVQRLLPVLCQDHGLTPEQVVAIASNIGG*

*KQALETVQRLLPVLCQAHGLTPDQVVAIANNNGGKQALETVQRLLPV*

*LCQAHGLTPAQVVAIANNNGGKQALETVQRLLPVLCQDHGLTPDQVVAIA*

*NNNGGKQALETVQRLLPVLCQDHGLTPEQVVAIASHDGGKQALETVQR*

*LLPVLCQAHGLTPDQVVAIASNGGGKQALETVQRLLPVLCQAHGLTP*

*AQVVAIASNGGGKQALETVQRLLPVLCQDHGLTPDQVVAIASHDGGKQAL*

*ETVQRLLPVLCQDHGLTPEQVVAIANNNGGKQALETVQRLLPVLCQAHGL*

*TPDQVVAIANNNGGKQALETVQRLLPVLCQAHGLTPEQVVAIASHDGGR*

*PALE*<u>SIVAQLSRPDPALAALTNGGGGS</u>*ARVTVQDAVEKIGNRFDLVL*

*VAARRARQMQVGGKDPLVPEENDKTTVALREIEEGLINNQILDVRERQEQ*
*QEQEAAELQAVTAIAEGRR*

ATM-Directed TALE-ω Fusion Protein:

(SEQ ID NO: 13)
MDYKDHDGDYKDHDIDYKDDDDKMAPKKKRKVGIHRGVPMVDLRTLGYSQ

QQQEKIKPKVRSTVAQHHEALVGHGFTHAHIVALSQHPAALGTVAVKYQ

DMIAALPEATHEAIVGVGKQWSGARALEALLTVAGELRGPPLQLDTGQL

LKIAKRGGVTAVEAVHAWRNALTGAPLN<u>L</u>*TPDQVVAIANNNGGKQALET*

*VQRLLPVLCQDHGLTPEQVVAIASNIGGKQALETVQRLLPVLCQAHGLT*

```
PDQVVAIASNIGGKQALETVQRLLPVLCQAHGLTPAQVVAIASNGGGKQ

ALETVQRLLPVLCQDHGLTPDQVVAIASNGGGKQALETVQRLLPVLCQD

HG

LTPEQVVAIANNNGGKQALETVQRLLPVLCQAHGLTPDQVVAIANNNGGK

QALETVQRLLPVLCQAHGLTPAQVVAIANNNGGKQALETVQRLLPVLCQD

HGLTPDQVVAIASNIGGKQALETVQRLLPVLCQDHGLTPEQVVAIASNGG

GKQALETVQRLLPVLCQAHGLTPDQVVAIANNNGGKQALETVQRLLPVLC

QAHGLTPAQVVAIASHDGGKQALETVQRLLPVLCQDHGLTPDQVVAIASN

GGGKQALETVQRLLPVLCQDHGLTPEQVVAIANNNGGKQALETVQRLLPV

LCQAHGLTPDQVVAIASNGGGKQALETVQRLLPVLCQAHGLTPAQVVAIA

SNGGGKQALETVQRLLPVLCQDHGLTPEQVVAIASNGGGRPALESIVAQL

SRPDPALAALTNGGGGS
ARVTVQDVVEKIGNRFDLVLVAARRARQMQVGGKDPLVPEE
NDKTTVIALREIEEGLI

NNQILDVRERQEQQEQEAAEIQAVTAIAEGRR
```

REFERENCES

1. Tebas, P. et al. Gene editing of CCR5 in autologous CD4 T cells of persons infected with HIV. *N Engl J Med* 370, 901-10 (2014).
2. Genovese, P. et al. Targeted genome editing in human repopulating haematopoietic stem cells. *Nature* 510, 235-40 (2014).
3. Thierry, A. & Dujon, B. Nested chromosomal fragmentation in yeast using the meganuclease I-Sce I: a new method for physical mapping of eukaryotic genomes. *Nucleic Acids Res* 20, 5625-31 (1992).
4. Epinat, J. C. et al. A novel engineered meganuclease induces homologous recombination in yeast and mammalian cells. *Nucleic Acids Res* 31, 2952-62 (2003).
5. Chen, J. W., Evans, B. R., Yang, S. H., Teplow, D. B. & Jayaram, M. Domain of a yeast site-specific recombinase (Flp) that recognizes its target site. *Proc Natl Acad Sci USA* 88, 5944-8 (1991).
6. Jinek, M. et al. A programmable dual-RNA-guided DNA endonuclease in adaptive bacterial immunity. *Science* 337, 816-21 (2012).
7. Gaj, T., Gersbach, C. A. & Barbas, C. F., 3rd. ZFN, TALEN, and CRISPR/Cas-based methods for genome engineering. *Trends Biotechnol* 31, 397-405 (2013).
8. Klug, A. The discovery of zinc fingers and their development for practical applications in gene regulation and genome manipulation. *Q Rev Biophys* 43, 1-21 (2010).
9. Wolfe, S. A., Nekludova, L. & Pabo, C. O. DNA recognition by Cys2His2 zinc finger proteins. *Annu Rev Biophys Biomol Struct* 29, 183-212 (2000).
10. Maeder, M. L. et al. Rapid "open-source" engineering of customized zinc-finger nucleases for highly efficient gene modification. *Mol Cell* 31, 294-301 (2008).
11. Sander, J. D. et al. Selection-free zinc-finger-nuclease engineering by context-dependent assembly (CoDA). *Nat Methods* 8, 67-9 (2011).
12. Beerli, R. R., Segal, D. J., Dreier, B. & Barbas, C. F., 3rd. Toward controlling gene expression at will: specific regulation of the erbB-2/HER-2 promoter by using polydactyl zinc finger proteins constructed from modular building blocks. *Proc Natl Acad Sci USA* 95, 14628-33 (1998).
13. Moscou, M. J. & Bogdanove, A. J. A simple cipher governs DNA recognition by TAL effectors. *Science* 326, 1501 (2009).
14. Boch, J. et al. Breaking the code of DNA binding specificity of TAL-type III effectors. *Science* 326, 1509-12 (2009).
15. Deng, D. et al. Structural basis for sequence-specific recognition of DNA by TAL effectors. *Science* 335, 720-3 (2012).
16. Mak, A. N., Bradley, P., Cernadas, R. A., Bogdanove, A. J. & Stoddard, B. L. The crystal structure of TAL effector PthXo1 bound to its DNA target. *Science* 335, 716-9 (2012).
17. Cong, L., Zhou, R., Kuo, Y. C., Cunniff, M. & Zhang, F. Comprehensive interrogation of natural TALE DNA-binding modules and transcriptional repressor domains. *Nat Commun* 3, 968 (2012).
18. Reyon, D. et al. Engineering customized TALE nucleases (TALENs) and TALE transcription factors by fast ligation-based automatable solid-phase high-throughput (FLASH) assembly. *Curr Protoc Mol Biol* Chapter 12, Unit 12 16 (2013).
19. Cermak, T. et al. Efficient design and assembly of custom TALEN and other TAL effector-based constructs for DNA targeting. *Nucleic Acids Res* 39, e82 (2011).
20. Miller, J. C. et al. A TALE nuclease architecture for efficient genome editing. *Nat Biotechnol* 29, 143-8 (2011).
21. Bedell, V. M. et al. In vivo genome editing using a high-efficiency TALEN system. *Nature* 491, 114-8 (2012).
22. Maeder, M. L. et al. Targeted DNA demethylation and activation of endogenous genes using programmable TALE-TET1 fusion proteins. *Nat Biotechnol* 31, 1137-42 (2013).
23. Mendenhall, E. M. et al. Locus-specific editing of histone modifications at endogenous enhancers. *Nat Biotechnol* 31, 1133-6 (2013).
24. Maeder, M. L. et al. Robust, synergistic regulation of human gene expression using TALE activators. *Nat Methods* 10, 243-5 (2013).
25. Perez-Pinera, P. et al. Synergistic and tunable human gene activation by combinations of synthetic transcription factors. *Nat Methods* 10, 239-42 (2013).
26. Bogdanove, A. J., Schornack, S. & Lahaye, T. TAL effectors: finding plant genes for disease and defense. *Curr Opin Plant Biol* 13, 394-401 (2010).
27. Kim, Y. et al. A library of TAL effector nucleases spanning the human genome. *Nat Biotechnol* 31, 251-8 (2013).
28. Lamb, B. M., Mercer, A. C. & Barbas, C. F., 3rd. Directed evolution of the TALE N-terminal domain for recognition of all 5' bases. *Nucleic Acids Res* 41, 9779-85 (2013).
29. Tsuji, S., Futaki, S. & Imanishi, M. Creating a TALE protein with unbiased 5'-T binding. *Biochem Biophys Res Commun* 441, 262-5 (2013).
30. Guilinger, J. P. et al. Broad specificity profiling of TALENs results in engineered nucleases with improved DNA-cleavage specificity. *Nat Methods* 11, 429-35 (2014).
31. Esvelt, K. M., Carlson, J. C. & Liu, D. R. A system for the continuous directed evolution of biomolecules. *Nature* 472, 499-503 (2011).
32. Dickinson, B. C., Leconte, A. M., Allen, B., Esvelt, K. M. & Liu, D. R. Experimental interrogation of the path 33. Carlson, J. C., Badran, A. H., Guggiana-Nilo, D. A. & Liu, D. R. Negative selection and stringency modulation in phage-assisted continuous evolution. *Nat Chem Biol* 10, 216-22 (2014).
34. Leconte, A. M. et al. A population-based experimental model for protein evolution: effects of mutation rate and selection stringency on evolutionary outcomes. *Biochemistry* 52, 1490-9 (2013).
35. Dickinson, B. C., Packer, M. S., Badran, A. H. & Liu, D. R. A system for the continuous directed evolution of proteases rapidly reveals drug-resistance mutations. *Nat Commun* 5, 5352 (2014).
36. Hu, J. C., Kornacker, M. G. & Hochschild, A. *Escherichia coli* one- and two-hybrid systems for the analysis and identification of protein-protein interactions. *Methods* 20, 80-94 (2000).
37. Choo, Y. & Klug, A. Toward a code for the interactions of zinc fingers with DNA: selection of randomized fingers displayed on phage. *Proc Natl Acad Sci USA* 91, 11163-7 (1994).
38. Durai, S., Bosley, A., Abulencia, A. B., Chandrasegaran, S. & Ostermeier, M. A bacterial one-hybrid selection system for interrogating zinc finger-DNA interactions. *Comb Chem High Throughput Screen* 9, 301-11 (2006).
39. Beekwilder, J., Rakonjac, J., Jongsma, M. & Bosch, D. A phagemid vector using the *E. coli* phage shock promoter facilitates phage display of toxic proteins. *Gene* 228, 23-31 (1999).
40. Elrod-Erickson, M. & Pabo, C. O. Binding studies with mutants of Zif268. Contribution of individual side chains to binding affinity and specificity in the Zif268 zinc finger-DNA complex. *J Biol Chem* 274, 19281-5 (1999).
41. Lynch, S. A. & Gallivan, J. P. A flow cytometry-based screen for synthetic riboswitches. *Nucleic Acids Res* 37, 184-92 (2009).
42. Juillerat, A. et al. Comprehensive analysis of the specificity of transcription activator-like effector nucleases. *Nucleic Acids Res* 42, 5390-402 (2014).
43. Smith, C. et al. Whole-genome sequencing analysis reveals high specificity of CRISPR/Cas9 and TALEN-based genome editing in human iPSCs. *Cell Stem Cell* 15, 12-3 (2014).
44. Pattanayak, V., Ramirez, C. L., Joung, J. K. & Liu, D. R. Revealing off-target cleavage specificities of zinc-finger nucleases by in vitro selection. *Nat Methods* 8, 765-70 (2011).
45. Pattanayak, V. et al. High-throughput profiling of off-target DNA cleavage reveals RNA-programmed Cas9 nuclease specificity. *Nat Biotechnol* 31, 839-43 (2013).
46. Frock, R. L. et al. Genome-wide detection of DNA double-stranded breaks induced by engineered nucleases. *Nat Biotechnol* (2014).
47. Tsai, S. Q. et al. GUIDE-seq enables genome-wide profiling of off-target cleavage by CRISPR-Cas nucleases. *Nat Biotechnol* (2014).
48. Stella, S. et al. Structure of the AvrBs3-DNA complex provides new insights into the initial thymine-recognition mechanism. *Acta Crystallogr D Biol Crystallogr* 69, 1707-16 (2013).
49. Gao, H., Wu, X., Chai, J. & Han, Z. Crystal structure of a TALE protein reveals an extended N-terminal DNA binding region. *Cell Res* 22, 1716-20 (2012).
50. Schreiber, T. & Bonas, U. Repeat 1 of TAL effectors affects target specificity for the base at position zero. *Nucleic Acids Res* 42, 7160-9 (2014).
51. Meckler, J. F. et al. Quantitative analysis of TALE-DNA interactions suggests polarity effects. *Nucleic Acids Res* 41, 4118-28 (2013).
52. Doyle, E. L. et al. TAL effector specificity for base 0 of the DNA target is altered in a complex, effector- and assay-dependent manner by substitutions for the tryptophan in cryptic repeat −1. *PLoS One* 8, e82120 (2013).
53. Holkers, M. et al. Differential integrity of TALE nuclease genes following adenoviral and lentiviral vector gene transfer into human cells. *Nucleic Acids Res* 41, e63 (2013).
54. Richter, A. et al. A TAL effector repeat architecture for frameshift binding. *Nat Commun* 5, 3447 (2014).
55. Wicky, B. I., Stenta, M. & Dal Peraro, M. TAL effectors specificity stems from negative discrimination. *PLoS One* 8, e80261 (2013).
56. Zuris, J. A. et al. Cationic lipid-mediated delivery of proteins enables efficient protein-based genome editing in vitro and in vivo. *Nat Biotechnol* (2014).
57. Dworkin, J., Jovanovic, G. & Model, P. Role of upstream activation sequences and integration host factor in transcriptional activation by the constitutively active prokaryotic enhancer-binding protein PspF. *J Mol Biol* 273, 377-88 (1997).
58. Wang, L. & Gralla, J. D. Multiple in vivo roles for the −12-region elements of sigma 54 promoters. *J Bacteriol* 180, 5626-31 (1998).

SEQUENCES

Exemplary Canonical N-Terminal TALE Domain:

(SEQ ID NO: 1)
VDLRTLGYSQQQQEKIKPKVRSTVAQHHEALVGHGFTHAHIVALSQHPAA

LGTVAVKYQDMIAALPEATHEAIVGVGKQWSGARALEALLTVAGELRGP

PLQLDTGQLLKIAKRGGVTAVEAVHAWRNALTGAPLN

Generic Formula of a TALE Repeat Sequence:

(SEQ ID NO: 2)
LTPX$_1$QVVAIAX$_2$X$_3$X$_4$GGX$_5$X$_6$ALETVQRLLPVLCQX$_7$HG

In SEQ ID NO: 2, above, $X_1$ is D, E or A, $X_2$ is S or N, $X_3$ is N or H, $X_4$ is G, D, I, or N, $X_5$ is K or R, $X_6$ is Q or P, and/or $X_7$ is D or A.

Exemplary, Canonical C-Terminal TALE Domain:

(SEQ ID NO: 3)
SIVAQLSRPDPALAALTNDHLVALACLGGRPALDAVKKGLPHAPALIKR

TNRRIPERTSHRVA

Amino Acid Residues 1-28 of Exemplary Canonical C-Terminal TALE domain:

(SEQ ID NO: 4)
SIVAQLSRPDPALAALTNDHLVALACLG

Amino Acid Residues 1-18 of an Exemplary Canonical C-Terminal TALE domain:

(SEQ ID NO: 5)
SIVAQLSRPDPALAALTN

Exemplary CBX8-Targeting TALE Repeat Array:

(SEQ ID NO: 6)
LTPDQVVAIASNGGGKQALETVQRLLPVLCQDHGLTPEQVVAIASHDGGK
QALETVQRLLPVLCQAHGLTPDQVVAIASNIGGKQALETVQRLLPVLCQA
HGLTPAQVVAIANNNGGKQALETVQRLLPVLCQDHGLTPDQVVAIANNNG
GKQALETVQRLLPVLCQDHGLTPEQVVAIASNIGGKQALETVQRLLPVLC
QAHGLTPDQVVAIANNNGGKQALETVQRLLPVLCQAHGLTPAQVVAIANN
NGGKQALETVQRLLPVLCQDHGLTPDQVVAIANNNGGKQALETVQRLLPV
LCQDHGLTPEQVVAIASHDGGKQALETVQRLLPVLCQAHGLTPDQVVAIA
SNGGGKQALETVQRLLPVLCQAHGLTPAQVVAIASNGGGKQALETVQRLL
PVLCQDHGLTPDQVVAIASHDGGKQALETVQRLLPVLCQDHGLTPEQVVA
IANNNGGKQALETVQRLLPVLCQAHGLTPDQVVAIANNNGGKQALETVQR
LLPVLCQAHGLTPEQVVAIASHDGGRPALE

Exemplary CBX8-Targeting TALE (Comprising an N-Terminal Domain, a TALE Repeat Array and an 18 Amino Acid C-Terminal Domain):

(SEQ ID NO: 7)
VDLRTLGYSQQQQEKIKPKVRSTVAQHHEALVGHGFTHAHIVALSQHPAA
LGTVAVKYQDMIAALPEATHEAIVGVGKQWSGARALEALLTVAGELRGPP
LQLDTGQLLKIAKRGGVTAVEAVHAWRNALTGAPLNLTPDQVVAIASNGG
GKQALETVQRLLPVLCQDHGLTPEQVVAIASHDGGKQALETVQRLLPVLC
QAHGLTPDQVVAIASNIGGKQALETVQRLLPVLCQAHGLTPAQVVAIANN
NGGKQALETVQRLLPVLCQDHGLTPDQVVAIANNNGGKQALETVQRLLPV
LCQDHGLTPEQVVAIASNIGGKQALETVQRLLPVLCQAHGLTPDQVVAIA
NNNGGKQALETVQRLLPVLCQAHGLTPAQVVAIANNNGGKQALETVQRLL
PVLCQDHGLTPDQVVAIANNNGGKQALETVQRLLPVLCQDHGLTPEQVVA
IASHDGGKQALETVQRLLPVLCQAHGLTPDQVVAIASNGGGKQALETVQR
LLPVLCQAHGLTPAQVVAIASNGGGKQALETVQRLLPVLCQDHGLTPDQV
VAIASHDGGKQALETVQRLLPVLCQDHGLTPEQVVAIANNNGGKQALETV
QRLLPVLCQAHGLTPDQVVAIANNNGGKQALETVQRLLPVLCQAHGLTPE
QVVAIASHDGGRPALESIVAQLSRPDPALAALTN

Exemplary Linker Sequence:

(SEQ ID NO: 8)
GGGGS

Exemplary N-Terminal FLAG and NLS:

(SEQ ID NO: 9)
MDYKDHDGDYKDHDIDYKDDDDKMAPKKKRKVGIHRGVP

Exemplary RNAPω Domain:

(SEQ ID NO: 10)
ARVTVQDAVEKIGNRFDLVLVAARRARQMQVGGKDPLVPEENDKTTVIAL
REIEEGLINNQILDVRERQEQQEQEAAELQAVTAIAEGRR

Exemplary CBX8-Targeting TALE Construct with FLAG, NLS, and RNAPω:

(SEQ ID NO: 11)
MDYKDHDGDYKDHDIDYKDDDDKMAPKKKRKVGIHRGVPMVDLRTLGYSQ
QQQEKIKPKVRSTVAQHHEALVGHGFTHAHIVALSQHPAALGTVAVKYQD
MIAALPEATHEAIVGVGKQWSGARALEALLTVAGELRGPPLQLDTGQLLK
IAKRGGVTAVEAVHAWRNALTGAPLNLTPDQVVAIASNGGGKQALETVQR
LLPVLCQDHGLTPEQVVAIASHDGGKQALETVQRLLPVLCQAHGLTPDQV
VAIASNIGGKQALETVQRLLPVLCQAHGLTPAQVVAIANNNGGKQALETV
QRLLPVLCQDHGLTPDQVVAIANNNGGKQALETVQRLLPVLCQDHGLTPE
QVVAIASNIGGKQALETVQRLLPVLCQAHGLTPDQVVAIANNNGGKQALE
TVQRLLPVLCQAHGLTPAQVVAIANNNGGKQALETVQRLLPVLCQDHGLT
PDQVVAIANNNGGKQALETVQRLLPVLCQDHGLTPEQVVAIASHDGGKQA
LETVQRLLPVLCQAHGLTPDQVVAIASNGGGKQALETVQRLLPVLCQAHG
LTPAQVVAIASNGGGKQALETVQRLLPVLCQDHGLTPDQVVAIASHDGGK
QALETVQRLLPVLCQDHGLTPEQVVAIANNNGGKQALETVQRLLPVLCQA
HGLTPDQVVAIANNNGGKQALETVQRLLPVLCQAHGLTPEQVVAIASHDG
GRPALESIVAQLSRPDPALAALTNGGGGSARVTVQDAVEKIGNRFDLVLV
AARRARQMQVGGKDPLVPEENDKTTVIALREIEEGLINNQILDVRERQEQ
QEQEAAELQAVTAIAEGRR

Exemplary ATM-L-Targeting TALE Repeat Array:

(SEQ ID NO: 12)
LTPDQVVAIANNNGGKQALETVQRLLPVLCQDHGLTPEQVVAIASNIGGK
QALETVQRLLPVLCQAHGLTPDQVVAIASNIGGKQALETVQRLLPVLCQA
HGLTPAQVVAIASNGGGKQALETVQRLLPVLCQDHGLTPDQVVAIASNGG
GKQALETVQRLLPVLCQDHGLTPEQVVAIANNNGGKQALETVQRLLPVLC
QAHGLTPDQVVAIANNNGGKQALETVQRLLPVLCQAHGLTPAQVVAIANN
NGGKQALETVQRLLPVLCQDHGLTPDQVVAIASNIGGKQALETVQRLLPV
LCQDHGLTPEQVVAIASNGGGKQALETVQRLLPVLCQAHGLTPDQVVAIA
NNNGGKQALETVQRLLPVLCQAHGLTPAQVVAIASHDGGKQALETVQRLL
PVLCQDHGLTPDQVVAIASNGGGKQALETVQRLLPVLCQDHGLTPEQVVA
IANNNGGKQALETVQRLLPVLCQAHGLTPDQVVAIASNGGGKQALETVQR
LLPVLCQAHGLTPAQVVAIASNGGGKQALETVQRLLPVLCQDHGLTPEQV
VAIASNGGGRPALE

Exemplary ATM-Targeting TALE Construct with FLAG, NLS, and RNAPω:

(SEQ ID NO: 13)
MDYKDHDGDYKDHDIDYKDDDDKMAPKKKRKVGIHRGVPMVDLRTLGYSQ

QQQEKIKPKVRSTVAQHHEALVGHGFTHAHIVALSQHPAALGTVAVKYQD

MIAALPEATHEAIVGVGKQWSGARALEALLTVAGELRGPPLQLDTGQLLK

IAKRGGVTAVEAVHAWRNALTGAPLNLTPDQVVAIANNNGGKQALETVQR

LLPVLCQDHGLTPEQVVAIASNIGGKQALETVQRLLPVLCQAHGLTPDQV

VAIASNIGGKQALETVQRLLPVLCQAHGLTPAQVVAIASNGGGKQALETV

QRLLPVLCQDHGLTPDQVVAIASNGGGKQALETVQRLLPVLCQDHGLTPE

QVVAIANNNGGKQALETVQRLLPVLCQAHGLTPDQVVAIANNNGGKQALE

TVQRLLPVLCQAHGLTPAQVVAIANNNGGKQALETVQRLLPVLCQDHGLT

PDQVVAIASNIGGKQALETVQRLLPVLCQDHGLTPEQVVAIASNGGGKQA

LETVQRLLPVLCQAHGLTPDQVVAIANNNGGKQALETVQRLLPVLCQAHG

LTPAQVVAIASHDGGKQALETVQRLLPVLCQDHGLTPDQVVAIASNGGGK

QALETVQRLLPVLCQDHGLTPEQVVAIANNNGGKQALETVQRLLPVLCQA

HGLTPDQVVAIASNGGGKQALETVQRLLPVLCQAHGLTPAQVVAIASNGG

GKQALETVQRLLPVLCQDHGLTPEQVVAIASNGGGRPALESIVAQLSRPD

PALAALTNGGGGSARVTVQDVVEKIGNRFDLVLVAARRARQMQVGGKDPL

VPEENDKTTVIALREIEEGLINNQILDVRERQEQQEQEAAELQAVTAIAE

GRR

Exemplary FokI Nuclease Domain:

(SEQ ID NO: 14)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINF

Exemplary ATM Off Target Left and Right Half-Sites, OffA1:

(SEQ ID NO: 17)
TGAATaGGaAataTaTTT (SEQ ID NO: 18)
TTTATTTTACTGTtTTTA

Exemplary ATM Off Target Left and Right Half-Sites, OffA11:

(SEQ ID NO: 19)
TGAATTGaGAgaagcaTT (SEQ ID NO: 20)
TTTATTTTAtTaTtTTTA

Exemplary ATM Off Target Left and Right Half-Sites, OffA17:

(SEQ ID NO: 21)
gGAAaTGGGATaCTGagT (SEQ ID NO: 22)
TTTATgTTACTaTtTcTA

Exemplary ATM Off Target Left and Right Half-Sites, OffA23:

(SEQ ID NO: 23)
TagATTGaaATGCTGTTT (SEQ ID NO: 24)
TTTtTaTTAtTaTtTTTA

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the present disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the present disclosure, can be excluded from any one or more claims. For purposes of brevity, all of the embodiments in which one or more elements, features, purposes, or aspects is excluded are not set forth explicitly herein.

What is claimed is:

1. A protein comprising a TALE N-terminal domain having an amino acid sequence that is at least 95% identical to the amino acid sequence provided in SEQ ID NO: 1, wherein the amino acid sequence comprises an alanine to glutamic acid amino acid substitution at the amino acid residue corresponding to position A39 of SEQ ID NO: 1 and/or a lysine to glutamic acid substitution at the amino acid residue corresponding to position K19 of SEQ ID NO:1, wherein the protein has DNA-binding activity.

2. The protein of claim 1, wherein the amino acid sequence is at least 98% identical to the amino acid sequence provided in SEQ ID NO: 1.

3. The protein of claim 1, wherein the amino acid sequence further comprises an alanine to glutamic acid substitution at the amino acid residue corresponding to position A93 of SEQ ID NO: 1.

4. The protein of claim 1, wherein the amino acid sequence further comprises a glycine to arginine amino acid substitution at the amino acid residue corresponding to position G98 of SEQ ID NO: 1.

5. The protein of claim 1, wherein the amino acid sequence further comprises one or more amino acid substitutions at the positions corresponding to S22, G77, A85, T91, A93, P99, A139, and N136 of SEQ ID NO: 1.

6. The protein of claim 1, wherein the amino acid sequence further comprises an arginine to tryptophan amino acid substitution at the amino acid residue corresponding to position R21 of SEQ ID NO: 1.

7. The protein of claim 1, wherein the protein comprises a TALE repeat array that binds a target sequence comprised in a genome.

* * * * *